United States Patent
Vodovotz et al.

(10) Patent No.: US 10,137,236 B2
(45) Date of Patent: Nov. 27, 2018

(54) SELF-REGULATING DEVICE FOR MODULATING INFLAMMATION

(71) Applicant: University of Pittsburgh—Of the Commonwealth System of Higher Education, Pittsburgh, PA (US)

(72) Inventors: Yoram Vodovotz, Sewickley, PA (US); Alexey Solovyev, Pittsburgh, PA (US); David Okonkwo, Pittsburgh, PA (US); Maxim Mikheev, Clairton, PA (US); Qi Mi, Pittsburgh, PA (US); Jorg Gerlach, Pittsburgh, PA (US); Gregory M Constantine, Baden, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 562 days.

(21) Appl. No.: 14/301,734

(22) Filed: Jun. 11, 2014

(65) Prior Publication Data

US 2014/0350527 A1    Nov. 27, 2014

Related U.S. Application Data

(62) Division of application No. 13/121,013, filed as application No. PCT/US2009/058767 on Sep. 29, 2009, now abandoned.

(60) Provisional application No. 61/100,845, filed on Sep. 29, 2008.

(51) Int. Cl.
*A61M 1/34* (2006.01)
*A61M 1/00* (2006.01)
*B01D 63/02* (2006.01)
*A61M 1/36* (2006.01)

(52) U.S. Cl.
CPC ........ *A61M 1/3489* (2014.02); *A61M 1/0088* (2013.01); *A61M 1/3472* (2013.01); *A61M 1/3482* (2014.02); *A61M 1/367* (2013.01); *B01D 63/026* (2013.01)

(58) Field of Classification Search
None
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,270,192 A | 12/1993 | Li et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,554,389 A | 9/1996 | Badylak et al. | |
| 5,573,784 A | 11/1996 | Badylak et al. | |
| 5,605,835 A | 2/1997 | Hu et al. | |
| 5,645,860 A | 7/1997 | Knapp, Jr. et al. | |
| 5,711,969 A | 1/1998 | Patel et al. | |
| 5,753,267 A | 5/1998 | Badylak et al. | |
| 5,762,966 A | 6/1998 | Knapp, Jr. et al. | |
| 5,771,969 A | 6/1998 | Garay | |
| 5,866,414 A | 2/1999 | Badylak et al. | |
| 6,099,567 A | 8/2000 | Badylak et al. | |
| 6,472,200 B1 | 10/2002 | Mitrani | |
| 6,485,723 B1 | 11/2002 | Badylak et al. | |
| 6,509,147 B1 | 1/2003 | Altrichter et al. | |
| 6,576,265 B1 | 6/2003 | Spievack | |
| 6,579,538 B1 | 6/2003 | Spievack | |
| 6,582,955 B2 | 6/2003 | Martinez et al. | |
| 6,696,270 B2 | 2/2004 | Badylak et al. | |
| 6,759,245 B1 | 7/2004 | Toner et al. | |
| 6,783,776 B2 | 8/2004 | Spievack | |
| 6,793,939 B2 | 9/2004 | Badylak | |
| 6,849,273 B2 | 2/2005 | Spievack | |
| 6,852,339 B2 | 2/2005 | Spievack | |
| 6,858,146 B1 | 2/2005 | Myers et al. | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 7,160,719 B2 | 1/2007 | Nyberg | |
| 7,273,465 B2 | 9/2007 | Ash | |
| 2003/0017142 A1 | 1/2003 | Toner et al. | |
| 2003/0087285 A1 | 5/2003 | Chow et al. | |

(Continued)

FOREIGN PATENT DOCUMENTS

| | | | |
|---|---|---|---|
| WO | 2008067042 A2 | 6/2008 | |
| WO | 2008150720 A1 | 12/2008 | |
| WO | 2009042768 A1 | 4/2009 | |

OTHER PUBLICATIONS

Clermont et al. Critical Care Medicine, 2004; 32(10): 2061-2070.*
Rygg et al. Scandinavian Journal of Immunology. 53:588-595, 2001.*
Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990.*

(Continued)

*Primary Examiner* — Vanessa L. Ford
*Assistant Examiner* — Sandra E Dillahunt
(74) *Attorney, Agent, or Firm* — The Webb Law Firm

(57) ABSTRACT

A bioreactor is provided which contains cells capable of producing cytokine inhibitors in response to cytokines, in a manner regulated by the local or systemic milieu of an individual patient and predicted by mechanistic computational simulations. The bioreactor transfers the cytokine inhibitors to a patient in need of control of the inflammation process as part of a disease or condition in the patient, such as sepsis, trauma, traumatic brain injury, or wound healing. Related methods also are provided.

17 Claims, 36 Drawing Sheets

Specification includes a Sequence Listing.

(56) References Cited

U.S. PATENT DOCUMENTS

| | | | |
|---|---|---|---|
| 2003/0130194 A1* | 7/2003 | Altrichter | A61K 35/13 424/93.7 |
| 2005/0003535 A1 | 1/2005 | Gerlach | |
| 2005/0015064 A1 | 1/2005 | Gerlach | |
| 2005/0032218 A1 | 2/2005 | Gerlach | |
| 2005/0049581 A1 | 3/2005 | Gerlach | |
| 2005/0182349 A1 | 8/2005 | Linde et al. | |
| 2007/0249538 A1 | 10/2007 | Sazani et al. | |
| 2008/0145442 A1 | 6/2008 | Yarmush et al. | |
| 2008/0228456 A1 | 9/2008 | Clermont et al. | |

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988.*

Bork. Powers and Pitfalls in Sequence Analysis: The 70% Hurdle. Genome Research, 2000,10:398-400.*

Vajdos et al. Comprehensive Functional Maps of the Antigen binding Site of an Anti-ErbB2 Antibody Obtained with Shotgun Scanning Mutagenesis. Journal of Molecular Biology Jul. 5, 2002;320(2):415-28.*

Brown et al. Tolerance to Single, but Not Multiple, Amino Acid Replacements in Antibody VH CDR2. Journal of Immunology, May 1996; 156 (9):3285-91.*

Vodovotz et al. "Mechanistic simulations of inflammation: Current state and future prospects" Mathematical Biosciences, 2009, pp. 1-10, vol. 217.

Vodovotz "Deciphering the Complexity of Acute Inflammation Using Mathematical Models" Immunologic Research, 2006, pp. 237-245, vol. 36, Nos. 1-3.

Wang et al. "Mathematical Analysis and Quantification of Fluorescent Proteins as Transcriptional Reporters" Biophysical Journal, Mar. 2008, pp. 2017-2026, vol. 94.

Waniewski et al. "A mathematical model of extracorporeal antibody removal in autoimmune disease" The International Journal of Artifical Organs, 1989, pp. 471-476, vol. 12, No. 7.

Zamora et al. "Transforming growth factor-beta in critical illness" Crit Care Med, 2005, pp. s478-s481, vol. 33, No. 12.

Zeilinger et al. "Time Course of Primary Liver Cell Reorganization in Three-Dimensional High-Density Bioreactors for Extracorporeal Liver Support: An Immunohistochemical and Ultrastructural Study," Tissue Engineering, 2004, pp. 1113-1124, vol. 10, No. 7/8.

Rygg et al. "In vitro Evaluation of an Enhanced Human Serum Amyloid A (SAA2) Promoter-Regulated Soluble TNF Receptor Fusion Protein for Anti-Inflammatory Gene Therapy" Scand. J. Immunol., 2001, pp. 588-595, vol. 53.

He et al. "Expression of sTNFR-IgFc fusion gene in endothelial cell and its application in gene therapy for rheumatoid arthritis" Chinese Journal of Biotechnology, 2006, pp. 378-383, vol. 22, No. 3, Abstract Only.

Aggarwal, et al. "TNF blockade: an inflammatory issue" Ernst Schering. Research Foundation Workshop, 2006, pp. 161-186, vol. 56.

Aller et al. "Posttraumatic inflammation is a complex response based on the pathological expression of the nervous, immune, and endocrine functional systems" Society for Experimental Biology and Medicine, 2004, pp. 170-181, vol. 229.

An et al "Challenges and rewards on the road to translational systems biology in acute illness: four case reports from interdisciplinary teams" J. Crit Care, 2007, pp. 169-175, vol. 22, No. 2.

An et al. "Translational systems biology: introduction of an engineering approach to the pathophysiology of the burn patient" J. Burn Care Res, 2008, pp. 277-285, vol. 29.

Ancey et al. "A fusion protein of the gp130 and interleukin-6Ralpha Ligand-binding Domains Acts as a Potent Interleukin-6 Inhibitor" The Journal of Biological Chemistry, 2003, pp. 16968-16972, vol. 278, No. 19.

Annes et al. "Making sense of latent TGFbeta activation" J. Cell Science, 2003, pp. 217-224, vol. 116.

Bottinger et al. "The recombinant proregion of transforming growth factor beta1 (latency-associated peptide) inhibits active transforming growth factor beta1 in transgenic mice" Proc. Natl. Acad. Sci. 1996, pp. 5877-5882, vol. 93.

Brown et al. "Complexities of targeting innate immunity to treat infection" Trends in Immunology, 2007, pp. 260-266, vol. 28, No. 6.

Bruining, "A General Description of Flows and Pressures in Hollow Fiber Membrane Modules" Chemical Engineering Science, 1989, pp. 1441-1447, vol. 44, No. 6.

Chow et al. "The Acute Inflammatory Response in Diverse Shock States" Shock, 2005, pp. 74-84, vol. 24, No. 1.

Clermont et al. "In silico design of clinical trials: A method coming of age" Crit Care Med, 2004, pp. 2061-2070, vol. 32, No. 10.

Constantine et al. "A Parameter Search Algorithm Based on Optimal Linear Codes" International Journal of Pure and Applied Mathematics, 2006, pp. 9-22, vol. 31, No. 1.

Constantine et al. "A linear code parameter search algorithm with applications to immunology" Comput Optim Appl, 2009, pp. 155-171, vol. 42.

Daun et al. "An ensemble of models of the acute inflammatory response to bacterial lipopolysaccharide in rats: results from parameter space reduction" Journal of Theoretical Biology, 2008, pp. 843-853, vol. 253.

Day et al. "A reduced mathematical model of the acute inflammatory response: II. Capturing scenarios of repeated endotoxin administration" J. Theor. Biol. pp. 235-256, 2006, vol. 242, No. 1.

Dennler et al. "Direct binding of Smad3 and Smad4 to critical TGF beta-inducible elements in the promoter of human plasminogen activator inhibitor-type 1 gene" The EMBO Journal, 1998, pp. 3091-3100, vol. 17, No. 11.

Dinarello, "Therapeutic strategies to reduce IL-1 activity in treating local and systemic inflammation" Current Opinion in Pharmacology, 2004, pp. 378-385, vol. 4.

Economides et al. "Cytokine traps: multi-component, high-affinity blockers of cytokine action" Nature Medicine, 2003, pp. 47-52, vol. 9, No. 1.

Enosawa et al., "Long-Term Culture of Glutamine Synthetase-Transfected HepG2 Cells in Circulatory Flow Bioreactor for Development of a Bioartificial Liver" Cell Transplantation, 2000, pp. 711-715, vol. 9.

Federspiel et al. "Gas flow dynamics in hollow-fiber membranes" AIChE Journal, 1996, pp. 2094-2099, vol. 42, No. 7.

Fernandez-Botran et al. "Soluble cytokine receptors in biological therapy" Expert Opin. Biol. Ther., 2002, pp. 585-605, vol. 2, No. 6.

Fortenberry et al. "Extracorporeal Therapies in the Treatment of Sepsis: Experience and Promise" Seminars in Pediatric Infectious Diseases, 2006, pp. 72-79, vol. 17.

Gallucci et al. "Danger signals: SOS to the immune system" Current Opinion in Immunology, 2001, pp. 114-119, vol. 13.

Gerlach, "Bioreactors for Extracorporeal Liver Support" Cell Transplantation, 2006, pp. S91-S103, vol. 15, supplement 1.

Gerlach et al. "Endothelial cell seeding on different polyurethanes" Artifical Organs, 1989, pp. 144-147, vol. 13, No. 2.

Gerlach et al. "Comparison of hollow fibre membranes for hepatocyte immobilisation in bioreactors" International Journal. Artifical Organs, 1996, pp. 610-616, vol. 19 No. 10.

Gerlach et al. "Gas supply across membranes in bioreactors for hepatocyte culture" Artificial Organs, 1990, pp. 328-333, vol. 14, No. 5.

Goldring, "Inflammatory Mediators as Essential Elements in Bone Remodeling," Calcif Tissue Int, 2003, pp. 97-100, vol. 73.

Goris, "Pathophysiology of Shock in Trauma, European Journal of Surgery," 2000, pp. 100-111, vol. 166.

Guilak et al. "The Role of Biomechanics and Inflammation in Cartilage Injury and Repair" Clinical Orthopaedics and Related Research, 2004, pp. 17-26, No. 423.

Hart, "Inflammation. 1: Its role in the healing of acute wounds" Journal of Wound Care, 2002, pp. 205-209, vol. 11.

Hart, "Inflammation. 2: Its role in the healing of chronic wounds" Journal of Wound Care, 2002, pp. 245-249, vol. 11, No. 7.

(56) References Cited

OTHER PUBLICATIONS

Hasegawa et al. "Modifying TNFalpha for Therapeutic Use: A Perspective on the TNF Receptor System" Mini Reviews in Medicinal Chemisty, 2001, pp. 5-16, vol. 1.

Kelsey et al, "Theoretical Analysis of Convective Flow Profiles in a Hollow-Fiber Membrane Bioreactor" Chemical Engineering Science, 1990, pp. 3211-3220, vol. 45, No. 11.

Kumar et al. "The dynamics of acute inflammation" Journal of Theoretical Biology, 2004, pp. 145-155, vol. 230.

Kumar et al. "A Mathematical Simulation of the Inflammatory Response to Anthrax Infection" Shock, 2008, pp. 104-111, vol. 29, No. 1.

Lagoa et al. "The Role of Initial Trauma in the Host's Response to Injury and Hemorrhage: Insights from a Correlation of Mathematical Simulations and Hepatic Transcriptomic Analysis." Shock, 2006, pp. 592-600, vol. 26, No. 6.

Li et al. "A Patient-Specific in silico Model of Inflammation and Healing Tested in Acute Vocal Fold Injury" PLoS One, Jul. 2008, p. e2789, vol. 3, issue 7.

Mi et al. "Agent-based model of inflammation and wound healing: insights into diabetic foot ulcer pathology and the role of transforming growth factor-beta1" Wound Rep. Reg., 2007, pp. 671-682, vol. 15.

Nathan, "Points of control in inflammation" Nature, 2002, pp. 846-852, vol. 420.

Plushner,"Tocilizumab: An Interleukin-6 Receptor Inhibitor for the Treatment of Rheumatoid Arthritis" The Annals of Pharmacotherapy, Nov. 2008, pp. 1660-1668, vol. 42.

Prince et al. "In Silico and In Vivo Approach to Elucidate the Inflammatory Complexity of CD14-deficient Mice" Mol. Med, 2006, pp. 88-96, vol. 12, Nos. 4-6.

Ramadori, "Inflammation, Damage Repair, Immune Cells, and Liver Fibrosis: Specific or Nonspecific, This Is the Question" Gastroenterology, 2004, pp. 997-1000, vol. 127, No. 3.

Redd et al. "Wound healing and inflammation: embryos reveal the way to perfect repair" Phil. Trans. R. Soc. Lond B, 2004, pp. 777-784, vol. 359.

Reynolds et al. "A reduced mathematical model of the acute inflammatory response: I. Derivation of model and analysis of anti-inflammation" Journal of Theoretical Biology, 2006, pp. 220-236, vol. 242, No. 1.

Starling, "On the Absorption of Fluids from the Connective Tissue Spaces." Journal of Physiol., 1896, pp. 312-326, vol. 19 No. 4.

Szymczak et al. "Correction of multi-gene deficiency in vivo using a single 'self-cleaving' 2A peptide-based retroviral vector" Nature Biotechnology, 2004, pp. 589-594, vol. 22, No. 5.

Torres et al. Mathematical Modeling of Posthemorrhage Inflammation in Mice: Studies using a Novel, Computer-Controlled, Closed-Loop Hemorrhage Apparatus, Shock, 2009, pp. 172-178, vol. 32 No. 2.

Upperman et al. "Mathematical modeling in necrotizing enterocolitis—a new look at an ongoing problem" Journal of Pediatric Surgery, 2007, pp. 445-453, vol. 42.

Vodovotz et al. "Translational systems biology of inflammation" PLoS Computational Biology, Apr. 2008, pp. 1-6, vol. 4, issue 4.

\* cited by examiner

```
                                                3xNFkB-TK
      CGCTGCTTCG GATCCGGGGA CTTTCCCGGG GACTTTCCCG GGGACTTTCC
            3xNFkB-TK
101   CCTCGAGATC CGGCAAACCC CGCCCAGCGT CTTGTCATTG GCGAATTCGA ACACGCAGAT GCAGTCGGGG CGGCGCGGTC CGAGGTCCAC TTCGCATATT
            3xNFkB-TK
201   AAGGTGACGC GTGTGGCCTC GAACACCGAG CGACCCGCTA GCGACCCGCT TAACAGCGTC AACAGCGTGC CGCAGATCCA CTAGTAACGG CCGCCAGTGT
                                                                                         sTNFR1A
301   GCTGGAATTC TGCAGATCAT GGGTCTCCCC ACCGTGCCTG GCCTGCTGCT GTCACTGGTG CTCCTGCCTC TGCTGATGGG GATACATCCA TCAGGGGTCA
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
401   CTGGACTAGT CCCTTCTCTT GGTGACCGGG AGAAGAGGGA TAGCTTGTGT CCCCAAGGAA AGTATGTCCA TTCTAAGAAC AATTCCATCT GCTGCACCAA
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
501   GTGCCACAAA GGAACCTACT TGGTGAGTGA CTGTCCGAGC CCAGGGCGGG ATACAGTCTG CAGGGAGTGT GAAAAGGGCA CCTTTACGGC TTCCCAGAAT
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
601   TACCTCAGGC AGTGTCTCAG TTGCAAGACA TGTCGGAAAG AAATGTCCCA GGTGGAGATC TCTCCTTGCC AAGCTGACAA GGACACGGTG TGTGGCTGTA
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
701   AGGAGAACCA GTTCCAACGC TACCTGAGTG AGACACACTT CCAGTGCGTG GACTGCAGCC CCTGCTTCAA CGGCACCGTG ACAATCCCCT GTAAGGAGAC
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
801   TCAGAACACC GTGTGTAACT GCCATGCAGG GTTCTTTCTG AGAGAAAGTG AGTGCGTCCC TTGCAGCCAC TGCAAGAAAA ATGAGGAGTG TATGAAGTTG
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                        sTNFR1A
901   TGCCTACCTC CTCCGCTTGC AAATGTCACA AACCCCCAGG ACTCAGGTAC TGCCGGTGTAA GCTAGGATCC
      ~~~~~~~~~~~~~~~~~~~~~~~~~~~~~~~~~~~~~~~~~~~~~~~~~~~~~~~~~~~~~~~~~~~~~~~~~~~~
```

Fig. 6B

```
                                                       3xNFkB-TK
 501  CTTTGTATAC AAAAGTGTGT GATCCGGGGA CTTTCCCGGG GACTTTCCCC CCTCGAGATC CGGCAAAACCC CGCCCAGCGT CTTGTCATTG
                              3xNFkB-TK
 601  GCGAATTCGA ACACGCAGAT GCAGTCGGGG CGGCGCGGTC CGAGGTCCAC TTCGCATATT AAGGTGACGC GTGTGGCCTC GAACACCGAG CGACCCTGCA
        3xNFkB-TK                                                                                           sTNFR1A
 701  GCGACCCGCT TAACAGCGTC AACAGCCGTGC CGCAGATCCA CTAGTAACGG CCGCCAGTGT GCTGGAATTC TGCAGATCAT GGGTCTCCCC ACCGTGCCTG
                                                              sTNFR1A
 801  GCCTGCTGCT GTCACTGGTG CTCCTGGCTC TGCTGATGGG GATACATCCA TCAGGGGTCA CTGGACTAGT CCCTTCTCTT GGTGACCGGG AGAAGAGGGA
                                                                  sTNFR1A
 901  TAGCTTGTGT CCCCAAGGAA AGTATGTCCA TTCTAAGAAC AATTCCATCT GCTGCACCAA GTGCCACAAA GGAACCTACT TGGTGAGTGA CTGTCCGAGC
                                                                              sTNFR1A
1001  CCAGGGGCGGG ATACAGTCTG CAGGGAGTGT GAAAAGGGCA CCTTTACGGC TTCCCAGAAT TACCTCAGGC AGTGTCTCAG TTGCAAGACA TGTCGGAAAG
                                                                                            sTNFR1A
1101  AAATGTCCCA GGTGGAGATC TCTCCTTGCC AAGCTGACAA GGACACGGTG TGTGGCTGTA AGGAGAACCA GTTCCAACGC TACCTGAGTG AGACACACTT
                                                                                                    sTNFR1A
1201  CCAGTGCGTG GACTGCAGCC CCTGCTTCAA CGGCACCGTG ACAATCCCCT GTAAGGAGAC TCAGAACACC GTGTGTAACT GCCATGCAGG GTTCTTTCTG
                                                                                                        sTNFR1A
1301  AGAGAAAGTG AGTGCGTCCC TTGCAGCCAC TGCAAGAAAA ATGAGGAGTG TATGAAGTTG TGCCTACCTC CTCCGCTTGC AAATGTCACA AACCCCCAGG
           sTNFR1A                                                                                             IRES
1401  ACTCAGGTAC TGCGGTGTAA GCACCCAACT TTTCTATACA AAGTTGCTGC TAGCCTCGAG AATTCACGCG TCGAGCATGC ATCTAGGGCG GCCAATTCCG
```

Fig. 14B-1

```
                IRES
1501  CCCCTCTCCC TCCCCCCCCC CTAACGTTAC TGGCCGAAGC CGCTTGAAT AAGGCCGGTG TGCGTTTGTC TATATGTGAT TTTCCACCAT ATTGCCGTCT
                        IRES
1601  TTTGGCAATG TGAGGGCCCG GAAACCTGGC CCTGTCTTCT TGACGAGCAT TCCTAGGGGT CTTTCCCCTC TGCCAAAGG AATGCAAGGT CTGTTGAATG
                        IRES
1701  TCGTGAAGGA AGCAGTTCCT CTGGAAGCTT CTTGAAGACA AACAACGTCT GTAGCGACCC TTTGCAGGCA GCGGAACCCC CCACCTGGCG ACAGGTGCCT
                        IRES
1801  CTGCGGCCAA AAGCCACGTG TATAAGATAC ACCTGCAAAG GCGGCACAAC CCCAGTGCCA CGTTGTGAGT TGGATAGTTG TGGAAAGAGT CAAATGGCTC
                        IRES
1901  TCCTCAAGCG TATTCAACAA GGGGCTGAAG GATGCCCAGA AGTACCCCA TTGTATGGGA TCTGATCTGG GGCCTCGGTG CACATGCTTT ACATGTGTTT
                        IRES
2001  AGTCGAGGTT AAAAAAAACGT CTAGGCCCCC CGAACCACGG GGACGTGTGT TTCCTTTGAA AAACACGATG ATAAGCTTGC CACAACCCGA CAACTTTGTA
                                                                                                    TurboFP635
2101  TAATAAAGTT GCTGCTAGCG CTACCGGACT CAGATCTCGA GCTCAAGCTT CGAATTCTGC AGTCGACGGT ACCGCGGGCC CGGTCGCCAC CGGTCGCCAC
                        TurboFP635
2201  CATGGTGGGT GAGGATAGCG TGCTGATCAC CGAGAACATG CACATGAAAC TGTACATGGA GGGCACCGTG AACGACCACC ACTTCAAGTG CACATCCGAG
                        TurboFP635
2301  GGCGAAGGCA AGCCCTACGA GGGCACCCAG ACCATGAAGA TCAAGGTGGT CGAGGGGCGC CCCTCTCCCT TCGCCTTCGA CATCCTGGCT ACCAGTTCA
                        TurboFP635
2401  TGTACGGCAG CAAAACCTTT ATCAACCACA CCCCAGGGCAT CCCCGACTTC TTTAAGCAGT CCTTCCCTGA GGGCTTCACA TGGGAGAGGA TCACCACATA
```

*Fig. 14B-2*

```
                                       TurboFP635
       ~~~~~~~~~~ ~~~~~~~~~~ ~~~~~~~~~~ ~~~~~~~~~~ ~~~~~~~~~~ ~~~~~~~~~~
2501   CGAAGACGGG GGCGTGCTGA CCGCTACCCA GGACACCAGC CTCCAGAACG GCTGCCTCAT CTACAACGTC AAGATCAACG GGGTGAACTT CCCATCCAAC
                                                TurboFP635
       ~~~~~~~~~~ ~~~~~~~~~~ ~~~~~~~~~~ ~~~~~~~~~~ ~~~~~~~~~~ ~~~~~~~~~~
2601   GGCCCTGTGA TGCAGAAGAA AACACTCGGC TGGGAGGCCA GCACCGAGAT GCTGTACCCC GCTGACAGCG GCCTGAGAGG CCATAGCCAG ATGGCCCTGA
                                       TurboFP635
       ~~~~~~~~~~ ~~~~~~~~~~ ~~~~~~~~~~ ~~~~~~~~~~ ~~~~~~~~~~ ~~~~~~~~~~
2701   AGCTCGTGGG CGGGGGCTAC CTGCACTGCT CCCTCAAGAC CACATACAGA CCGCTAAGAA CCTCAAGATG CCCGGCTTCT ACTTCGTGGA
                                       TurboFP635
       ~~~~~~~~~~ ~~~~~~~~~~ ~~~~~~~~~~ ~~~~~~~~~~ ~~~~~~~~~~ ~~~~~~~~~~
2801   CAGGAGACTG GAAAGAATCA AGGAGGCCGA CAAAGAGACC TACGTCGAGC AGCACGAGAT GGCTGTGGCC AGTACTGCCG ACCTGCCTAG CAAACTGGGG
       TurboFP635                                                                          V5 epitope
       ~~~~~~~~~~                                                               ~~~~~~~~~~~~~~~~~~~~~
2901   CACAGCTGAT ACCCAGCTTT CTTGTACAAA GTTGGTTGAT ATCCAGCACA GTGGCGGCCG CTCGAGTCTA GAGGGCCCGC GGTTCGAAGG TAAGCCTATC
```

Fig. 14B-3

```
                                    T7 RNA pol prom
                       ~~~~~~~~~~~~~~~~~~~~~~~~~~~~~~~~~~~~~~~~~~~~~~~~~~~~~~~~~~~~~~~~~~~
1601  AGTTCAATTA CAGCTCTTAA GGCTAGAGTA CTTAATACGA CTCACTATAG GCTAGCAGAA TCTGCTTAGG GTTAGGCGTT TTGCGCTGCT TCGGATCCAC
                                                                          ~~~~~~~~~~~~~~~~~~~~~~~~~~~~~~~~~~~~~~~~
                                                                                      3xIL1RE-TK
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
1701  ATTGCACAAT CTACACTGCA CAATCTACAT TGCACAATCT CTCGAGATCC GGCAAACCCC GCCCAGCGTC TTGTCATTGG CGAATTCGAA CACGCAGATG
         3xIL1RE-TK
      ~~~~~~~~~~~~~~~~~~~~
1801  CAGTCGGGGC GGGCGCGGTCC GAGGTCCACT TCGCATATTA AGGTGACGCG TGTGGCCTCG AACACCGAGC GACCCTGCAG CGACCCGCTT AACAGCGTCA
         3xIL1RE-TK                                                     ~~~~~~~~~~~~~~~~~~~~~~~~~~~~~~~~~~~~~~~~~~~
      ~~~~~                                                                   IL1rn
1901  ACAGCGTGCC GCAGATCCAC CCATGGCTTC AGAGGCAGCC TGCCGCCCTT CTGGGAAAAG ACCCTGCAAG ATGCAAGCCT TCAGAATCTG GGATACTAAC
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                            IL1rn
2001  CAGAAGACCT TTTACCTGAG AAACAACCAG CTCATTGCTG GGTACTTACA AGGACCAAAT ATCAAACTAG AAGAAAAGTT AGACATGGTG CCTATTGACC
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                            IL1rn
2101  TTCATAGTGT GTTCTTGGGC ATCCACGGGG GCAAGCTGTG CCTGTCTTGT GCCAAGTCTG GAGATGATAT CAAGCTCCAG CTGGAGGAAG TTAACATCAC
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                           IL1rn
2201  TGATCTGAGC AAGAACAAAG AAGAAGACAA GCGCTTTACC TTCATCCGCT CTGAGAAAGG CCCCACCACC AGCTTTGAGT CAGCTGCCTG TCCAGGATGG
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                           IL1rn
2301  TTCCTCTGCA CAACACTAGA GGCTGACCGT CCTGTGAGCC TCACCAACAC ACCGGAAGAG CCCCTTATAG TCACGAAGTT CTACTTCCAG GAAGACCAAT
      ~~~~~~~~~~~~~~~~~~~~                                                                                  ~~~~~~~~
        IL1rn                                                                                                 IRES
      ~~
2401  AGTACTGCCG AGGCCTGTAA TAATCACCAA CTGCCTGATC ACTCTGGCGA ATTCACGCGT CGAGCATGCA TCTAGGGCGG CCAATTCCGC CCCTCTCCCT
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                             IRES
2501  CCCCCCCCCC TAACGTTACT GGCCGAAGCC GCTTGGAATA AGGCCGGTGT GCGTTTGTCT ATATGTGATT TCCACCATA TTGCCGTCTT TTGGCAATGT
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
```

*Fig. 16B-1*

```
2601  GAGGGCCCGG AAACCTGGCC CTGTCTTCTT GACGAGCATT CCTAGGGGTC TTTCCCCTCT CGCCAAAGGA ATGCAAGGTC TGTTGAATGT CGTGAAGGAA
                                                                      IRES

2701  GCAGTTCCTC TGGAAGCTTC TTGAAGACAA ACAACGTCTG TAGCGACCCT TTGCAGGCAG CGGAACCCCC CACCTGGCGA CAGGTGCCTC TGCGGCCAAA
                                                                      IRES

2801  AGCCACGTGT ATAAGATACA CCTGCAAAGG CGGCACACAA CCCCAGTGCCAC GTTGTGAGTT GGATAGTTGT GGAAAGAGTC AAATGGCTCT CCTCAAGCGT
                                                                      IRES

2901  ATTCAACAAG GGGCTGAAGG ATGCCCAGAA GGTACCCCAT TGTATGGGAT CTGATCTGGG GCCTCGGTGC ACATGCTTTA CATGTGTTTA GTCGAGTTA
                                                                      IRES                                                TurboFP635

3001  AAAAAACGTC TAGGCCCCCC GAACCACGGG GACGTGGTTT TCCTTTGAAA AACACGATGA TAAGCTTGCC ACAACCCGGG ATCCACCGGT CGCCACCATG
                                                                                                                    TurboFP635

3101  GTGGGTGAGG ATAGCGTGCT GATCACCGAG AACATGCACA TGAAACTGTA CATGGAGGGC ACCGTGAACG ACCACCACTT CAAGTGCACA TCCGAGGGCG
                                                                      TurboFP635

3201  AAGGCAAGCC CTACGAGGGC ACCCAGACCA ACCAGATCAA GGTGGTCGAG GGCGGCCCTC TCCCCTTCGC CTTCGACATC CTGGCTACCA GCTTCATGTA
                                                                      TurboFP635

3301  CGGCAGCAAA ACCTTTATCA ACCACACCCA GGGCATCCCC GACTTCTTTA AGCAGTCCTT CCCTGAGGGC TTCACATGGG AGAGGATCAC CACATACGAA
                                                                      TurboFP635

3401  GACGGGGGCG TGCTGACCGC TACCCAGGAC ACCAGCCTCC AGAACGGCTG CCTCATCTAC AACGTCAAGA TCAACGGGGT GAACTTCCCA TCCAACGGCC
```

```
                                                                                 TurboFP635
       CTGTGATGCA GAAGAAAACA CTCGGCTGGG AGGCCAGCAC CGAGATGCTG TACCCCGCTG ACAGCGGCCT GAGAGGCCAT AGCCAGATGG CCCTGAAGCT
3501   ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                  TurboFP635
       CGTGGGCGGG GGCTACCTGC ACTGCTCCCT CAAGACCACA TACAGATCCA AGAAACCCGC TAAGAACCTC AAGATGCCCG GCTTCTACTT CGTGGACAGG
3601   ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                                  TurboFP635
       AGACTGGAAA GAATCAAGGA GGCCGACAAA GAGACCTACG TCGAGCAGCA CGAGATGGCT GTGGCCAGGT ACTGCGACCT GCCTAGCAAA CTGGGGCACA
3701   ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
       TurboFP635
       ~~~~~~
       GCTGATGCGG CCGCTTCCCT TTAGTGAGGG TTAATGCTTC GAGCAGACAT GACGCGTACC GGTTAGTAAG CGTACCGGTT AGTAAT
3801                                                                     ~~~~~~~~~~ ~~~~~~~~~~ ~~~~~~
                                                                                 T3 RNA pol promoter
```

Fig. 16B-3

```
                                                                                3xNFkB-TK
1701  CGAATTCTGC AGTCGACGGT ACCGCGGGCC CGGGATCCAC CGGTACAACT TTGTATACAA AAGTTGTGGA TCCGGGGACT TCCCGGGGA CTTTCCCGGG
                                                       3xNFkB-TK
1801  GACTTTCCCC TCGAGATCCG GCAAACCCCG CCCAGCGTCT TGTCATTGGC GAATTCGAAC ACGCAGATGC AGTCGGGGCG GCGCGGTCCG AGGTCCACTT
                                    3xNFkB-TK
1901  CGCATATTAA GGTGACGCGT GTGGCCTCGA ACACCGAGCG ACCCGCTTA ACAGCGTCAA CAGGGTGCCG CAGATCCACT AGTAACGGCC
                                                                                                     sTNFR1A
2001  GCCAGTGTGC TGGAATTCTG CAGATCATGG GTCTCCCCAC CGTGCCTGGC CTGCCTCTGT CACTGGTGCT CCTGGCTCTG CTGATGGGGA TACATCCATC
                                                                   sTNFR1A
2101  AGGGGTCACT GGACTAGTCC CTTCTCTTGG TGACCGGGAG AAGAGGGATA GCTTGTGTCC CCAAGGAAAG TATGTCCATT CTAAGAACAA TTCCATCTGC
                                                                   sTNFR1A
2201  TGCACCAAGT GCCACAAAGG AACCTACTTG GTGAGTGACT GTCCGAGCCC AGGGCGGGAT ACAGTCTGCA GGAGTGTGA AAAGGGCACC TTTACGGCTT
                                                                   sTNFR1A
2301  CCCAGAATTA CCTCAGGCAG TGTCTCAGTT GCAAGACATG TCGGAAAGAA ATGTCCCAGG TGGAGATCTC TCCTTGCCAA GCTGACAAGG ACACGGTGTG
                                                                   sTNFR1A
2401  TGGCTGTAAG GAGAACCAGT TCCAACGCTA CCTGAGTGAG ACACACTTCC AGTGCGTGGA CTGCAGCCCC TGCTTCAACG GCACCGTGAC AATCCCCTGT
                                                                   sTNFR1A
2501  AAGGAGACTC AGAACACCGT GTGTAACTGC CATGCAGGGT TCTTTCTGAG AGAAAGTGAG TGCGTCCCTT GCAGCCACTG CAAGAAAAAT GAGGAGTGTA
```

*Fig. 17B-1*

```
                                                                                           T2A
          sTNFR1A                              ~~~~~~~~~~~~~~~~~~~~~~~~~~~~~~~~~~~~~~~~~~~~~~~~~~
     ~~~~~~~~~~~~~~~
2601 TGAAGTTGTG CCTACCTCCT CCGCTTGCAA ATGTCACAAA CCCCCAGAGAC TCAGGTACTG CGGTGTAAGC ACCCAACTTT TCTATACAAA GTTGCTGCTA
                                                               T2A
     ~~~~~~~~~~~~~~~~~~~~~~~~~~~~~~~~~~~~~~~~~~~~~~~~~~~~~~~~~~~~~~~~
2701 GCCTCGAGAA TTCACGCGTC GAGCATGCAT CTAGGGCGGC CACAACTTTG TATAATAAAG TTGCTGCTAG CGCTACCGGA CTCAGATCTC GAGCTCAAGC
          T2A                                                                TurboFP635
     ~~~~~~~~~
2801 TTCGAATTCT GCAGTCGACG GTACCGCGGG CCCGGGATCC ACCGGTCGCC ACCATGGTGG GTGAGGATAG CGTGCTGATC ACCGAGAACA TGCACATGAA
                                                           TurboFP635
2901 ACTGTACATG GAGGGCACCG TGAACGACCA CCACTTCAAG TGCACATCCG AGGGCGAAGG CAAGCCCTAC GAGGGCACCC AGACCATGAA GATCAAGGTG
                                                           TurboFP635
3001 GTCGAGGGCG GCCCTCTCCC CTTCGCCTTC GACATCCTGG CTACCAGCTT CATGTACGGC AGCAAAACCT TTATCAACCA CACCCAGGGC ATCCCCGACT
                                                           TurboFP635
3101 TCTTTAAGCA GTCCTTCCCT GAGGGCTTCA CATGGGAGAG GATCACCACA TACGAAGACG GGGGCGTGCT GACCGCTACC CAGGACACCA GCCTCCAGAA
                                                           TurboFP635
3201 CGGCTGCCTC ATCTACAACG TCAAGATCAA CGGGGTGAAC TTCCCATCCA ACGGCCCTGT GATGCAGAAG AAAACACTCG GCTGGGAGGC CAGCACCGAG
                                                           TurboFP635
3301 ATGCTGTACC CCGCTGACAG CGGACTATAGCC GGCCATAGCC AGATGGCCCT GAAGCTCGTG GGCGGGGGCT ACCTGCACTG CTCCCCTCAAG ACCACATACA
```

*Fig. 17B-2*

```
                TurboFP635
3401  ~~~~~~~~~~ GATCCAAGAA ACCCGCTAAG AACCTCAAGA TGCCCGGCTT CTACTTCGTG GACAGGAGAC TGGAAAGAAT CAAGGAGGCC GACAAAGAGA CCTACGTCGA ~~~~~~~~~~
                TurboFP635
3501  ~~~~~~~~~~ GCAGCACGAG ATGGCTGTGG CCAGGTACTG CGACCTGCCT AGCAAACTGG GCACACAGCT ATACCCAGCT TTCTTGTACA AAGTGGTTTG ATATCCAGCA
```

Fig. 17B-3

```
                                                                                          3xNFkB-TK
1701    CGAATTCTGC AGTCGACGGT ACCGCGGGCC CGGGATCCAC CGGTACAACT TTGTATACAA AAGTTGTGGA TCCGGGGACT TCCCGGGGA CTTTCCCGGG
                                                                3xNFkB-TK
1801    GACTTTCCCC TCGAGATCCG CCCAGCGTCT TGTCATTGGC GAATTCGAAC ACGCAGAGATGC ACGGCAGATC AGTCGGGGCG GCGCGGTCCG AGGTCCACTT
                3xNFkB-TK
1901    CGCATATTAA GGTGACGCGT GTGGCCTCGA ACACCGAGCG ACCCTGCAGC ACCCGCCTTA ACAGCGTCAA CAGCGTGCCG CAGATCCACT AGTAACGGCC
                                                                        TurboFP635
2001    GCCAGTGTGC TGGAATCGAA TTCTGCAGTC GACGGTACCG CGGGCCCGGG ATCCACCGGT CGCCACCATG GTGGGTGAGG ATAGCGTGCT GATCACCGAG
                TurboFP635
2101    AACATGCACA TGAAACTGTA CATGGAGGGC ACCGTGAACG ACCACCACTT CAAGTGCACA TCCGAGGGCG AAGGCAAGCC CTACGAGGGC ACCCAGACCA
                TurboFP635
2201    TGAAGATCAA GGTGGTCGAG GGCGGCCCTC TCCCCTTCGC CTGGCTACCA GCTTCATGTA CGGCAGCAAA ACCTTTATCA ACCACACCCA
                TurboFP635
2301    GGGCATCCCC GACTTCTTTA AGCAGTCCTT CCCTGAGGGC TTCACATGGG AGAGGATCAC CACATACGAA GACGGGGGCG TGCTGACCGC TACCCAGGAC
                TurboFP635
2401    ACCAGCCTCC AGAACGGCTG CCTCATCTAC AACGTCAAGA TCAACGGGGT GAACTTCCCA TCCAACGGCC CTGTGATGCA GAAGAAAACA CTCGGCTGGG
                TurboFP635
2501    AGGCCAGCAC CGAGATGCTG TACCCCGCTG ACAGCGGCCT GAGAGGCCAT AGCCAGATGG CCCTGAAGCT CGTGGGCGGG GCTACCTGC ACTGCTCCCT
```

Fig. 18B-1

```
                                            TurboFP635
2601 CAAGACCACA TACAGATCCA AGAAACCCGC TAAGAACCTC AAGATGCCCG GCTTCTACTT CGTGGACAGG AGACTGGAAA GAATCAAGGA GGCCGACAAA TurboFP635
2701 GAGACCTACG TCGAGCAGCA CGAGATGGCT GTGGCCAGGT ACTGCGACCT GCCTAGCAAA CTGGGGCACA GCTGATACCC AGCTTTCTTG TACAAAGTGG
```

*Fig. 18B-2*

```
   1 acacggcgtc cctcaggcgc ccccattccg gaccagccct cgggagtcgc cgacccggcc
  61 tcccgcaaag acttttcccc agacctcggg cgcaccccct gcacgccgcc ttcatccccg
 121 gcctgtctcc tgagcccccg cgcatcctag acccttctc ctccaggaga cggatctctc
 181 tccgacctgc cacagatccc ctattcaaga ccacccacct tctggtacca gatcgcgccc
 241 atctaggtta tttccgtggg atactgagac accccggtc caagcctccc ctccaccact
 301 gcgcccttct ccctgaggac ctcagctttc cctcgaggcc ctcctacctt ttgccgggag
 361 accccagcc cctgcagggg cggggcctcc ccaccacacc agccctgttc gcgctctcgg
 421 cagtgccggg gggcgccgcc tcccccatgc cgccctccgg gctgcggctg ctgctgctgc
 481 tgctaccgct gctgtggcta ctggtgctga cgcctggccg gccggccgcg ggactatcca
 541 cctgcaagac tatcgacatg gagctggtga agcggaagcg catcgaggcc atccgcggcc
 601 agatcctgtc caagctgcgg ctcgccagcc ccccgagcca gggggaggtg ccgcccggcc
 661 cgctgcccga ggccgtgctc gccctgtaca acagcacccg cgaccgggtg gccggggaga
 721 gtgcagaacc ggagcccgag cctgaggccg actactacgc caaggaggtc acccgcgtgc
 781 taatggtgga aacccacaac gaaatctatg acaagttcaa gcagagtaca cacagcatat
 841 atatgttctt caacacatca gagctccgag aagcggtacc tgaacccgtg ttgctctccc
 901 gggcagagct gcgtctgctg aggctcaagt taaaagtgga gcagcacgtg gagctgtacc
 961 agaaatacag caacaattcc tggcgatacc tcagcaaccg gctgctggca cccagcgact
1021 cgccagagtg gttatctttt gatgtcaccg gagttgtgcg gcagtggttg agccgtggag
1081 gggaaattga gggctttcgc cttagcgccc actgctcctg tgacagcagg gataacacac
1141 tgcaagtgga catcaacggg ttcactaccg gccgccgagg tgacctggcc accattcatg
1201 gcatgaaccg gcctttcctg cttctcatgg cacccccgct ggagagggcc cagcatctgc
1261 aaagctcccg gcaccgccga gccctggaca ccaactattg cttcagctcc acggagaaga
1321 actgctgcgt gcggcagctg tacattgact ccgcaagga cctcggctgg aagtggatcc
1381 acgagcccaa gggctaccat gccaacttct gcctcgggcc ctgcccctac atttggagcc
1441 tggacacgca gtacagcaag gtcctggccc tgtacaacca gcataacccg gcgcctcgg
1501 cggcgccgtg ctgcgtgccg caggcgctgg agccgctgcc catcgtgtac tacgtgggcc
1561 gcaagcccaa ggtggagcag ctgtccaaca tgatcgtgcg ctcctgcaag tgcagctgag
1621 gtcccgcccc gccccgcccc gccccggcag gcccggcccc accccgcccc gccccgctg
1681 ccttgcccat ggggggctgta tttaaggaca cccgtgccca agcccacctg ggccccatt
1741 aaagatggag agaggactgc gaaaaaaaa aaaaaaaaa
```

*Fig. 19*

SELF-REGULATING DEVICE FOR MODULATING INFLAMMATION

CROSS REFERENCE TO RELATED APPLICATIONS

This application is a divisional application of copending U.S. patent application Ser. No. 13/121,013, filed Mar. 31, 2011, which is a National Stage of International Application No. PCT/US2009/058767, filed Sep. 29, 2009, which in turn claims the benefit of U.S. Provisional Patent Application No. 61/100,845, filed Sep. 29, 2008, each of which is incorporated herein by reference in its entirety.

The Sequence Listing associated with this application is filed in electronic format via EFS-Web and is hereby incorporated by reference into the specification in its entirety. The name of the text file containing the Sequence Listing is 144307_ST25.txt. The size of the text file is 15,641 bytes, and the text file was created on Jun. 3, 2014.

A device is described for an extracorporeal bioreactor comprising cells selected for their ability to produce cytokines and/or cytokine inhibitors for controlling inflammation in a patient.

One current goal of medicine is to facilitate the intrinsic self-renewing ability by relieving damaged tissues from their functional burden and facilitating tissue healing. In order to achieve this goal, it is necessary to acknowledge, understand, and control acute inflammation. We have developed mathematical models of inflammation that inter-related inflammation and tissue damage/dysfunction. Our therapeutic goal is not to abolish inflammation per se but to reduce damage/dysfunction (i.e. promote healing) by modulating inflammation in a rational fashion based on these computational models.

To do so, a self-regulating device and related methods are described herein for individualized regulation of inflammation. The basic concept of the proposed device is to create negative feedback proportional to the exact degree of inflammatory stimulus. More precisely, several inflammatory mediators known as cytokines (protein hormones that induce, modulate, and augment inflammation) are in turn regulated by endogenous inhibitors. In the proposed device, the device would produce or release one or more units of the neutralizing protein for every one or more unit of a given inflammatory cytokine. The device would be a biohybrid device, in which gene-modified cells are housed in a bioreactor or matrix. The genetic modification(s) of the cells housed in this device would serve to 1) sense the levels of a given inflammatory cytokine or cytokines; 2) produce the appropriate levels of the appropriate cytokine inhibitor(s); and 3) possibly also release diagnostic markers that would serve to either delineate the degree of inflammatory cytokines produced by the patient, to delineate the degree of production of the cytokine inhibitor(s), or both (i.e. a "theranostic" device). These genetic modifications could also include other diagnostic, cytotoxic, or therapeutic proteins stimulated by the genetic elements that would sense the presence of inflammatory cytokines in the patient. This device will, in theory, solve the current need for a personalized (yet standardized) inflammation-modulating therapy. The device will be standardized since, for a given disease, a single bioreactor or release matrix would be used. The device would be personalized since a given patient's individual production of cytokines (i.e. the quality and quantity of overall cytokine production) would be counteracted in a precise fashion and only as required and guided by the mathematical model of a given inflammatory disease. Moreover, this device would both obviate the need for a diagnostic method prior to determination of treatment of a given inflammatory disease, since the device would essentially serve as a diagnostic through either the genetic elements that would sense the levels of relevant inflammatory cytokines in the patient, or through the production of indicator proteins at levels proportional to the inflammatory cytokines produced by the patient. Finally, since this device would greatly reduce the time from diagnosis (including possibly the calibration of patient-specific computational simulations of an inflammatory disease) to treatment, since both diagnosis and treatment would be carried by the device in a simultaneous fashion. The reduction in time to treatment is especially important in inflammatory settings such as sepsis, trauma, traumatic brain injury, and wound healing, in which individual trajectories (e.g. length of stay in the hospital) and outcomes (e.g. survival, death, or long-term scarring) may be determined after a short period of inflammation.

The device described herein could be used to modulate inflammation in, for example: 1) acute, systemic inflammatory diseases (e.g. sepsis, trauma); 2) chronic, systemic inflammatory diseases (e.g. rheumatoid arthritis); and 3) cancer with an inflammatory etiology. The device could also be used to reprogram inflammation in a local context (e.g. a skin wound or psoriatic lesion) if interfaced appropriately with such a wound or lesion. The device could be used to influence the early-, mid-, or latestage inflammatory response to any trauma (accidental or iatrogenic [e.g. surgical]) so as to bring about improved healing and rehabilitation. The device could serve solely as a therapeutic device, solely as a diagnostic device, or both. The device could be fine-tuned to each of these applications based on specifications for optimal outcome given by mathematical and other computer simulations of the interrelated inflammatory and damage/healing responses. This device could be used both in civilian and military settings. It could be applied rapidly to start monitoring and/or modulating inflammation in a personalized fashion, or could be applied at any point in time of the inflammatory response if its properties are tuned properly.

Current inflammation therapy can only be individualized to a small extent, given that FDA approval requires that a device or drug be utilized in a standard fashion. This device would be 1) a standardized device that would not require harvesting and culturing of a patient's cells, and yet 2) personalized, in that it would elaborate molecules that specifically neutralize only those inflammatory agents made by a given patient, and at levels driven by the levels of these inflammatory agents in each patient. This device would obviate the need for a time-consuming and expensive cycle of blood sampling, analysis of inflammation biomarkers, calibration of patient-specific mathematical models of inflammation, determination of individual-specific therapy, and implementation of that therapy. Instead, the device's general operating characteristics would be tuned to a given disease by a generalized model, for example a mathematical model, of the disease (based on population data), and yet the specific degree of elaboration of molecules that antagonize each inflammatory agent would be driven by the characteristics of a given patient. Thus, the device would offer the benefit of personalized, rational inflammatory modulation that would take much less time and resources to implement.

In its most general form, the device comprises a bioreactor seeded with cells, such as hepatocytes, genetically engineered to respond to a cytokine with that cytokine's own inhibitor. An additional benefit is that many different types of such genetically engineered cells could be made and stored indefinitely in liquid nitrogen. The stored cells could be thawed and combined in the proportions prescribed by a computational model of a given inflammatory disease, such as a mathematical model described by ordinary or partial differential equations or an agent-based model. Thus, another benefit of this device would be the theoretical capability of a nearly infinite spectrum of operating characteristics. Various embodiments of such a device could be conceived, including reservoirs or biomaterials sensitive to a given cytokine that release the inhibitor, implantation of cells genetically modified to express the inhibitor upon exposure to the cytokine, or bioreactors seeded with these genetically modified cells.

One exemplary procedure for creating and using the bioreactor version of this device is:

Utilize mathematical models of inflammation in a given systemic inflammatory disease to determine the optimal modulation of inflammation that would result in reduced tissue damage/dysfunction. See, e.g., United States Patent Publication Nos. 20030087285 and 20080228456 for examples of modeling methods for, e.g., sepsis, wound healing, vocal fold damage, and, generally inflammation using both object-oriented (agent-based) and equation-based modeling. Currently, factors that enhance damage/dysfunction in our existing mathematical models of inflammation include circulating cytokines that activate macrophage, neutrophils, and TH1 cells (e.g. TNF, IL-6, IL-12, IFN-λ, IL-2) as well as effector products such as nitric oxide, superoxide, and peroxynitrite. A computerized algorithm can search the parameter space of the mathematical model of acute inflammation, in order to determine what changes to the circulating cytokines characteristic of the inflamed state (in which damage/dysfunction is high) will result in reducing damage/dysfunction to levels characteristic of health.

Recombinant DNA constructs are made that consist of a promoter region sensitive to a given cytokine and that cytokines endogenous inhibitor, based on the predictions of the mathematical model in Step 1. Examples include: 1) tumor necrosis factor (TNF) and its endogenous inhibitor, soluble TNF receptor, 2) interleukin-1 (IL-1) and IL-1 receptor antagonist, 3) transforming growth factor-β1 (TGF-β1) and TGF-β1 latency-associated peptide (LAP). Many additional examples also exist. The device could be tuned for more rapid or slower response to cytokines by incorporating multiple copies of a given promoter element, or by using promoter elements of various inherent sensitivities to cytokines. The device could be tuned for various degrees of suppression of a given cytokine by incorporating multiple copies of the gene for the cytokines endogenous neutralizer.

Stable transfection in cells such as a hepatocyte cell line, hepatocytes, or other suitable cells, are made with the gene constructs described in Step 2. This step may take place by first creating viruses that contain the DNA constructs and subsequently infecting the cells described above, or by means of stable transfection methods. The cell lines could be of human or non-human origin, although the likeliest embodiment would utilize human cells in order to reduce the likelihood of immune reactions to nonhuman proteins.

The transfected cells are seeded into vessels that allow for nutrients, oxygen, etc. to be delivered to the cells in order to maintain their viability. Bioreactors containing hepatocytes have been maintained stably for a month or more.

The device is connected to a patient's circulation via, e.g., catheters. Alternatively, the device is connected in some fashion to a skin wound or other local site of inflammation.

Blood or another relevant bodily fluid from the patient is circulated through the device. Inflammatory cytokines in the patient's bodily fluid would stimulate the release of the cytokine-specific neutralizing proteins, with a rate and magnitude driven both by the device's characteristics and the patient's own characteristics of inflammation. With time, lower levels of the patient's inflammatory cytokines would be made as the device's inflammation dampening process proceeds. As this happens, less of the neutralizing proteins would be made, since the stimulus for their production would be lower. During this process, small samples of the inflow and outflow from the device could be removed for analysis of cytokines and comparison to the predictions of the mathematical model, to determine that the device is operating as predicted and that this operation is predicted to result in reduced damage. Alternatively, if the device is constructed so as to allow for the direct or indirect detection of either the patient's inflammatory cytokines or of the inhibitor(s) produced by the bioreactor, then diagnosis could be carried in this manner. Other blood parameters (e.g. liver transferases, bilirubin, etc.) could also be measured as adjunct measures of the function of the device and the patient's health status. Eventually, an inflammatory steady state compatible with improved outcome would be reached. The device may then be either disconnected or replaced with another, similar device that modulates a related or subsequent inflammatory process, or a device that modulates a known co-morbidity or consequence of the inflammatory response (e.g. cancer).

As mentioned above, we have developed a series of mathematical models of inflammation and its interactions with tissue damage and healing, with the goal of understanding, predicting, and controlling inflammation (Kumar, R., et al., J. Theoretical Biol. 230, 145-155 (2004); Clermont, G. et al. Crit. Care Med. 32, 2061-2070 (2004); Chow, C. C. et al. Shock 24, 74-84 (2005); Reynolds, A. et al. J. Theor. Biol. 242, 220-236 (2006); Day, J. et al. J. Theor. Biol. 242, 237-256 (2006); Prince, J. M. et al. Mol. Med. 12, 88-96 (2006); Lagoa, C. E. et al. Shock 26, 592-600 (2006); Constantine, G., et al. J. Pure Appl. Math. doi:10.1007/s10589-007-9118-9, (2007); and Upperman, J. S. et al. J. Pediatr. Surg. 42, 445-453 (2007); Li, N. Y. K., et al. PLoS ONE. 2008. 3:e2789; and Torres, A. et al. Shock. 2009. 32:172-178). The Translational Systems Biology models we have developed to date (An, G.; et al. J. Burn Care Res. 2008. 29:277-2; Vodovotz, Y., et al. PLoS Comput. Biol. 2008. 4:1-6; and Vodovotz, Y. et al. Math. Biosci. 2009.217: 1-10) have been based on multi-scale inter actions at the cell-tissue-organ-organism level and clinical trial simulations at the population level, constructing both equation-based and agent-based models of various degrees of granularity. These innovative models encompass the dynamics of relevant cells, cytokines, and the resulting global tissue dysfunction in order to begin to unravel these inflammatory interactions. "Global tissue damage/dysfunction" is conceptually equivalent to "alarm/danger signals" released from stressed or necrotic cells, and serves as a proxy for the overall health of the organism. Our published models describe and predict various features of septic shock (Redd, M. J., et al. Philos. Trans. R. Soc. Lond B Biol. Sci. 359, 777-784 (2004); Kumar, R., et al., J. Theoretical Biol. 230, 145-155 (2004); Clermont, G. et al. Crit. Care Med. 32, 2061-2070 (2004); Chow, C. C. et al. Shock 24, 74-84 (2005); and Constantine, G., et al. J. Pure Appl. Math. doi:10.1007/s10589-007-9118-9, (2007)) and trauma/hemorrhage (Kumar, R., et al., J. Theoretical Biol. 230, 145-155 (2004); Reynolds, A. et al. J. Theor. Biol. 242, 220-236 (2006); and Day, J. et al. J. Theor. Biol. 242, 237-256 (2006)), including the simulation of anti-inflammatory strategies in clinical trials (Clermont, G., et al. Crit. Care Med. 2004. 32:2061-2070; Mi, Q. et al. Wound Rep. Reg. 2007. 15:671-682; Kumar, R. et al. Shock. 2008. 29:104111. and An, G., et al. J. Crit. Care 22, 169-175 (2007)).

The basic concept of the proposed device is to create negative feedback proportional to the exact degree of inflammatory stimulus. More precisely, for every unit of a given inflammatory cytokine, the device would produce or release essentially one unit of the neutralizing protein. Examples include: 1) tumor necrosis factor (TNF) and its endogenous inhibitor, soluble TNF receptor (An, G. et al. J. Burn Care Res. 29, 277-285 (2008); Gallucci, S. et al. Curr. Opin. Immunol. 13, 114-119 (2001); Vodovotz, Y. Immunologic Res. 36, 237-246 (2006); and Aggarwal, B. B. et al. Ernst. Schering. Res. Found. Workshop 161-186 (2006)); and, 2) interleukin-1 (IL-1) and IL-1 receptor antagonist (Hasegawa, A., et al. Takasaki, W., et al. Mini. Rev. Med. Chem. 1, 5-16 (2001)), 3) transforming growth factor-β1 (TGF-β1) and TGF-β1 latency-associated peptide (LAP, Femandez-Botran, R., et al. Expert. Opin. Biol. Ther. 2, 585-605 (2002) and Böttinger, EP., et al., *Proc. Natl. Acad. Sci. USA* Vol. 93, pp. 5877-5882, June 1996). Many additional examples also exist. Various embodiments of such a bioreactor device could be conceived, including reservoirs or biomaterials sensitive to a given cytokine that release the inhibitor, implantation of cells genetically modified to express the inhibitor upon exposure to the cytokine, or bioreactors seeded with these genetically modified cells (FIG. 1). The proof of concept studies described here would take the latter approach.

Importantly, there must be a rational process by which to tailor the specific characteristics of such a device. For example, the specific cytokines to be antagonized and the timing and magnitude of such manipulation will vary depending on the nature of the inflammatory disease targeted. The mathematical models we have created are therefore useful for the rational construction and utilization of this device.

A bioreactor is therefore provided, for example, comprising a compartment comprising cells comprising a chimeric gene. The chimeric gene comprises a response element operably linked to a sequence encoding a cytokine or an inhibitor of a cytokine, in which the response element causes expression of the cytokine or causes expression of the inhibitor of the cytokine when the cells are contacted with the cytokine. The bioreactor comprising a selectively permeable membrane in contact with the cells. As disclosed herein, the gene can express a cytokine inhibitor of one of TNF, IL-1, TGFβ1 and IL-6, such as TNF receptor, IL-1 receptor agonist, TGF-β1 LAP (latency-associated peptide) and an IL-6Ralpha/gp130 fusion protein.

The selectively permeable membrane can be a selectively-permeable hollow fiber. Alternately, the compartment comprising the cells can comprise a vessel having a selectively permeable wall. The vessel may comprise a plurality of selectively permeable hollow fibers passing through the compartment through which one or both of a gas and a fluid comprising nutrients for the cells can be passed. In another embodiment, the compartment comprising the cells comprises a plurality of selectively permeable hollow fibers passing through the compartment in which the plurality of hollow fibers are fluidly connected to a plasma or blood circulation system in which blood or plasma from the patient can be circulated through the hollow fibers and into a patient.

The cells may be any cell that is effective in its use in the bioreactor, and may be xenogeneic, syngeneic, allogeneic, or autologous cells to a patient treated by use of the bioreactor. In one embodiment, the cells are transfected or transduced hepatocytes or a hepatocyte cell line, such as HepG2. The bioreactor may further comprise a cell comprising a (nucleotide) sequence encoding a fluorescent protein that either is: a) operably linked to the response element and the sequence encoding the cytokine or inhibitor of the cytokine is attached to and in frame with the sequence encoding the fluorescent protein and a self-cleaving polypeptide sequence between the sequence encoding the cytokine or inhibitor of the cytokine and the sequence encoding the fluorescent protein; or b) under control of a second response element (in the cell or a second cell) that causes expression of the fluorescent protein when the cells are contacted with the cytokine. Alternately, one or more of the cytokines or inhibitors of cytokines encoded by the one or more non-native inducible genes comprises a fluorescent tag that is contiguous with the one or more of the cytokines or inhibitors of cytokines.

Also described herein is a method of modulating (controlling, affecting) wound healing, sepsis, trauma, or traumatic brain injury (TBI), comprising, contacting a bodily fluid of a patient with the selectively permeable membrane of the bioreactor of claim 1 such that a cytokine in the bodily fluid can pass through the selectively permeable membrane and a cytokine or cytokine inhibitor produced by the cells can pass into the bodily fluid, and returning the bodily fluid to the patient. The bioreactor may be any bioreactor described herein. The cells, their quantity and chimeric genes they express, may be selected by use of a computer model of an inflammatory response characteristic of a disease or condition in the patient. The method may include modeling inflammation associated with wound healing, sepsis, trauma or TBI and determining one or more cytokines to inhibit or produce to control inflammation in the patient associated with sepsis, wound healing or trauma. In one embodiment, data obtained from a patient may be used to assist in modeling inflammation or in tailoring the treatment to a patient. For example, the method may comprise determining levels of one or more cytokines in the patient and modeling inflammation using the one or more levels of cytokines in the patient and determining a cytokine level to be controlled in the patient to determine a chimeric gene construct to place in the bioreactor based on an outcome of the modeling. The method may comprise determining levels of one or more cytokines in the patient and modeling inflammation using the one or more levels of cytokines in the patient and determining a cytokine level to be controlled in the patient to determine a chimeric gene construct to place in the bioreactor based on an outcome of the modeling. In one embodiment, the patient is a TBI patient, and for example, one or both of an inhibitor of TNF and an inhibitor of IL-6 are produced by the cells. In another embodiment, the cells comprise one or more genes that express an inhibitor of one or both of TNF and IL-1α or IL-1β. In another embodiment, the gene expresses an inhibitor of a cytokine selected from the group consisting of soluble TNF receptor, IL-1 receptor agonist, and TGF-β1 LAP (latency-associated peptide).

In further embodiments, the compartment comprising the cells and comprises a plurality of selectively permeable hollow fibers passing through the compartment in which the plurality of hollow fibers are fluidly connected to a plasma or blood circulation system in which blood or plasma from the patient is circulated through the hollow fibers and into the patient. In another embodiment, the compartment comprising the cells has at least one wall that is the selectively permeable membrane, in which the first side of the membrane is placed in contact with a wound on the patient or a bodily fluid in situ in the patient. In that embodiment, optionally, the compartment comprises a plurality of selectively permeable hollow fibers passing through the compartment through which one or both of a gas and a fluid comprising nutrients for the cells is passed.

Figure 4A:
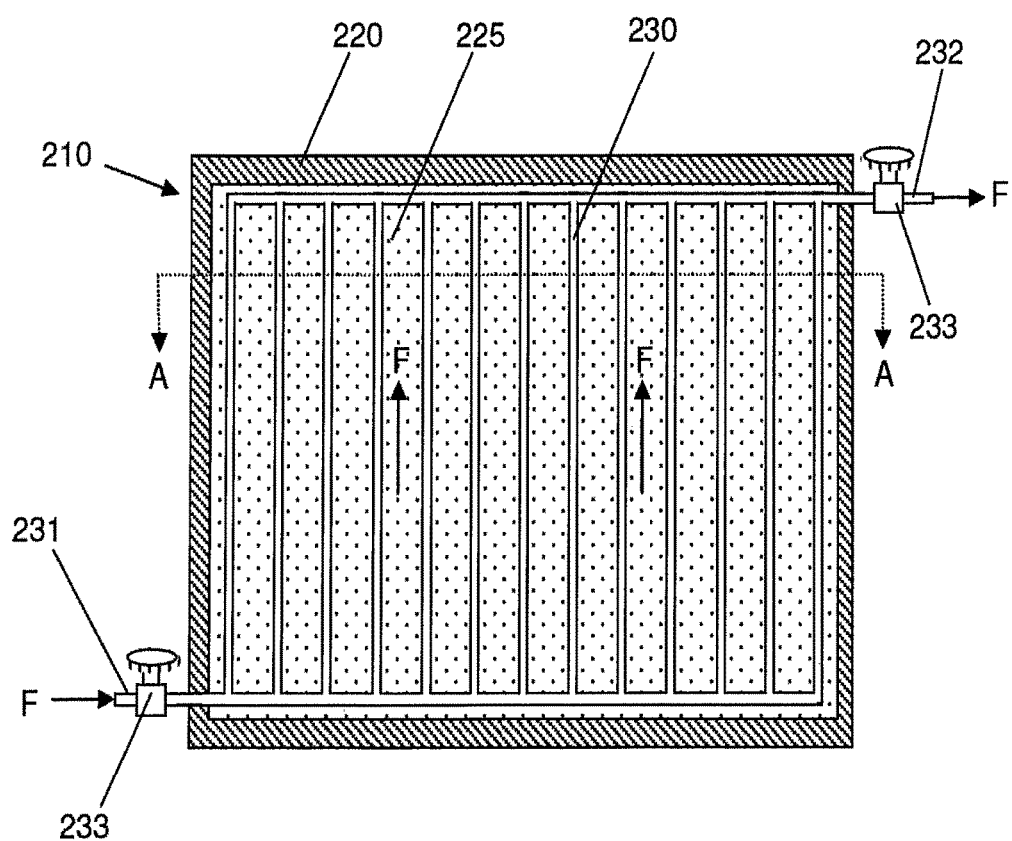
Figure 4B:
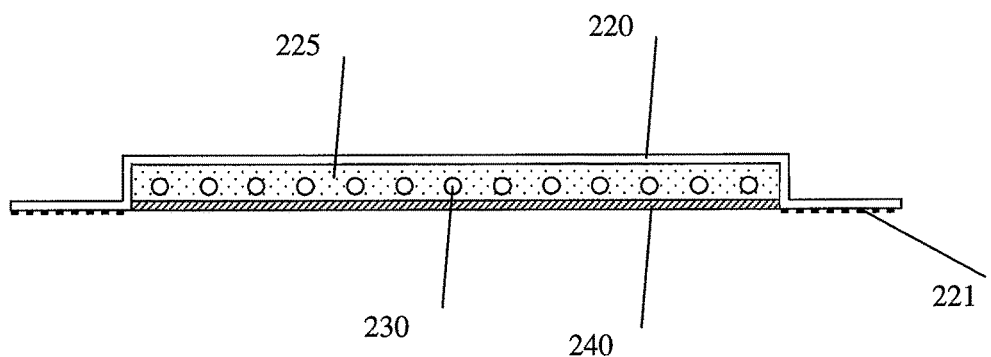
Figure 4C:
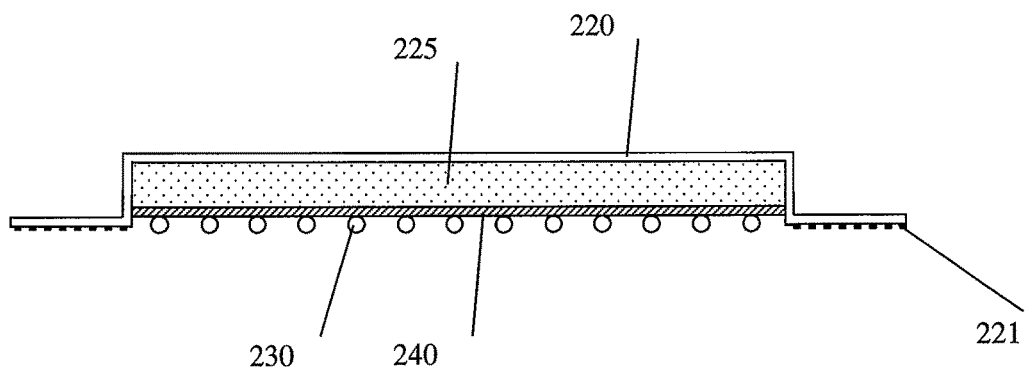
Figure 4D:
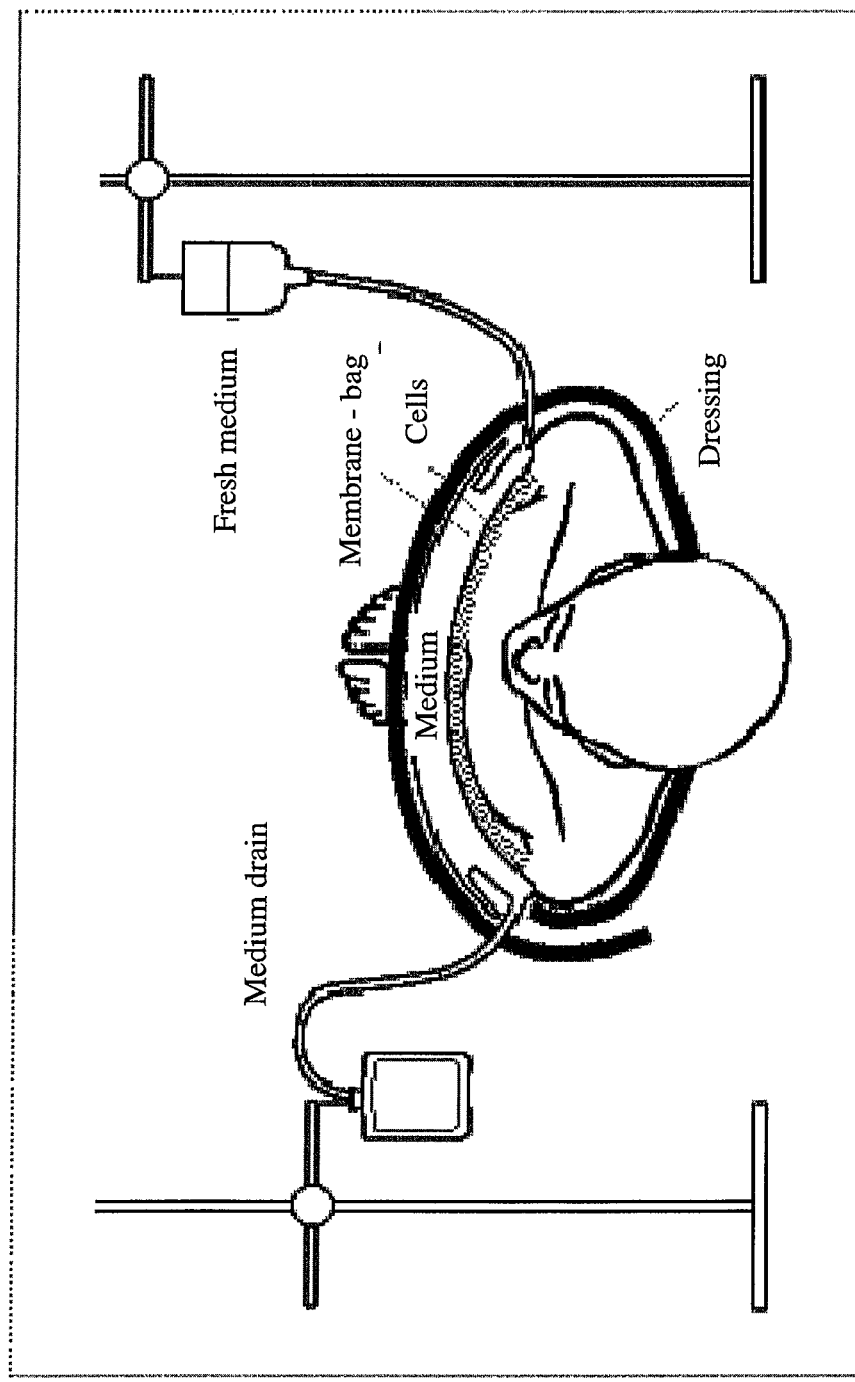

FIG. 4A is a schematic diagram depicting a transdermal-type bioreactor device comprising hollow fibers, as described herein. FIGS. 4B and 4C are cross-sections of two exemplary embodiments of the device of FIG. 4A, along line A. FIG. 4D. Temporary artificial flat sheet membrane "bag" placed on a wound and perfused with medium. Hollow fibers within the bag are not shown.

Figure 5:
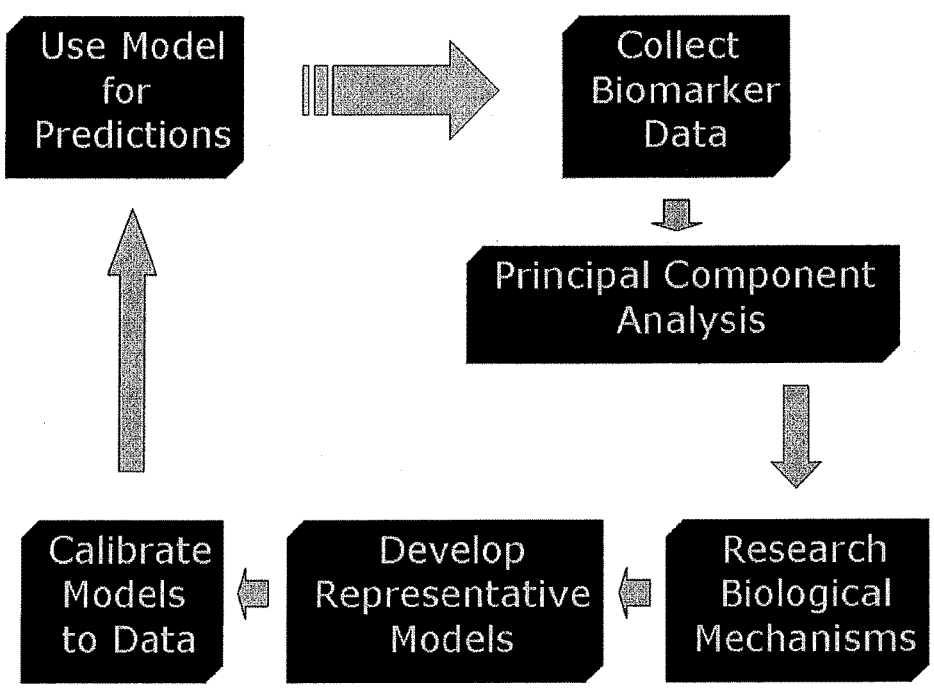

FIG. 5. Iterative process of modeling and experimentation. Initial model components are determined from experimental data using Principal Component Analysis. Subsequently, model building follows an iterative process involving calibration from existing or new data, and validation from prediction of data. This process identifies both areas where a model is correct and where it is deficient relative to data and therefore must be corrected.

Figure 6A:
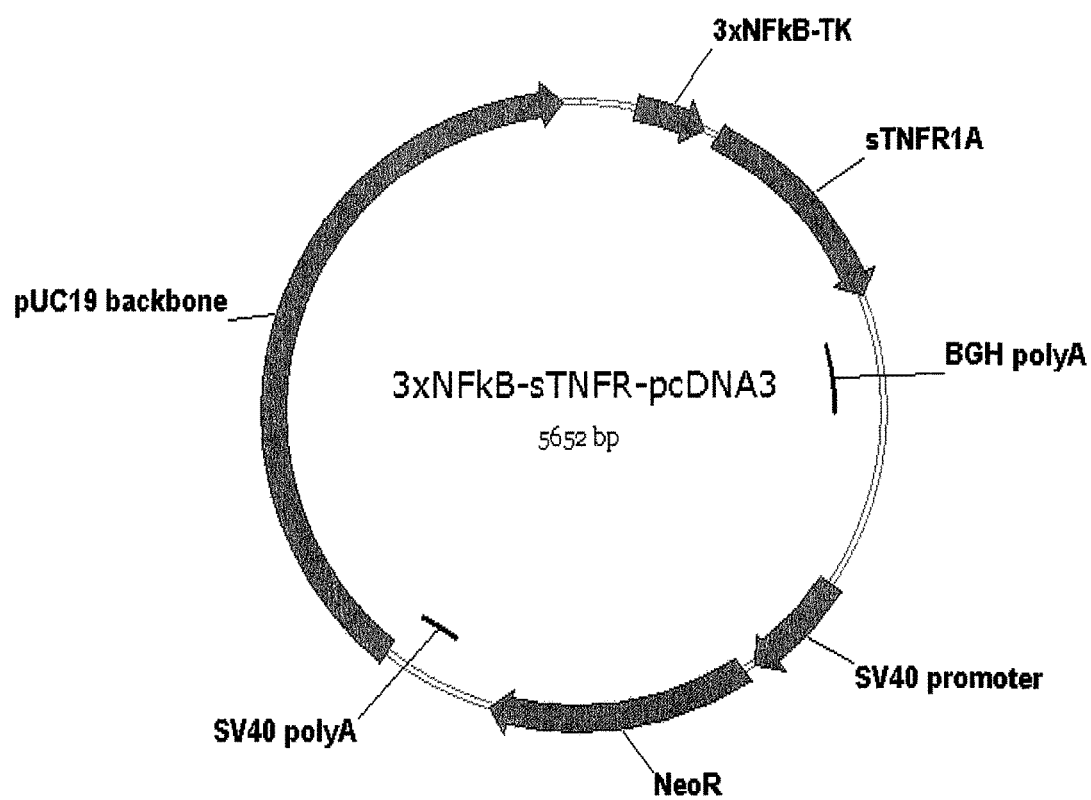

FIGS. 6A and 6B. sTNFR and IL-1ra plasmid. The NF-κB-responsive element and sTNFR gene were obtained as described in the text (shown schematically in FIG. 6A). FIG. 6B shows the results of sequencing of a portion of the plasmid comprising the IL-1ra expressing gene (SEQ ID NO: 1).

Figure 7A:
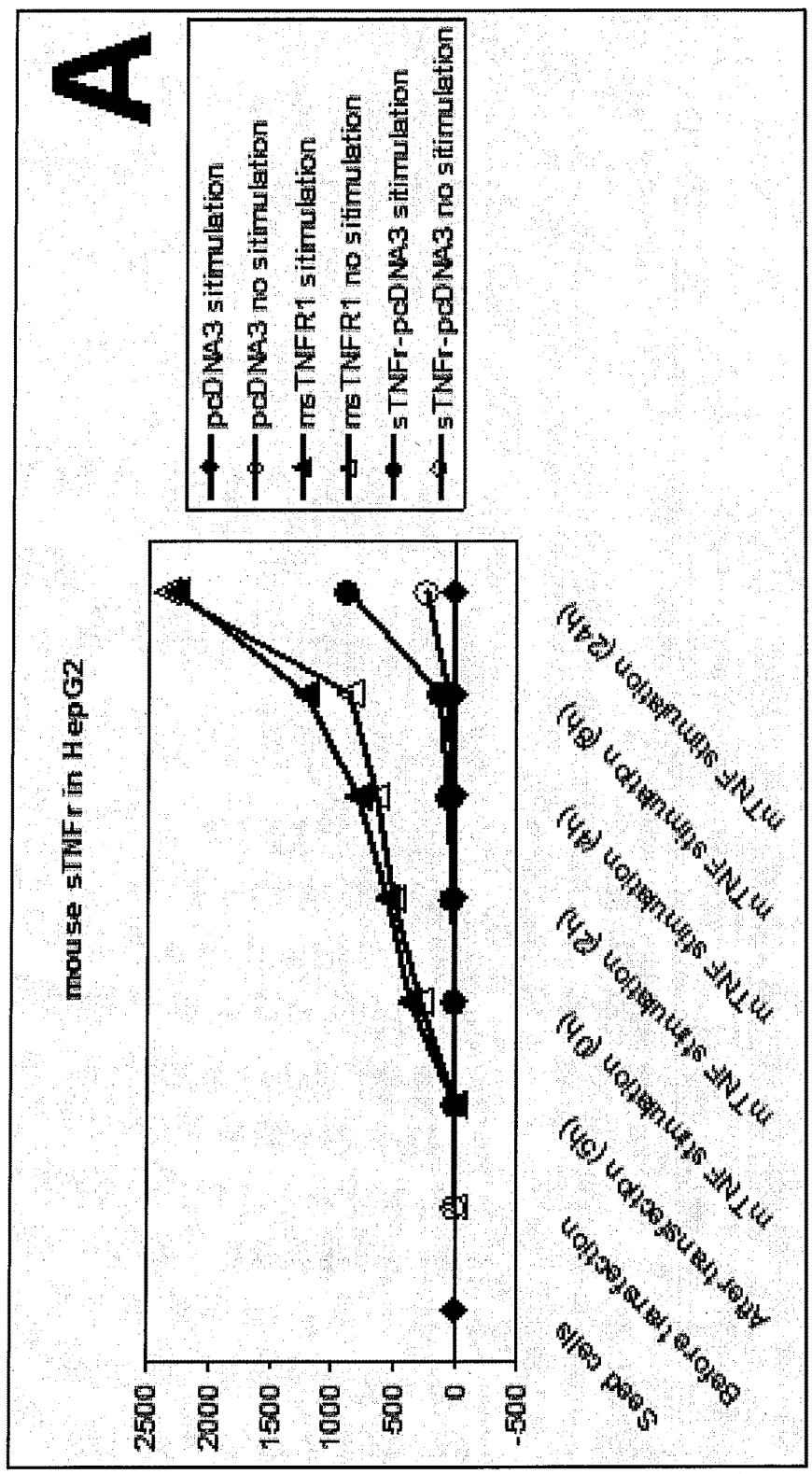
Figure 7B:
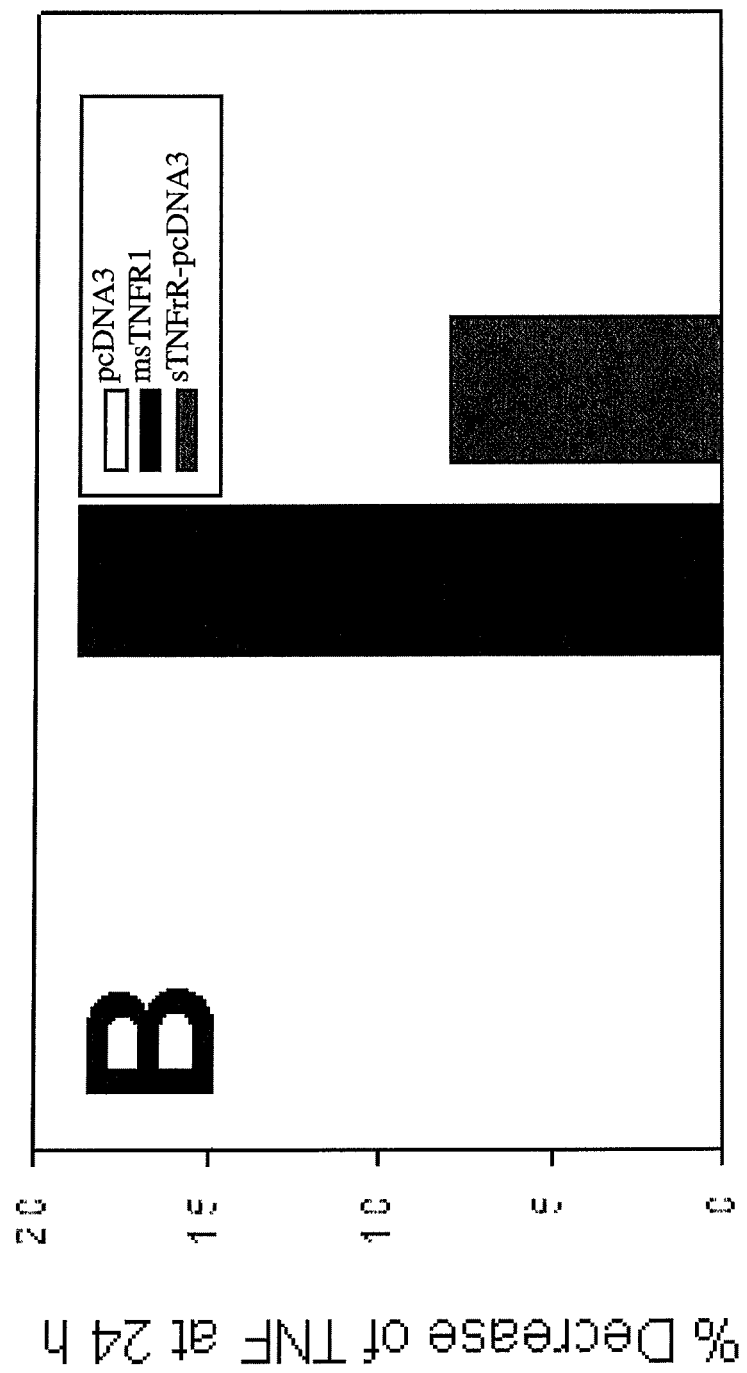

FIGS. 7A and 7B. Initial proof-of-concept experiments. FIG. 7A: HepG2 cells were cultured in standard 2D tissue culture and transfected with negative control plasmids (pcDNA3; negative control), a construct in which the constitutively active CMV promoter drives the expression of sTNFR (msTNFR1; positive control), or the TNF-driven sTNFR promoter (sTNFR1-pcDNA3). In each case, the cells were either unstimulated or stimulated with 10 ng/mL mouse TNF. The graph shows the levels of sTNFR produced under each of these conditions.

Figure 8:
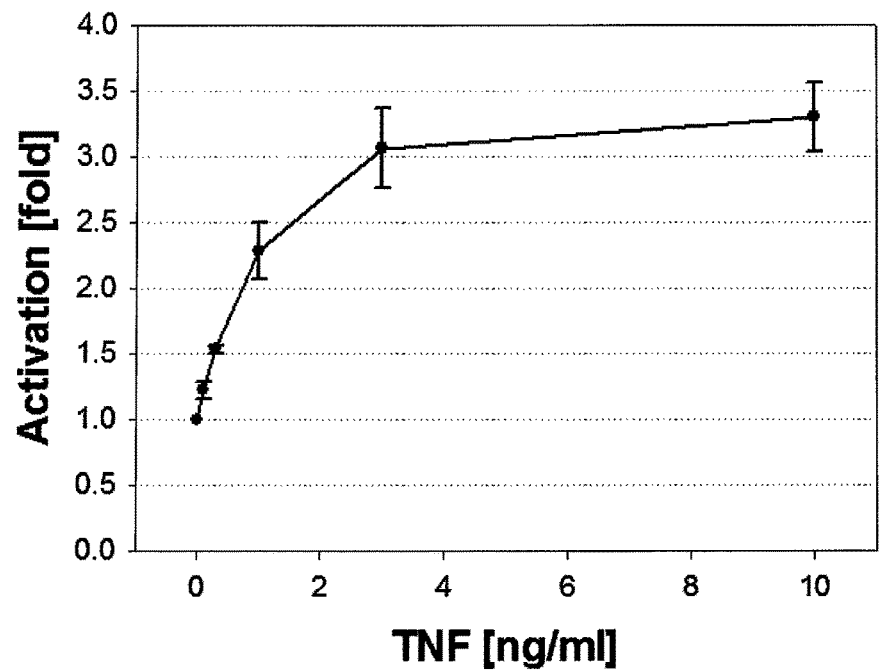

FIG. 8. Dose-dependent activation of sTNFR by TNF in transfected HepG2 cells. HepG2 cells were treated as in FIG. 7, except that escalating doses of mouse TNF were used as a stimulus. All assessments of sTNFR were made 24 h following stimulation with TNF.

Figure 9:
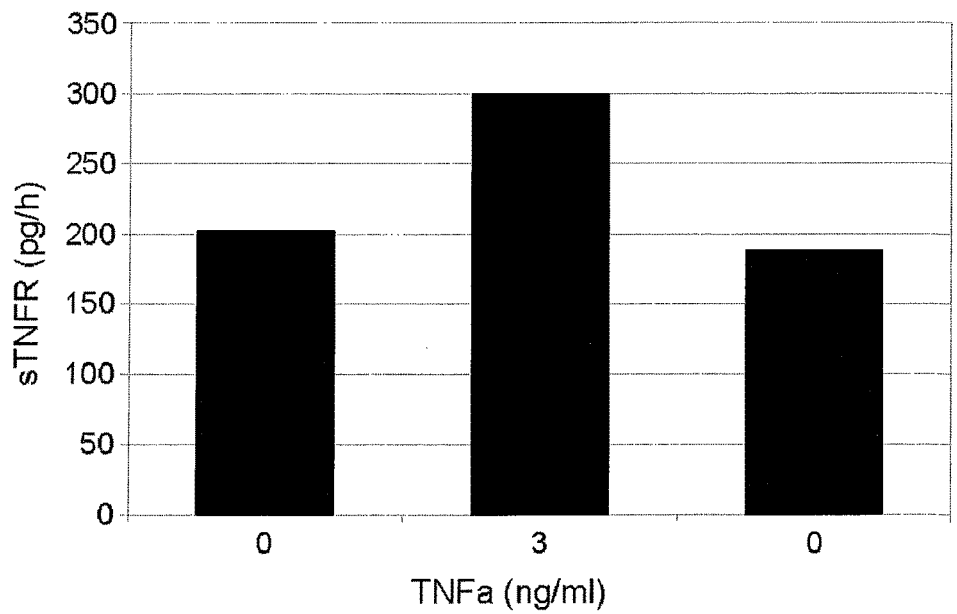

FIG. 9—HepG2 cells transfected with this plasmid were placed in a bioreactor and tested for their response to TNF. Following 3 days of culture (baseline), the cells were stimulated with 3 ng/mL mouse TNF. 24 h later, as well as a further 24 h after washing out the bioreactor with culture medium, mouse sTNFR was assayed as in FIG. 8.

Figure 10:
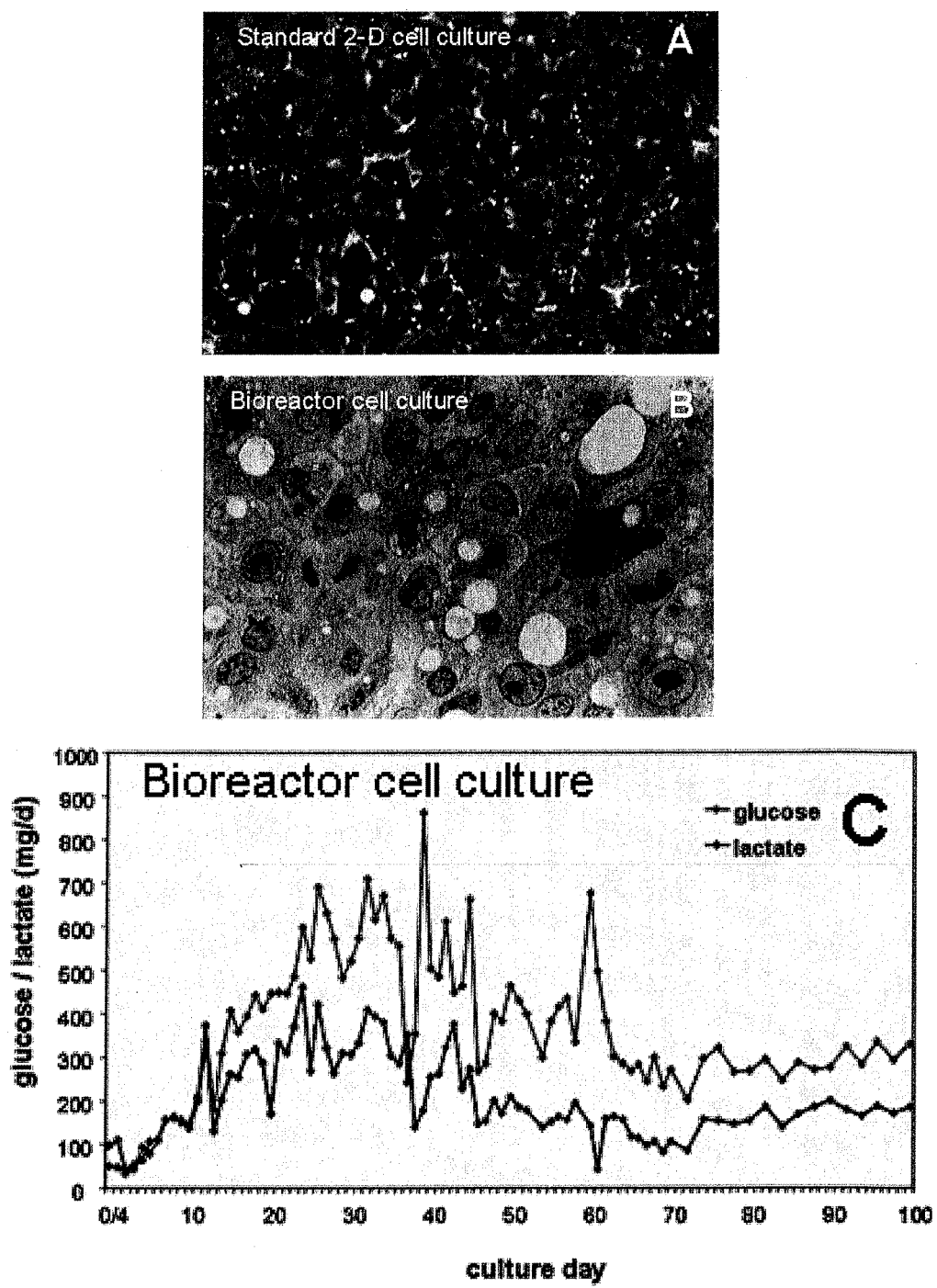

FIG. 10. Characterization of HepG2 cells in 2-D and 3-D culture. HepG2 cells were cultured in standard 2-D tissue culture (Panel A) as well as in experimental-scale liver bioreactors (Panel B); note the similar appearance of the cells. Panel C shows that HepG2 cells can survive and remain metabolically active for up to 100 days in bioreactor culture, producing glucose (red line) and lactate (blue line).

Figure 11:
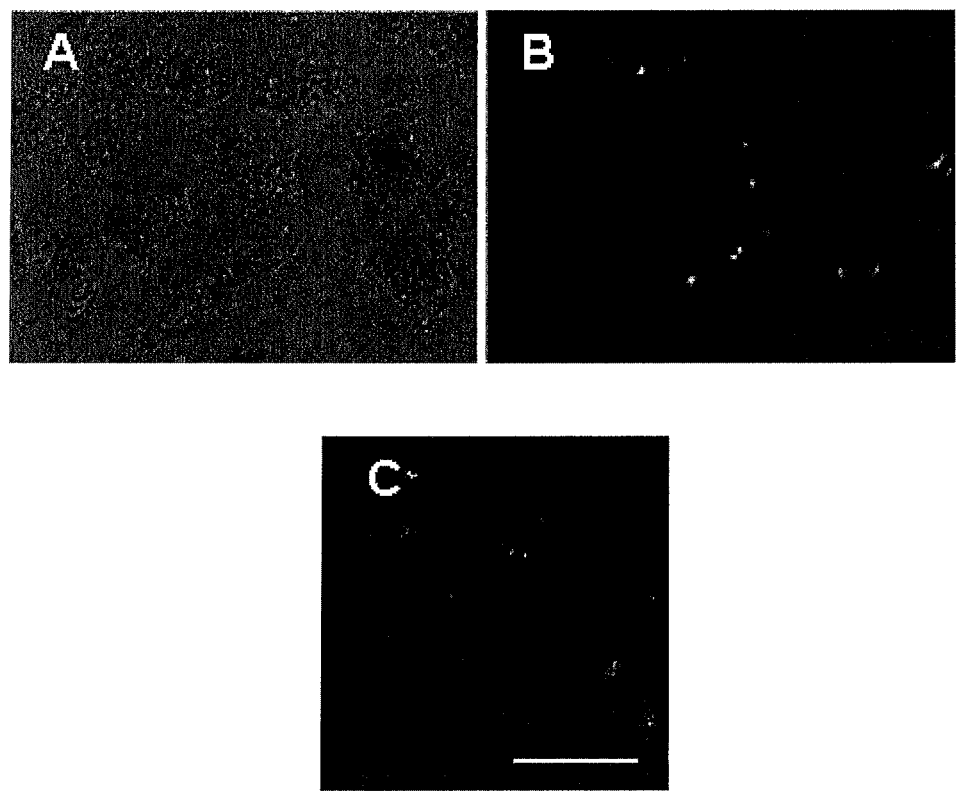

FIG. 11. Detection of fluorescence in transfected HepG2 cells in 2-D and bioreactor cultures. Panel A and B: HepG2 cells were transfected with pTurboFP635N, in which the fluorescent protein is under control of the CMV promoter. Panel A: bright field microscopy. Panel B: fluorescence microscopy. Panel C: Primary human fetal liver cells (~18 weeks gestation) were cultured for 10 days in a 4-well bioreactor. Tissue that had formed was fixed with 4% paraformaldehyde, embedded in paraffin, and sections were stained with DAPI (blue fluorescence) for cell nuclei and for α-fetoprotein (green fluorescence).

Figure 12:
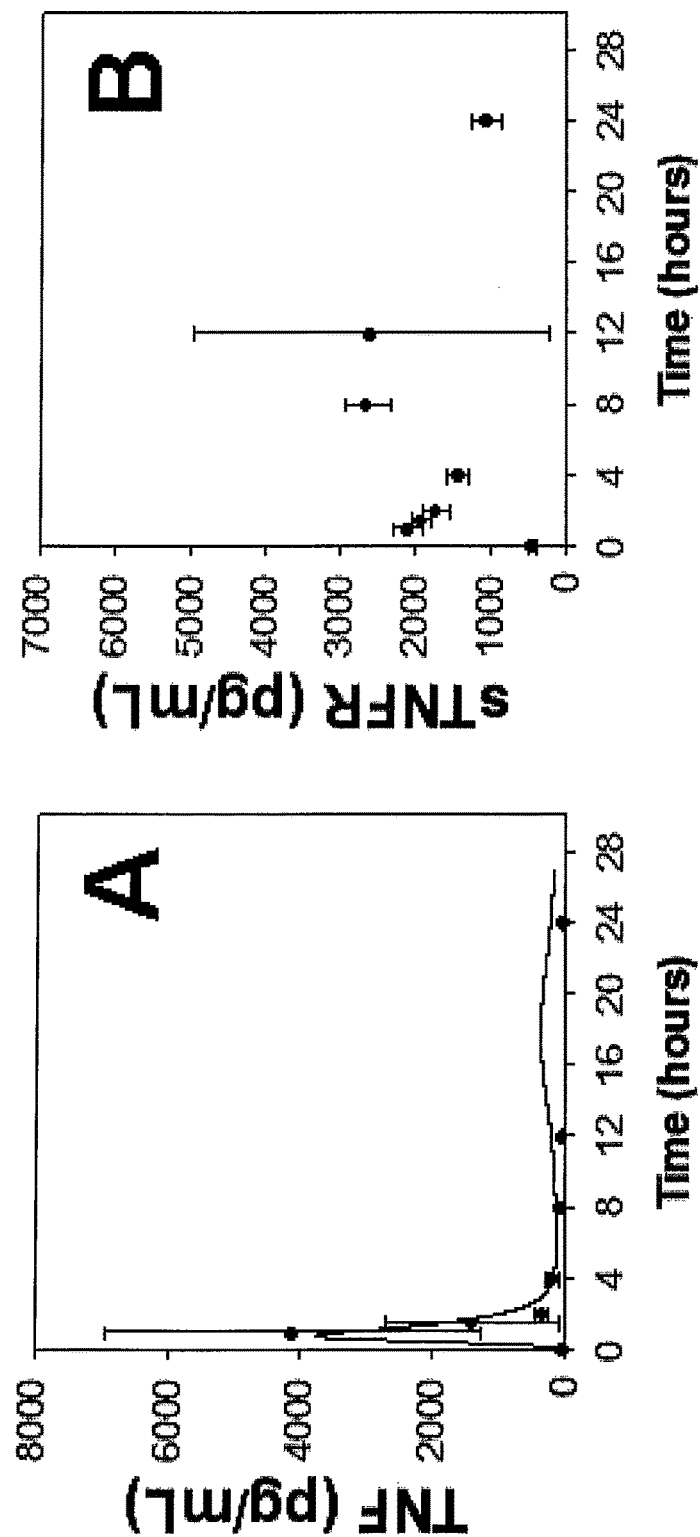

FIG. 12. Expression and modeling of TNF and sTNFR in endotoxemic mice. Studies were carried out on C57Bl/6 mice injected intraperitoneally with 3 mg/kg LPS for the indicated time points. TNF (symbols; Panel A) and sTNFR (symbols; Panel B) were measured in the serum using specific ELISA's. A mathematical model was fit to the data in Panel A. We propose to do the same with data similar to those in Panel B.

Figure 13:
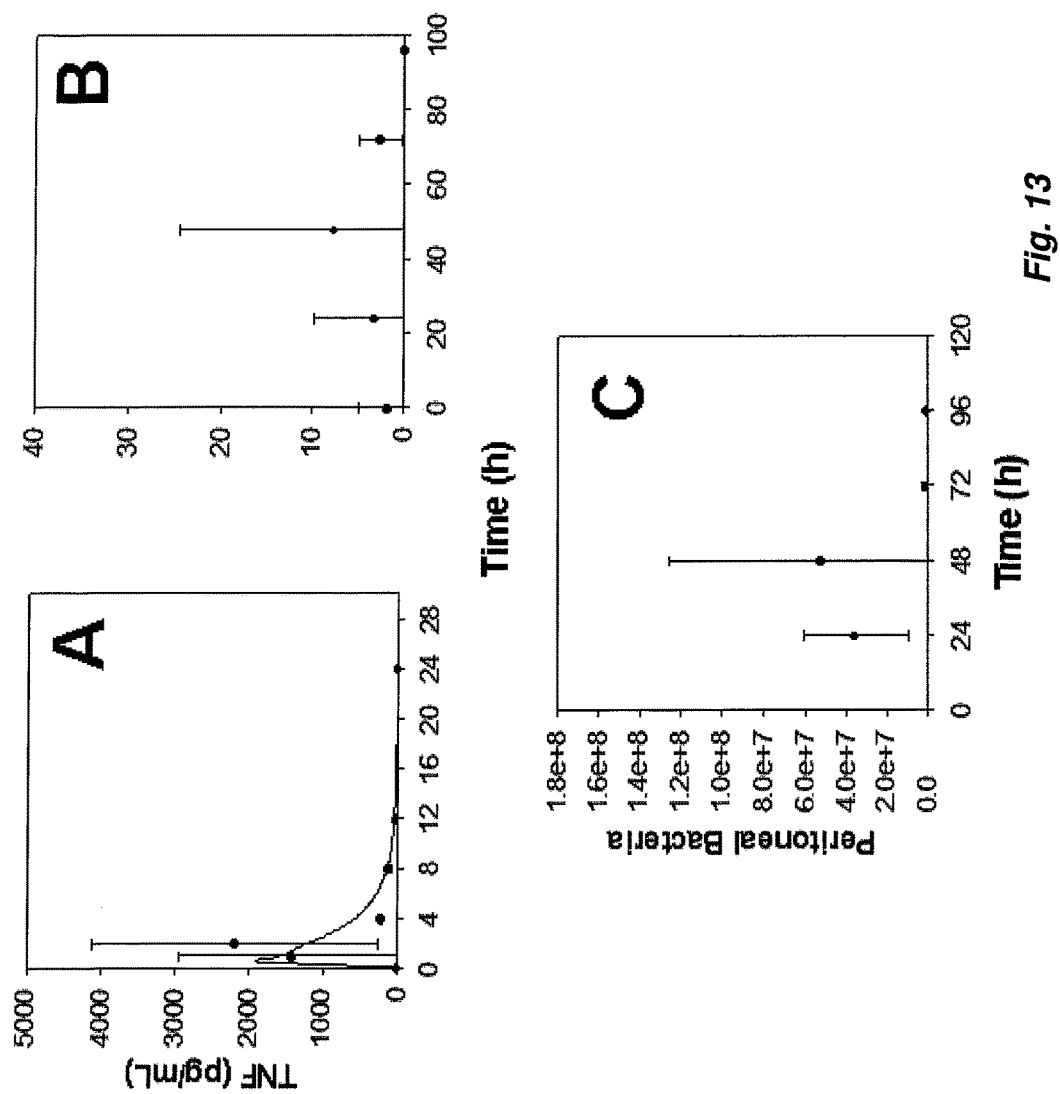

FIG. 13. Endotoxin- and *E. coli-induced* TNF production and bacterial dynamics in rats. Panel A: Rats (n=4 per time point) were injected intraperitoneally with 3 mg/k LPS. The rats were euthanized at the indicated time points and TNF was assayed using a rat-specific ELISA (R&D Systems, Minneapolis, Minn.). Values are mean±SD. The line represents the output of a mathematical model calibrated on these data as well as data on IL-6, IL-10, and NO reaction products ($NO_2^-/NO_3^-$) at this dose of LPS as well as additional stimuli (6 and 12 mg/kg LPS, surgical cannulation trauma, and surgical cannulation+hemorrhagic shock (30 mmHg for multiple time points). Panel B: Rats (n=3-5 per time point) were subjected to surgical implantation of a fibrin clot containing approximately $1.5 \times 10^8$ *E. coli* bacteria (see Ref. 21 for protocol). In this experimental model, approximately 25% of the rats died in the 96-h period of observation. Surviving rats were euthanized at the indicated time points and TNF was assayed as in Panel A. Panel C: peritoneal bacterial counts in the rats of Panel B.

Figure 14A:
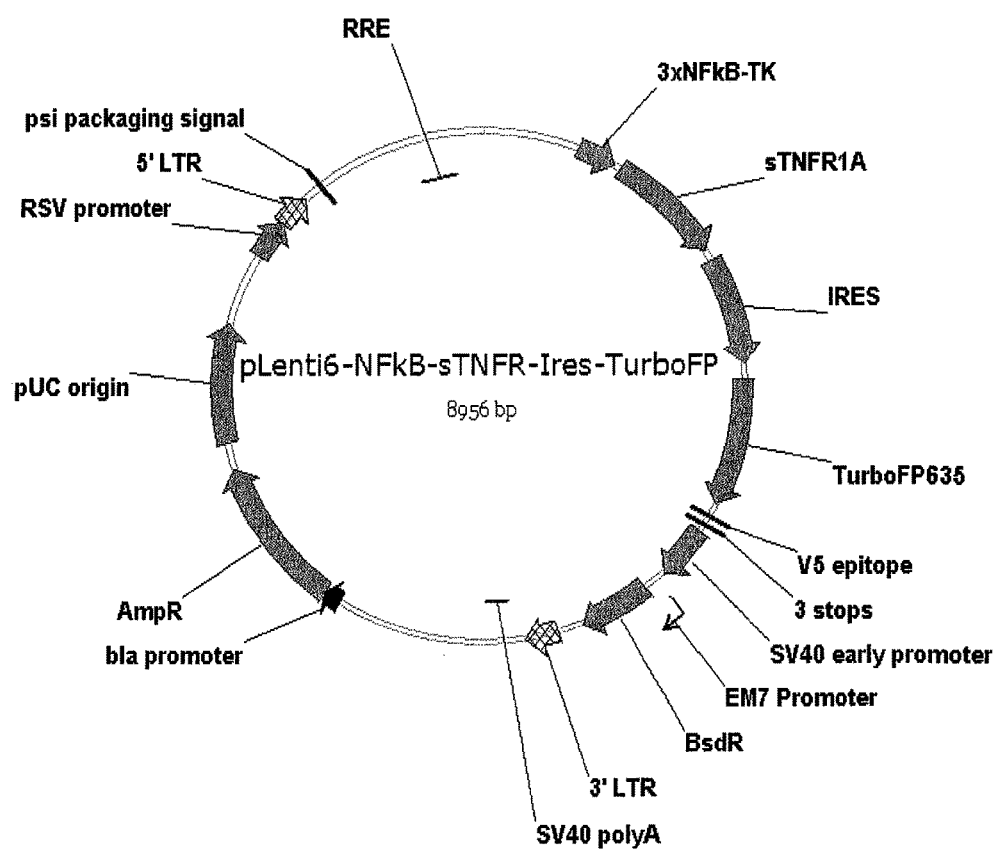

FIG. 14A shows a plasmid map for plasmid pLenti6-3× NFkB-sTNFR-Ires-TurboFP. FIG. 14B shows a partial sequence of the plasmid depicted in FIG. 14A (SEQ ID NO: 2) identifying pertinent elements in that sequence.

Figure 15:
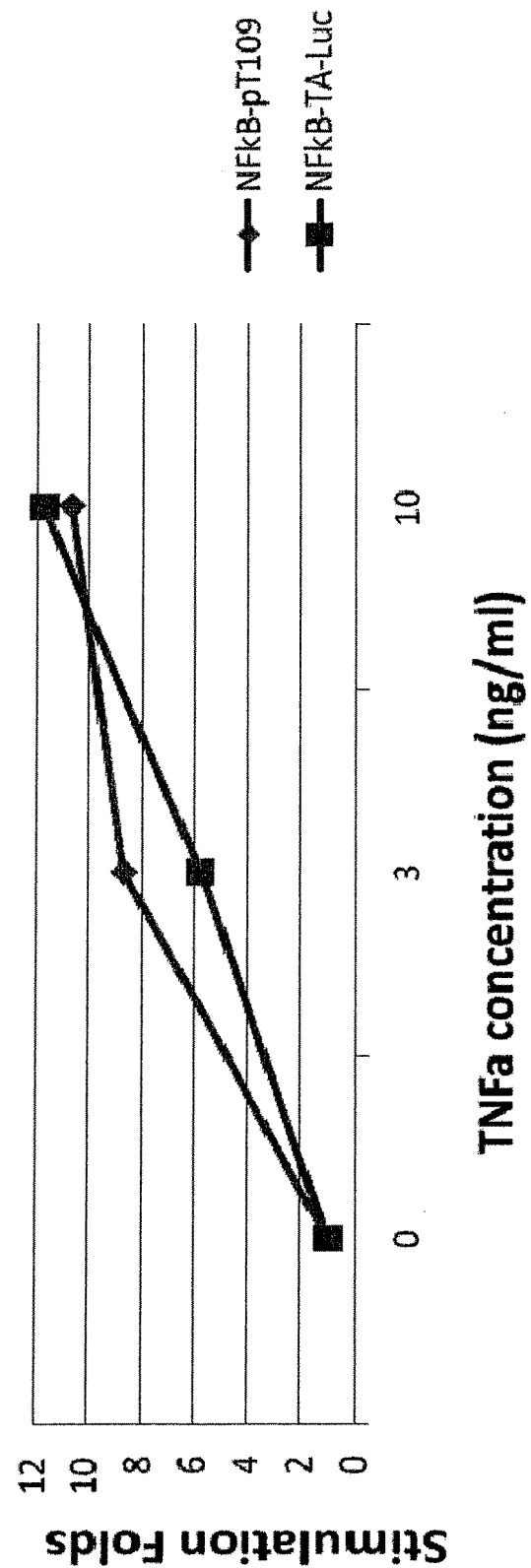

FIG. 15 is a graph showing response of two NF-kB responsive promoters.

Figure 16A:
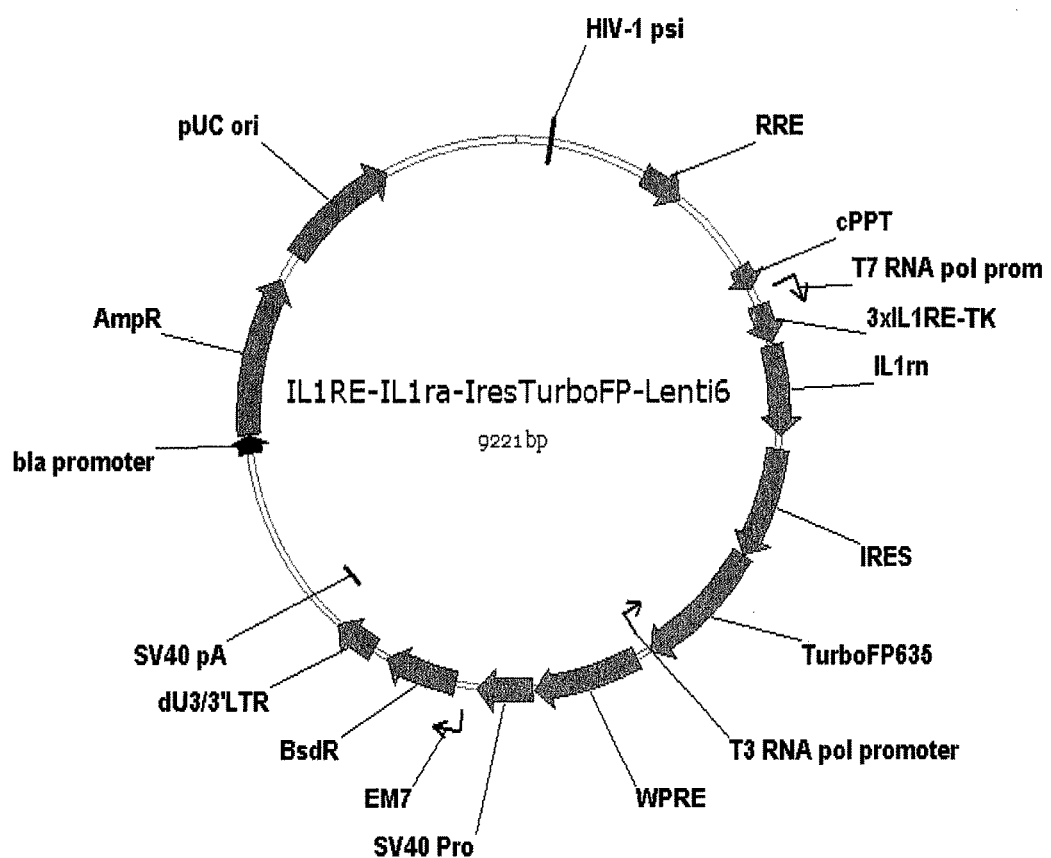

FIG. 16A shows a plasmid map for plasmid IL1RE-IL1ra-IresTurboFP-lenti6.3. FIG. 16B shows apartial sequence of the plasmid depicted in FIG. 16A (SEQ ID NO: 3) identifying pertinent elements in that sequence.

Figure 17A:
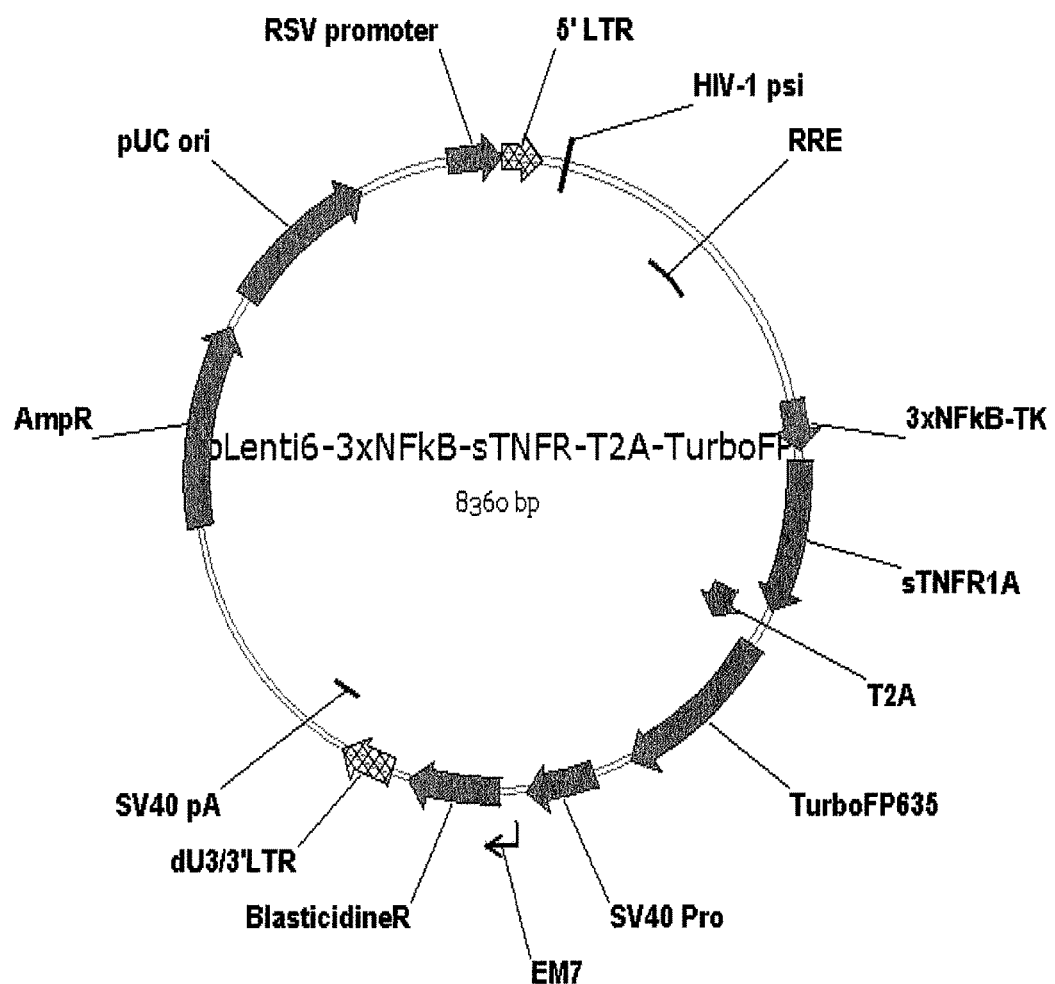

FIG. 17A shows a plasmid map for plasmid pLenti6-3× NFkB-sTNFR-T2A-TurboFP. FIG. 17B shows a partial sequence of the plasmid depicted in FIG. 17A (SEQ ID NO: 4) identifying pertinent elements in that sequence.

Figure 18A:
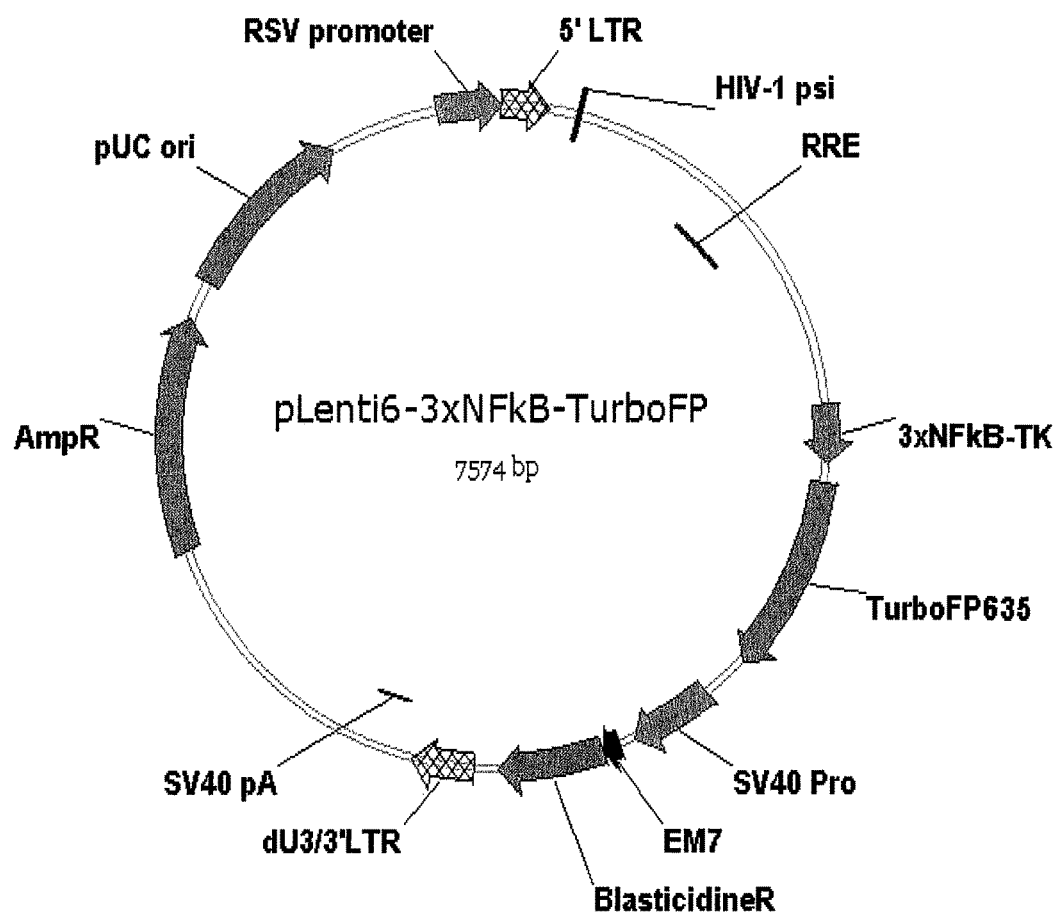

FIG. 18A shows a plasmid map for plasmid pLENTI6-3×NFkB-TurboFP. FIG. 18B shows a partial sequence of the plasmid depicted in FIG. 18A (SEQ ID NO: 5) identifying pertinent elements in that sequence.

FIG. 19 provides an exemplary nucleotide sequence for TGFβ1 LAP (cDNA, GenBank Accession NO. BC000125, SEQ ID NO: 6)

Figure 20:
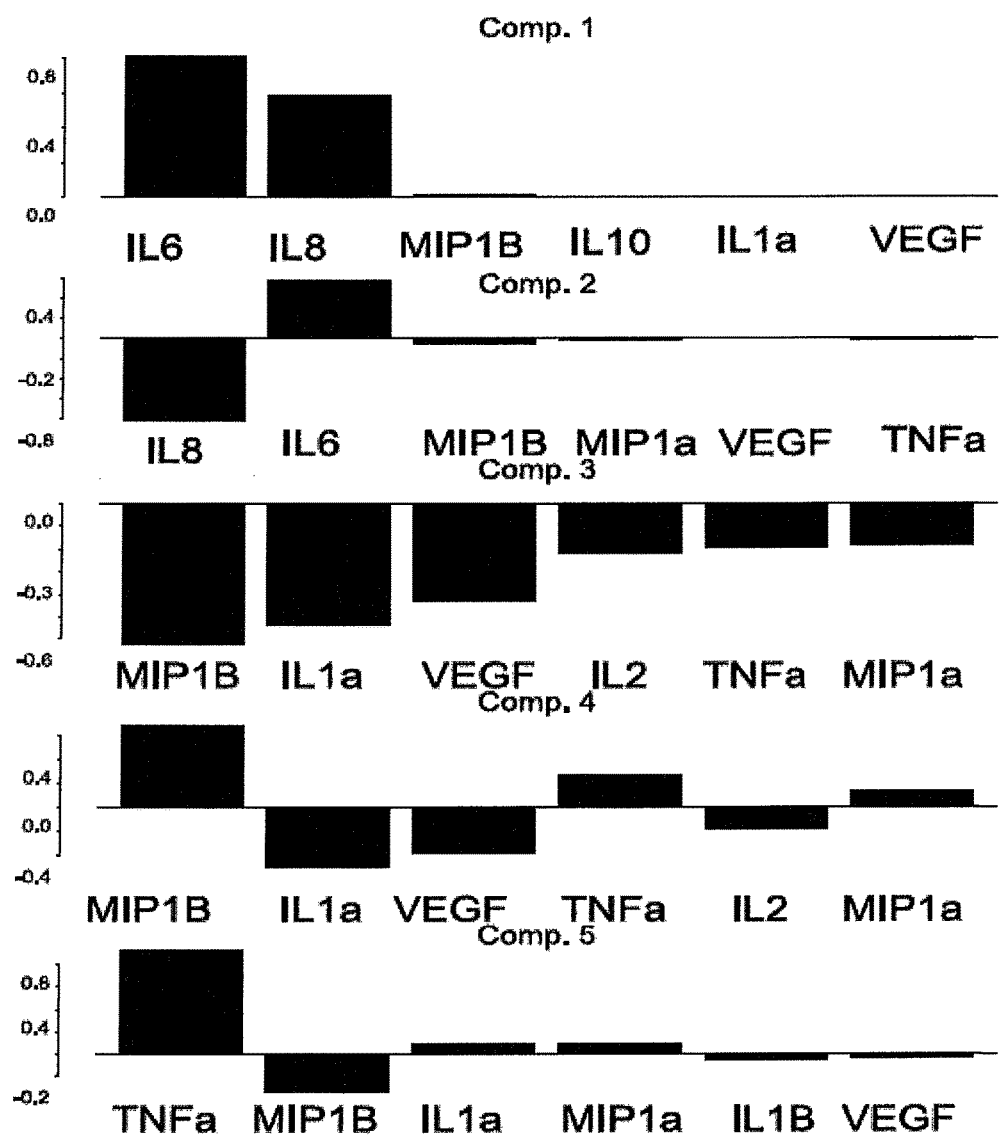

FIG. 20 are graphs showing PCA of data in Traumatic Brain Injury Patients.

Figure 21:
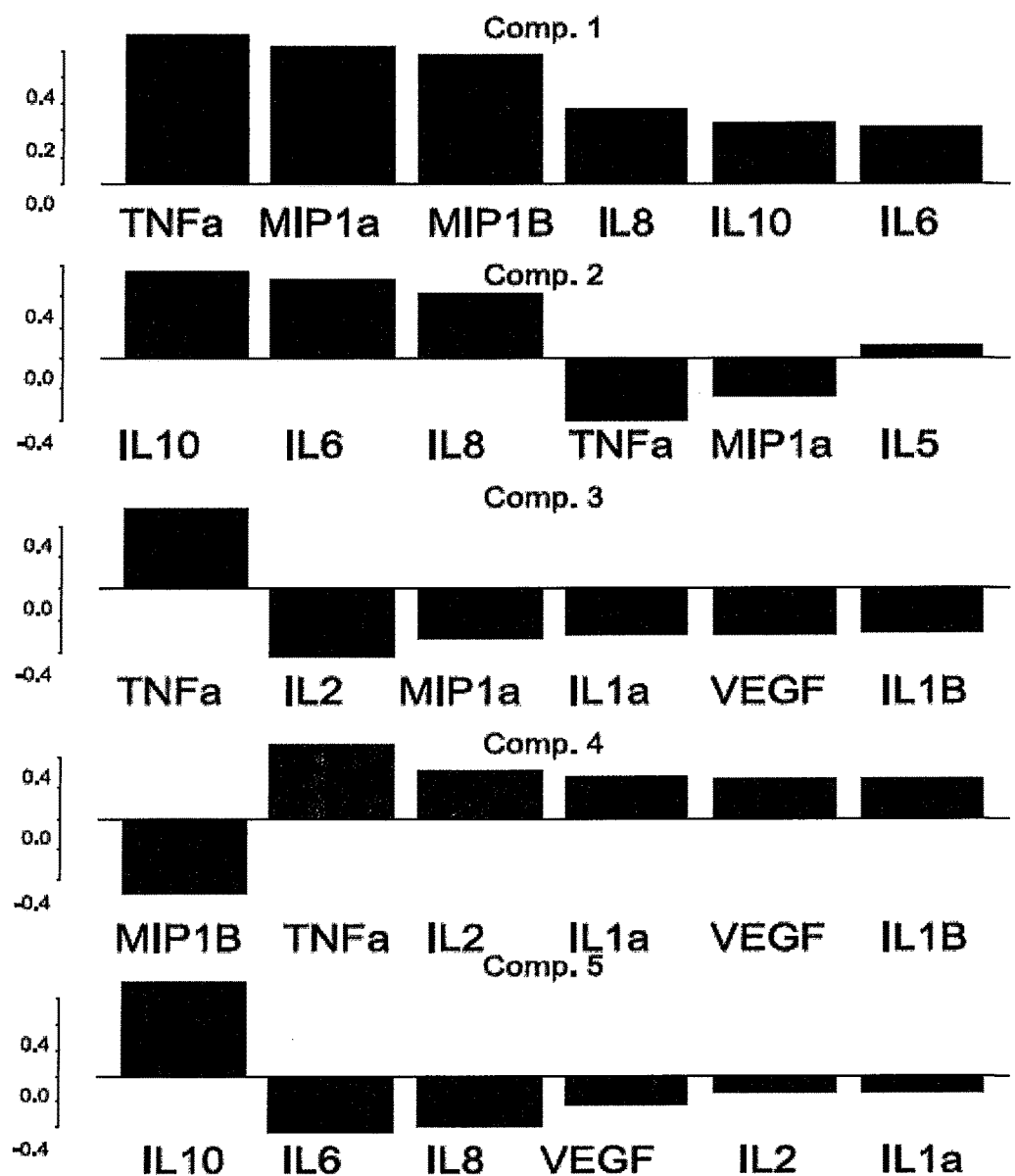

FIG. 21 are graphs showing PCA of normalized data in Traumatic Brain Injury Patients.

Figure 22:
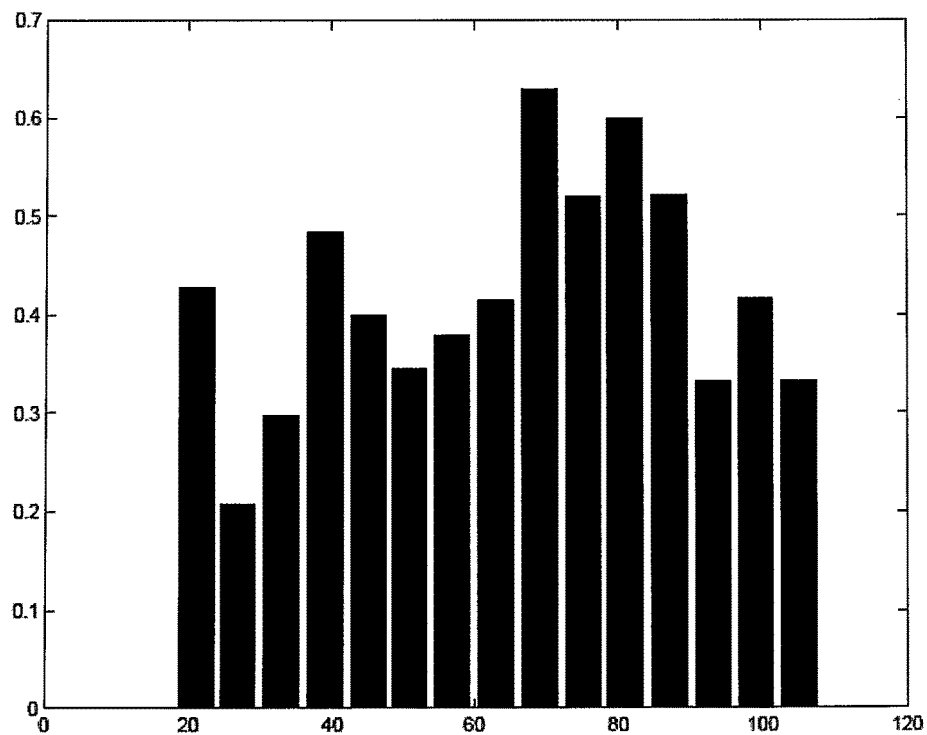

FIG. 22 is a graph showing IL-6 levels over time for the group of TBI patients studied.

Figure 23:
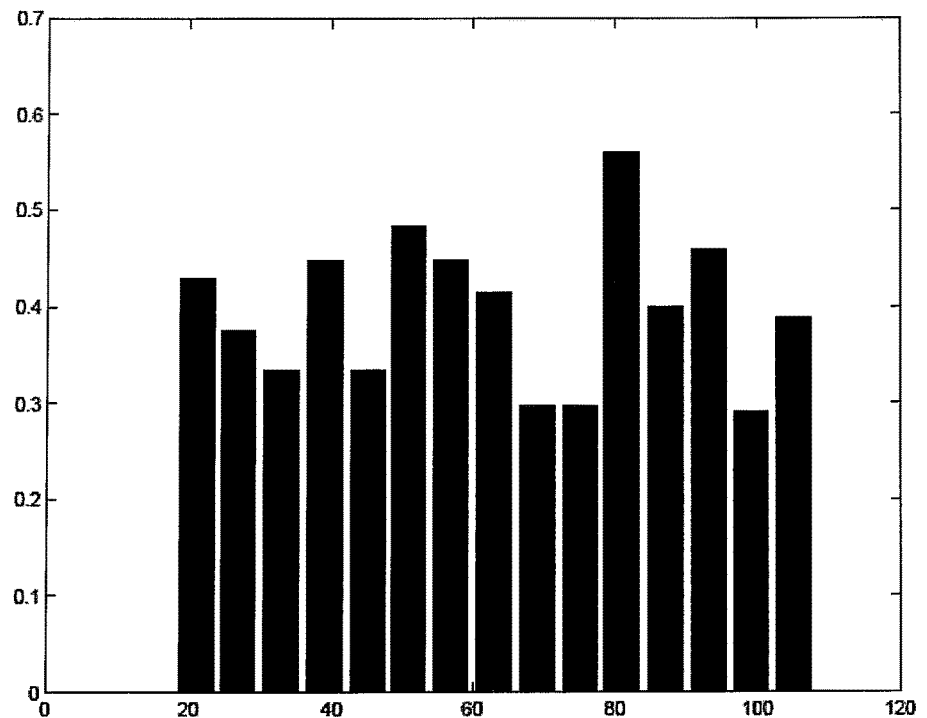

FIG. 23 is a graph showing TNF levels over time for the group of TBI patients studied.

Figure 24:
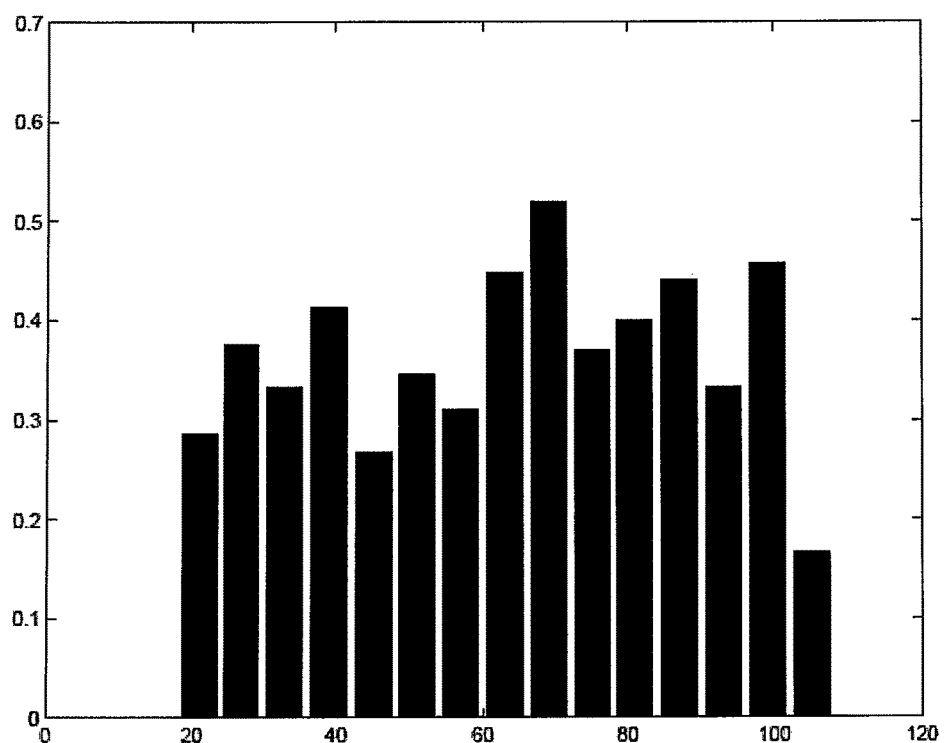

FIG. 24 is a graph showing IL-10 levels over time for the group of TBI patients studied.

Figure 25:
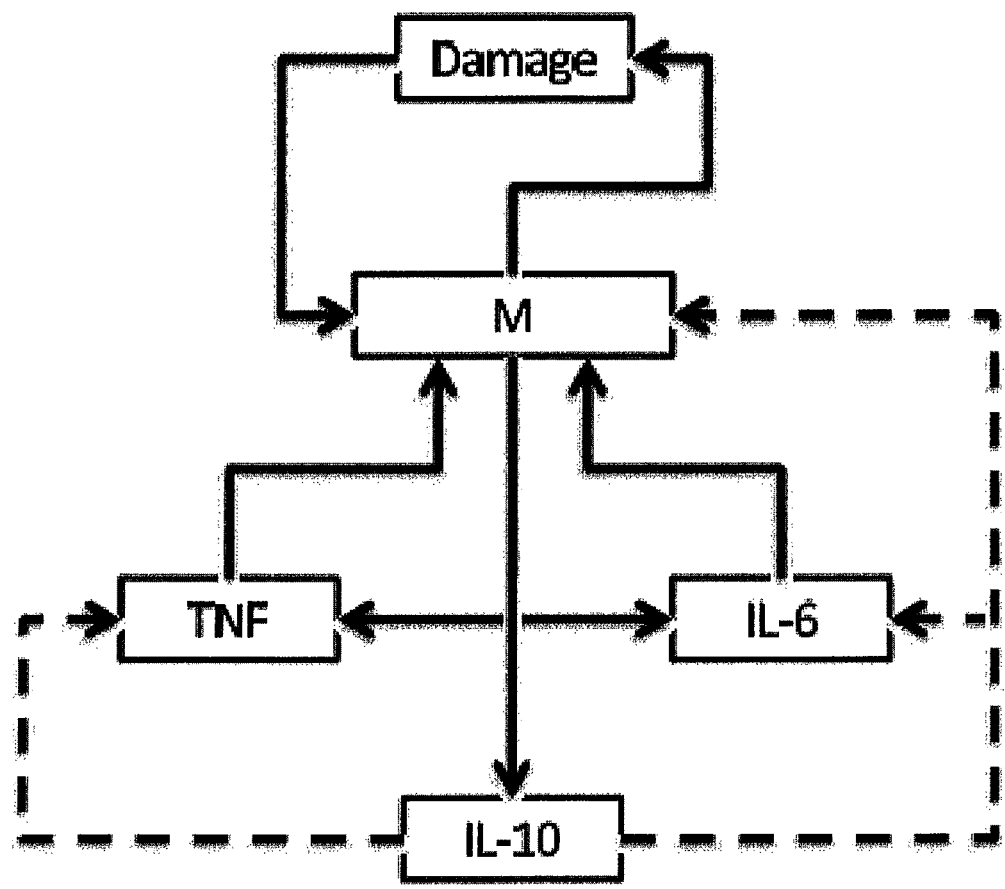

FIG. 25 is a diagram showing relations between variables for TBI used in one embodiment of the ODE modeling described in Example 8.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

A "patient" refers to a live subject, such as a human subject or an animal subject and does not imply a doctor-patient relationship or animal-veterinarian relationship.

The term "comprising" in reference to a given element of a method, composition, apparatus, etc., means that the method, composition or apparatus includes that element, but also may contain other nonspecified elements.

A "vector" is a construct composed of nucleic acids into which additional nucleic acids comprising a genetic element are or can be inserted to facilitate transfer of the genetic element into a cell and permanent or temporary transformation, transfection, expression, incorporation, etc of the cell, typically to either mark the cell, to express a genetic element in the cell, or to store, replicate or propagate the vector and/or genetic element. Vectors containing expression cassettes are broadly available for expression of genes in various host cells, such as E. coli, S. cerevisiae, insect and mammalian cells, such as Chinese Hamster Ovary (CHO) cells, human embryonic kidney (HEK) 293 cells, HeLa cells, or other human cells, such as hepatocytes. Although DNA consisting essentially only of a gene for expressing a recombinant protein can be used to transfect or transform a cell, an extremely large number of vector and transformation systems, many of which are well-known and beyond the scope of this disclosure, are useful in producing a cell that expresses a recombinant protein. Some of these vector systems are known, including, without limitation: yeast, insect, bacterial, mammalian and viral (for example, phage, retroviral, Adenoviral, and Adeno-associated virus) vector systems. Suitable vectors, cells and, in general, expression systems are available commercially from a large variety of sources, including without limitation, Stratagene of La Jolla, Calif. and the American Type Culture Collection (ATCC) of Manassass, Va. In another non-limiting example, plasmid- or episome-based systems useful in gene transfer and expression are broadly known. Any gene for expression of a give polypeptide or protein can be inserted into a suitable vector for transfer and expression in a cell.

By "expression" it is meant the overall flow of information from a gene (without limitation, a functional genetic unit for producing a gene product in a cell or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene. A "chimeric gene" is a gene made by man, typically by recombinant techniques as are broadly known. Nucleic acids are presented, unless otherwise noted, in a 3' to 5' direction. Proteins and polypeptides are presented, unless otherwise noted, in an N-terminus to C-terminus direction.

Any nucleic acid encoding a given polypeptide sequence or other element of a gene can be prepared by a variety of known methods. For example and without limitation, by direct synthesis of the primary DNA sequence for insertion in a gene, gene cassette, vector, etc., by PCR cloning methods, or by restriction and ligation or recombination according to well-established practices. In the case of preparation of a nucleic acid sequence encoding a repetitive sequence, a nucleic acid encoding a single iteration of the repeat may be prepared with blunt or sticky ends, as is known in the art, and subsequently ligated to form multiple iterations. The ligated iterative sequences can then be ligated into a vector, gene or gene cassette by known methods.

The term "treatment" and like terms, in the context of the compositions, constructs and devices described herein, refers to the action and ability of a peptide to modulate (increase, decrease, reduce, and/or stabilize inflammation, typically associated with a disease or condition, in a subject, such as a human or veterinary patient. The ability and effective dosage and treatment regimen for a patient typically is determined by studies of a statistically-relevant population of subjects, and is determined as compared to a placebo or other negative control.

A variety of cell types and cell lines may be used in the bioreactors and methods described herein. At a minimum, the cells must be able to be transfected (non-viral nucleic acid transfer) or transduced (viral nucleic acid transfer) to permit transfer of appropriate genetic material into the cells. The cells also should have the ability to express any genetic construct transferred into the cell in an appropriate manner, such that any genes contained within the transferred nucleic acid material is expressed appropriately—either constitutively or in an appropriately regulated manner. The cells should be able to secrete or otherwise externalize any genetic product of genes contained within the transferred nucleic acid and intended to be secreted or otherwise externalized. Lastly, the cells should be capable of surviving, if not propagating in any bioreactor. Hepatocyte cell lines or hepatocytes (primary human liver cells) may meet these requirements, as would the common HeLa and HEK293 cells. Hepatocytes may be xenogeneic, allogeneic, isogeneic (syngeneic, when appropriate) or autogenic. Other useful cells or cell lines include: HepG2 hepatocyte cell line (American Type Culture Collection HB-8065™), CHO cells, CACO2 enterocyte-like cells, A549 lung epithelial-like cells, fibroblast cells or cell lines, keratinocyte cells or cell lines, or any other cell or cell line that could substitute for a functional or structural cell in any inflammatory disease. The cells may be derived from cell lines, human transplant discards, cell donors, or from the patient's own cell population.

Primary cell cultures or cell lines may be transfected or transduced with a genetic construct by any useful means, such as by liposome-, electroporation-, particle bombardment- or calcium phosphatemediated transfection. Nucleic acids may be transferred into the cell or cell line by transduction, such as by packaging within a suitable transducing particle, such as an adenovirus (Ad), adeno-associated virus (AAV) or retrovirus (e.g., lentivirus) particle according to any of many known methods. In many cases, it is desirable to modify a cell line to include a transferred gene. A number of methods for permanently transforming a cell line are known. For example, by flanking a gene with the well-known retrovirus or AAV terminal repeat structures, or using recombination systems, such as the well-characterized CRELOX system, or even by using linearized plasmids for random integration, a gene can be introduced into the genome of a cell line, thereby creating a suitable cell line for propagation and use in the bioreactors and methods described herein.

A variety of useful bioreactor designs are expected to be useful in the methods described herein. United States Patent Publication Nos. 20080145442, 20050049581, 20050032218, 20050015064 and 20050003535, and U.S. Pat. No. 6,759,245, each of which is incorporated herein by reference for its technical disclosure, describe useful examples of bioreactor devices, how to implement them, useful cell types and related devices and methods of use. In the context of the present disclosure, a bioreactor is a device containing cells for contact with biological fluids of a patient. In its most general sense, a bioreactor comprises an enclosure which contains the cells, and a membrane which retains the cells within the enclosure, yet permits passage of nutrients and polypeptides across the membrane.

Extracorporeal bioreactors are cartridges or vessels having at least a perfusion inlet and a perfusion outlet, and a cell compartment, for example a matrix, within the vessel that provides a suitable environment for living cells while allowing perfusion of the cell compartment with suitable media for maintaining the cells. Such cell compartments can be structurally build containing semi-permeable membranes, e.g., hollow fiber membranes or flat sheet/plate membranes, with circulation of blood or plasma on one side of the membrane and the cells on the other side.

As noted above, the bioreactors described herein contain a selectively permeable barrier made of a material that allows the passage of macromolecules and other cell derived products to and from the subject's plasma or other bodily fluids. The cells themselves do not leave the bioreactor. After circulation and one or multiple passes through the bioreactor, the treated ultrafiltrate (e.g., plasma) may be recombined with the cellular components of the subject's blood and returned to the subject via venous access. When utilizing the bioreactor in a manner in which the device is connected to the patient's systemic circulation, the patient's blood or plasma is supplemented with heparin or other anticoagulants to prevent clotting. This circulation is maintained continuously for, e.g., a 10 hour support period of extracorporeal therapy. In current similar systems, blood or plasma carries toxins from the patient to a bioreactor containing hepatocytes.

One non-limiting embodiment of the present devices include a) a bioreactor comprising a fluid treatment compartment and a cell compartment, and a selectively permeable barrier separating the fluid treatment compartment and the cell compartment, wherein the cell compartment comprises a population of cells comprising a gene for expressing a modulator of an cytokine or other inflammatory agent.

Blood, ultrafiltrate from a subject, or other bodily fluids are passed into the fluid treatment compartment, where agents secreted by the cells pass into the blood, ultrafiltrate, or other bodily fluids, by passage of the agents across the selectively permeable barrier.

Figure 1:
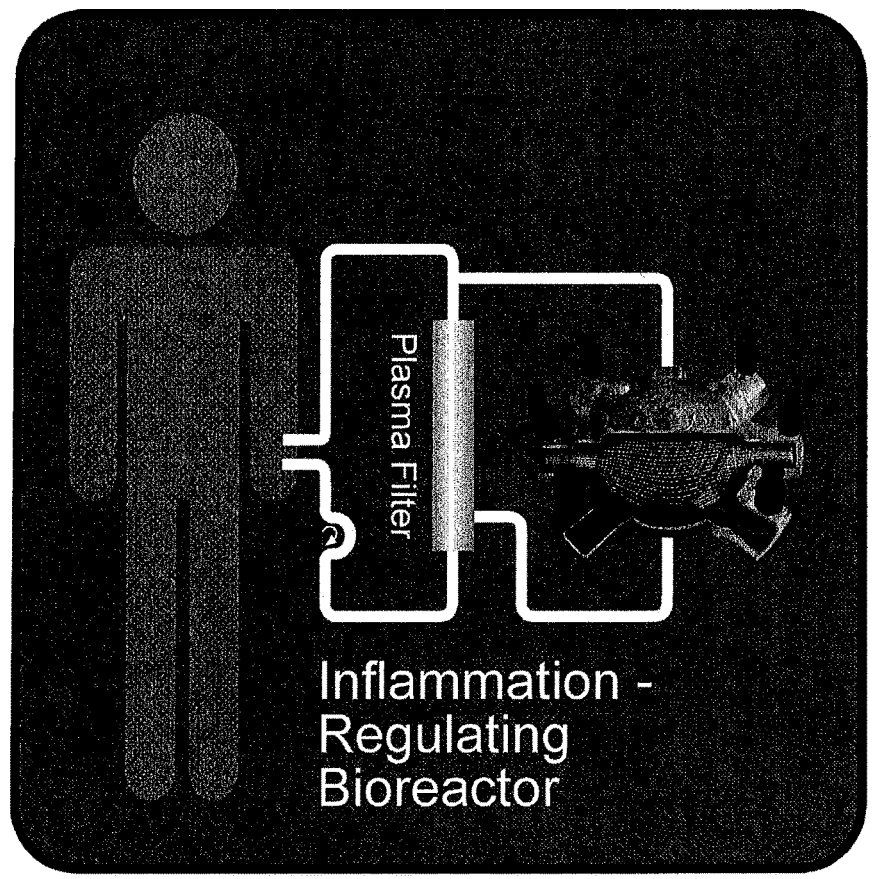
FIG. 1 is a depiction of a self-regulating, individualized theranostic device for the detection and adaptive modulation of inflammation and one possible method of connection of the device to a patient.

Extracorporeal liver support devices including bioreactors are also commonly referred to as bioartificial liver devices (BALDs) or bioartificial liver assist devices (BLADs). A number of such devices are known in the art and can be adapted for use with MSCs. Exemplary commercially available extracorporeal liver support device that can be used as described herein include, but are not limited to, the ELAD® system currently marketed by Vital Therapies, Incorporated (shown in FIG. 1 of U.S. Pat. App. Pub. No. 2005/0182349), Circe's HEPATASSIST®, Gerlach's BELS, and Excorp Medical's BLSS. Additional suitable exemplary devices are described in U.S. Pat. Nos. 6,472,200, 5,605,835; 7,160,719; 7,273,465; 6,858,146; 6,582,955; 5,270,192; 6,759,245; and U.S. Pat. App. Pub. No. 20030017142.

Figure 2:
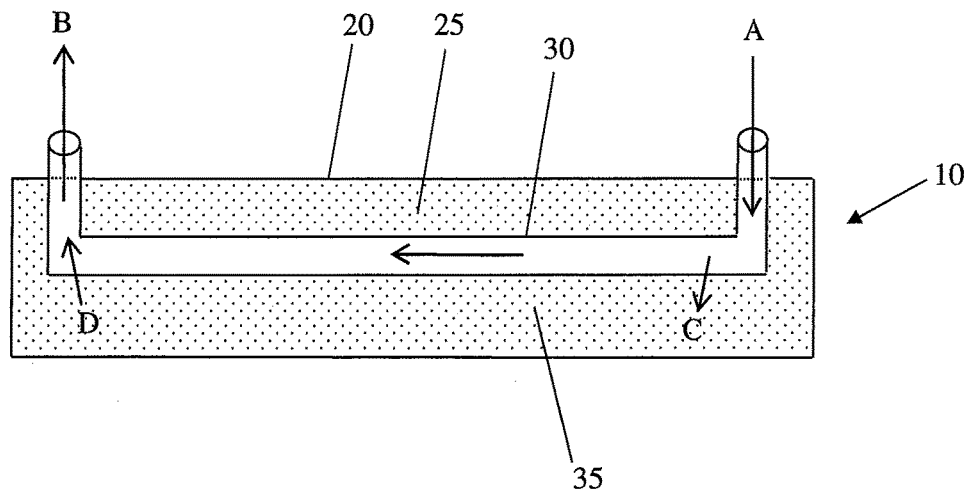
FIG. 2 is a schematic diagram showing a simplified embodiment of a hollow-fiber bioreactor device.

In one embodiment, as depicted schematically in FIG. 2, a bioreactor 10 comprises a closed vessel 20 that can be of any physical configuration, such as a cylinder, tube, cube, rectangular prism, plastic bag or sac etc. The vessel 20 contains a cell culture 35 composed of cells, suitable media and optionally a cell growth scaffold or matrix. A hollow fiber 30 passes into and out of the vessel 20. For simplicity, only one hollow fiber is depicted, though a typical bioreactor comprises multiple hollow fibers. The hollow fiber is selectively permeable, permitting passage of gasses and molecules/compounds having a maximum molecular weight (e.g., a maximum of 70, 80, 90, 100, 110, 120, 130, 140, or 150 kD, including increments therebetween) or size, preferably so long as cells cannot pass across the barrier. The hollow fiber 30 comprises a lumen 35. In use, a fluid, such as cell culture media, and in the context of the present disclosure, a patient's bodily fluids, such as plasma, is passed through the lumen 35 of the hollow fiber 30, depicted by arrows A and B. Nutrients and protein constituents of the plasma C can pass through the walls of the hollow fiber 30 into the cell culture 25. Cytokines, growth factors, immunomodulators and other plasma constituents which relate to an inflammatory state also can pass through the walls of the hollow fiber 30 into the cell culture 25, to stimulate expression of, or to inhibit expression of one or more genes contained within cells of the cell culture. Factors D produced by cells in the cell culture 25 are able to pass through the walls of the hollow fiber 30 and into the plasma or other fluid. In the context of the one embodiment of the present disclosure, the cells within the vessel are modified with one or more genes for expression of one or more factors that inhibit cytokines or growth factors (which means they in some way inhibit production of or action of the one or more cytokines or growth factors).

As would be recognized by those of ordinary skill in the art of bioreactor design and related fields, this is merely a schematic diagram of one embodiment of the bioreactor. Variations of the number and configuration of the hollow fibers, as well as the molecular weight cutoff of the hollow fibers, the types of cells within the device, their number, the presence of one or more opening (closeable, using a valve or other useful closure means) in the vessel for depositing or removing cells, cell media, cell growth scaffolds, drugs, etc. from the vessel, and the size, shape and configuration of the device and its parts are possible and are a matter of design choice and/or optimization. In one embodiment, one or more additional hollow fibers are incorporated into the vessel for use in gas exchange. More specifically oxygen or air can be passed through the one or more additional hollow fibers to oxygenate liquids within the vessel, and to remove $CO_2$ from the vessel. "Tubular" does not imply any cross sectional shape of the hollow fiber, only that the membrane is a fluid conduit.

Plasma can be separated from cellular components of blood using an ultrafiltrate generator or any other plasma filtration method or device. Alternatively, whole blood can be treated by the devices described herein.

Figure 3:
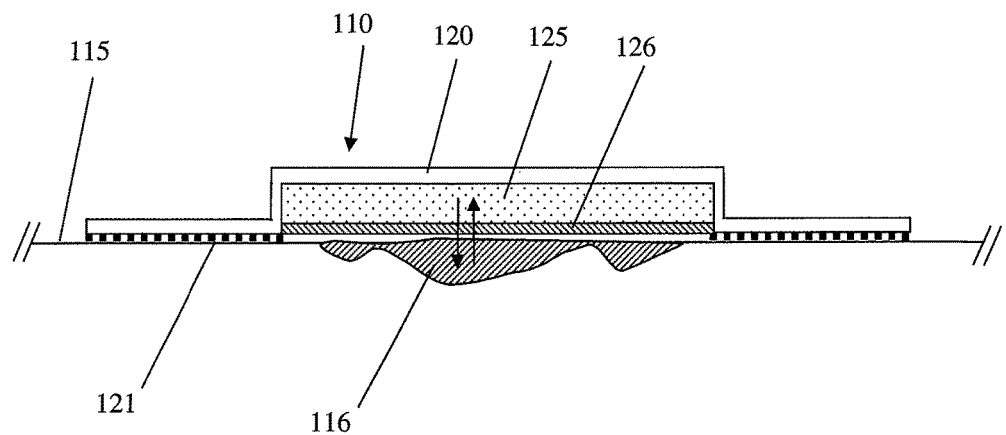
FIG. 3 is a schematic diagram of a "transdermal-type" bioreactor device as described herein.

In a second embodiment, illustrated schematically in FIG. 3, the bioreactor device 110 is a transdermal device configured to adhere to a patient's skin 115 in contact with a wound 116. A large variety of transdermal devices or patches are available and described in the literature. Unless indicated otherwise, any materials used in the relevant arts for such devices and any device configurations available in the art are useful for purposes described herein so long as they are not inconsistent with the functioning of the device as described herein. The device 110 comprises a backing 120 that typically would be occlusive, but which may permit gas exchange. Adhesive 121 is provided to hold the device 110 in place on a patient's skin. A reservoir 126 containing cells, cell medium and, optionally a cell scaffolding is provided and which is sealed between backing 120 and a membrane that permits exchange of cytokines, growth factors, immunomodulators and other plasma constituents which relate to an inflammatory state, as well as nutrients between the wound 116 and the reservoir 125. The membrane may be any suitable membrane.

In yet another exemplary embodiment, depicted schematically for clarity in FIG. 4A, a contact type bioreactor is provided. Bioreactor 210 is provided, comprising a backing 220 with adhesive about its edges. This diagram is a cross-section viewed from the patient contact side of the device. The backing may be any medically or pharmaceutically-acceptable backing and may be wholly occlusive (preventing passage of gasses and moisture) or gas-permeable (permitting passage of gasses and moisture). As indicated above, a large variety of occlusive and gas-permeable backings are available and described in the transdermal device field. A cell growth chamber 225 is shown. A network of hollow fibers 230 is provided for oxygenation and feeding of cells in the cell growth chamber 225. More than one such network may be employed in a device such as the device shown. For example a first network of hollow fibers may be used to supply nutrients in liquid form to the cells, while a second may be used to supply gasses (e.g., oxygen) and to remove $CO_2$ from the cells. As in all embodiments, the cell growth chamber may comprise a cell growth scaffold. In this embodiment, due to the availability of gasses and nutrients via the one or more hollow fiber networks, the backing 220 may be wholly occlusive to prevent contamination and to maintain moisture in the device. The direction of flow of liquid or gasses through the network 230 is shown be arrows F. The network 230 comprises an inlet 231 and an outlet 232, which are attached to a source for the liquid or gasses and a suitable disposal receptacle. Alternately the liquids and/or gasses may be fed to the device 210 and repeatedly passed through the device in a closed-loop fashion, provided there is a large enough reservoir of materials to support growth and/or maintenance of the cells in the device over the intended duration of use. Valves 233 are shown, which may be used to shut off or restrict flow through the inlet 231 and outlet 232. This may be useful in changing out the device, and in general handling of the device. Connectors (not shown), such as Luer lock or taper fittings may be provided for fluidly connecting inlet 231 and outlet (drain) 232 to an external supply/waste disposal or recirculation system. FIGS. 4B and 4C are cross-sectional schematic diagrams of alternate embodiments of the device depicted in FIG. 4A, along segment A shown in FIG. 4A. Both of FIGS. 4B and 4C depict backing 220, cell growth compartment 225, and hollow fiber matrix 230. Adhesive 221 (optional) is shown in these figures attached to lateral extensions or "tabs" extending from the device. Also depicted is a permeable membrane 240 for entrapping cells within the compartment 225, which can be any suitable polymeric or hydrogel composition as are broadly known and available.

As can be envisioned by one of ordinary skill, the overall structure and composition of the devices depicted in FIGS. 4A-C can be varied according to design choice and optimization. For instance, adhesive and the depicted extensions or tabs extending laterally from the device may be omitted. Likewise, the backing may be omitted, with the barrier membrane extending around and enclosing the cell growth compartment. For example, the membrane may form a "bag", as is depicted in US Patent Publication No. 20050015064 (See, e.g., FIG. 4D). In such an example, the device is wrapped, taped or otherwise placed in contact with a wound.

FIG. 4D illustrates the concept of using a perfused flat sheet membrane bag in an active wound dressing. The membrane is temporarily placed above the wound and below the outer wound dressing. Such a membrane-based wound dressing can provide nutrition, oxygenation, pH regulation, electrolyte balance, and detoxification of wound debris. This therapy is expected to improve the clinical outcome by reducing the time of wound healing while enabling larger treatment areas, and thus reducing the mortality rate in patients with large surface burns. As shown in FIG. 4D, cells, such as basal keratinocytes, can be applied to the wound prior to application of the device.

In any of the devices depicted in FIGS. 2, 3 4A-4D, or otherwise disclosed herein, the devices may be provided with one or more one or more ports, or openings in the body of the device that are closeable or sealable through which cells, a patient's biofluid or other contents within the device may be sampled or cells and/or cell growth scaffolds, or other compounds or compositions may be inserted into the device. One or more ports also may be provided for holding or inserting probes for analyzing the contents of the device, such as temperature probes, pH probes, oxygen probes or fluorescent light sources and/or fluorescence detection devices, such as a CCD (Charge-Coupled Device). An optical port also may be provided for imaging of cells or cell-bearing structures within the device, for example in combination with a fluorescent (excitation) light source.

In the context of burn healing, the inflammatory process associated with burn healing can be modeled by computer and immunomodulatory factor production can be controlled to optimize the healing process. TNF, IL-1α, and IL-1β levels are examples of immunomodulatory factors that might be controlled in a burn patient to prevent untoward inflammatory events. Thus, placing cells transformed with the sTNFR and IL-1ra genetic constructs, is expected to provide control over the inflammatory process. Mathematical modeling or agent-based modeling methods for determining targets for modulation/control of the immune response are described, for example, in United States Patent Publication No. 20080228456, in a variety of contexts. The choice of cytokines to control, and how strong the control needs to be can be modeled in this manner. For instance, when a stronger response is necessary to control a cytokine such as TNF or IL-1, more cells containing a construct for expressing an inhibitor of the cytokine may be added to the bioreactor. Cells may be propagated and dispensed into a device either as individual cell populations, or as cells deposited on a cell growth scaffold, such as beads or ECM sheets. Cells, or cell growth scaffolds comprising cells may be stored in any suitable manner that preserves the viability of the cells, such as by freezing or any other suitable manner.

In the devices described herein, the cell-containing compartment may comprise a cell growth scaffold, such as a collagen, synthetic polymers or decellularized ECM-derived material onto which suitable cells are grown or maintained. An "ECM-derived material," is a material prepared from an extracellular matrix-containing tissue. Any type of extracellular matrix tissue can be used in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM is isolated from a vertebrate animal, for example and without limitation, from a warm blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane.

Commercially available ECM preparations can also be used in the methods, devices and compositions described herein. In one embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

Selectively-permeable membranes useful in the hollow fibers or other structures used to transfer include hydrophilic or hydrophobic membranes, including, without limitation, polypropylene, polyamide, polysulfone, cellulose, or silicon-rubber is preferred for hollow fiber membranes. The selection of hollow fiber membranes depends on the molecules planned for substance exchange. However, any membranes, such as hollow fiber membranes, useful as substance exchange devices (or mass exchange devices), can be used.

Gene constructs for controlling levels of a given factor implicated in the inflammatory response may be prepared using any of the large number of recombinant methods described in the literature and which are available from companies, such as Invitrogen, Stratagene and Clontech, among many others. Constructs can be assembled from nucleic acid fragments that contain suitable gene elements, such as coding sequences, response elements, etc.

TNF—A TNF construct includes at a minimum a control sequence (promoters, enhancers, response elements, etc.) that increases expression of a downstream (3') coding sequence in the presence of TNF (not necessarily directly responsive to TNF, but also responsive to a cellular event triggered by TNF, such as NF-κB) and a sequence encoding an inhibitor of TNF activity, such as a TNF antagonist or TNF-specific binding reagent, such as a soluble receptor or an antibody or an scFv fragment (cloning and expressing antibody fragments such as an scFV or Fab fragment by, e.g., phage display, is now routinely performed by commercial vendors), or an appropriate "cytokine trap" (see, e.g., Economides, A N et al. *Nature Medicine,* 9(1):47-52 (2003)).

TNF carries out its inflammatory signaling in cells via activation of the nuclear factor-kappa B (NF-κB) pathway and is inhibited by soluble TNF receptor. The classical pathway of NF-κB activation involves an inflammatory response operating through a heterodimer of p50 and p65. NF-κB dimers are held in the inactive state by a family of inhibitors called I-κB. Receptor signaling leads to activation of a multisubunit I-κB kinase (IKK) complex which phosphorylates I-κB on two key serines. Phosphorylation of I-κB marks it for degradation by the ubiquitin pathway, so that the NF-κB dimer is liberated to translocate to the nucleus, bind DNA and activate transcription. It is essential that the inflammatory actions of NF-κB are switched off once the inflammatory signal ceases, and because the inhibitor I-κB is degraded on NF-κB activation. This means new I-κB must be synthesized. There are three main members of the I-κB family, two of which, IκBß and I-κBε are synthesized constitutively and reestablish NF-κB inhibition on cessation of signaling with a relatively slow time course. Synthesis of the third, I-κBα, is under the control of NF-κB itself, and it is therefore produced in response to signaling: it enters the nucleus on synthesis, binds to NF-κB and shuttles it back to the cytoplasm via a nuclear export signal, switching off NF-κB action with a very short delay, thus making NF-κB activity self-limiting.

Accordingly, an appropriate genetic construct, such as a recombinant DNA plasmid containing a gene for expressing soluble TNF receptor (sTNFR), for example an NF-κB-sensitive promoter operably linked (e.g., upstream of) a sTNFR coding sequence. A soluble TNF receptor is an antagonist of TNF (see, e.g., US Patent Publication No. 20070249538 for a more detailed description of sTNFR and variations thereof) and can be derived from TNFR1 (TNFRα or TNFR1a) and TNFR2 (TNFRβ or TNFR1b). An exemplary sequence for STNF1a is provided in FIG. 6B (referenced below). An exemplary TNF-responsive promoter element is described below and is an NF-κB-sensitive promoter.

IL-1—An IL-1 (for example IL-1β) construct includes at a minimum a control sequence that increases expression of a downstream (3') coding sequence in the presence of IL-1, operably linked to a sequence encoding an inhibitor of IL-1 activity (e.g., by binding IL-1 or otherwise causing downregulation of either IL-1 production, availability or activity), such as an IL-1 antagonist or IL-1-specific binding reagent, such as an antibody or an scFv fragment, or an appropriate "cytokine trap". An exemplary IL-1-responsive promoter element is described below, and an exemplary IL-1 receptor antagonist (IL-1ra) (also referred to as, IL1rn) sequence is shown in FIG. 16B (referenced below).

TGFβ1—A TGFβ1 construct includes, at a minimum, a control sequence that increases expression of a downstream (3') coding sequence in the presence of TGFβ1, operably linked to a sequence encoding an inhibitor of TGFβ1 activity (e.g., by binding TGFβ1 or otherwise causing downregulation of either TGFβ1 production, availability or activity), such as an TGFβ1 antagonist, a TGFβ1 specific binding reagent, such as an antibody or an scFv fragment, an appropriate "cytokine trap" or a LAP. An exemplary TGFβ1-responsive promoter element is plasminogen activator inhibitor type 1 (PAI1) and an exemplary LAP sequence are shown in FIG. 19 (referenced below).

IL-6—An IL-6 construct includes, at a minimum, a control sequence that increases expression of a downstream (3') coding sequence in the presence of IL-6. An exemplary control sequence is (SEQ ID NO: 8):

```
5'-GTATTTCCCAGAAAAGGAACGTATTTCCCAGAAAA
GGAACGTATTTCCCAGAAAAGGAAC-3'
```

This promoter element contains only 3 copies of the relevant response element, which can be increased. Of note, this can be activated by various ligands including interferon-alpha, interferon-gamma, EGF, PDGF and IL-6. Soluble IL-6 receptor, a "cytokine trap" (see, e.g., Economides, A N et al. *Nature Medicine,* 9(1):47-52 (2003)) or a binding reagent specific to IL-6 may be encoded by this gene (See, generally, SL Plushner, *The Annals of Pharmacotherapy,* 2008 November, Volume 42:1660-68; Economides, A N et al. *Nature Medicine,* 9(1):47-52 (2003); and Ancey, C, et al. *J. Biol. Chem.* 278(19):16968-16972 (2003)).

Sepsis

One exemplary therapeutic goal is not to abolish sepsis-induced inflammation per se but rather to define its time course and reduce damage or dysfunction (i.e. promote healing) by modulating inflammation in a rational fashion. More specifically, our goal is to attenuate the positive feedback cycle of inflammation damage inflammation, by allowing the body to re-equilibrate its inflammatory response through a repeated, incremental reduction of pro-inflammatory influences. To do so, we have conceived of and prototyped a self-regulating device for individualized control of inflammation.

Sepsis following infection, trauma, or major surgery results in prolonged, expensive intensive care unit hospitalization and remains a major cause of mortality. It is estimated that over 750,000 patients develop sepsis, of which over 200,000 die. Sepsis is most often caused by bacterial infection, and even more specifically by Gram-negative bacterial infection. The acute inflammatory response to biological stress such as Gram-negative bacterial endotoxin (lipopolysaccharide; LPS) involves a cascade of events mediated by a large array of cells and molecules that locate invading pathogens or damaged tissue, alert and recruit other cells and molecules, eliminate the offending agents, and finally restore the body to equilibrium. Inflammation causes damage to tissues, which in turn lead to the production of molecules that re-stimulate inflammation. Perplexingly, this feed-forward loop can lead to persistent, dysregulated inflammation that promotes organ dysfunction and death.

Our overarching hypothesis is that the acute, self-amplifying inflammatory response in experimental Gram-negative sepsis is driven in large part by cytokines such as TNF and IL-1, and that adaptive neutralization of these cytokines can result in reduced inflammation, organ damage, and perhaps also improved survival. Our secondary hypothesis is that computational simulations of the device and disease state can streamline the design of this theranostic device and suggest the optimal protocols for its application.

One embodiment of the prototype inflammation-regulating bioreactor is based on the production of sTNFR driven by TNF. This design was chosen because TNF is the primary driver of a broad array of inflammatory mediators upon stimulation with endotoxin (Brown, K. L., et al. *Trends Immunol.* 28, 260-266 (2007)). We propose to create, test, and mathematically model a sepsis theranostic based on a modified liver bioreactor, and in parallel to explore computationally the likelihood of clinical utility of such a theranostic device. Gene-modified human HepG2 cells can act as both diagnostic indicators (of TNF as well as sTNFR) while at the same time modifying the inflammatory response using sTNFR. Development of this device will utilize mechanistic computational simulations of the impact of the proposed device on a simulated population of human septic patients, much as we simulated the response to neutralizing anti-TNF antibodies in sepsis (Clermont, G. et al. *Crit. Care Med.* 32, 2061-2070 (2004)) as well as vaccination in the setting of anthrax (Kumar, R., et al. Shock 29, 104-111 (2008)) The device is envisioned as being developed using an iterative process of simulation and empirical studies to suggest optimal device characteristics as well as timing, duration, and extent of neutralization of TNF, IL-1, or other relevant inflammatory cytokines; see FIG. 5).

Inflammatory response associated with other disease states or conditions, such as trauma, may be controlled using the methods described herein. For example TNF and IL-1 are implicated in the inflammatory response associated with trauma, such that control of IL-1 and/or TNF should effectively control the inflammatory response associated with trauma (See, e.g., United States Patent Publication Nos. 20030087285 and 20080228456) discussed above.

EXAMPLE 1—TNF-STNFR PLASMID

FIG. 6A shows a plasmid map for a TNF-sTNFR plasmid (3×NFkB-sTNFR-pcDNA3). The plasmid comprises three copies of the NFkB responsive elements with reduced TK promoter driving production of sTNFR1a. To create this vector we used pcDNA3 (from Invitrogen) as a backbone. Our insert is 3×NFkB-TK+sTNFR1A. The plasmid also comprises NeoR—gene resistance to Neomycin. This was used for transient transfection experiments. FIG. 6B provides the sequence of this construct in pertinent part. Stably transfected lines can be produced by spontaneous integration of the vector and can be selected by Neomycin resistance. In response to TNF stimulation, cells will produce sTNFR1A. Response to TNF for this vector in HepG2 cells transiently transfected with the plasmid is shown in Example 2.

EXAMPLE 2—PROTOTYPE BIOFEEDBACK PLASMID

In our prototype biofeedback plasmid, described in Example 1, genetic elements (the NF-κB promoter) responsive to TNF were placed upstream of the gene coding for mouse sTNFR (FIG. 6A6B). TNF carries out its inflammatory signaling in cells via activation of the nuclear factor-kappa B (NFκB) pathway and is inhibited by sTNFR. Accordingly, we created a recombinant DNA plasmid containing the mouse NF-κB-sensitive promoter upstream of the mouse sTNFR gene, and inserted this plasmid into human cells that we felt would be appropriate for long-term, high-level expression of this recombinant gene product (the HepG2 liver cell line).

The reason for the choice of mouse soluble TNF receptor and human cell line was that we could stimulate the cells with a mouse cytokine and obtain the species-specific cytokine inhibitor, while hopefully avoiding the confounding result that would occur if we were to detect the sTNFR produced by the HepG2 cells themselves.

To make the plasmid, we obtained plasmids that contained each element separately (a NF-kB response element was obtained by PCR from a plasmid (3×NFkBTK109) containing that sequence, and sTNFR sequence was obtained from the sTNFR ImageClone™ [Invitrogen] plasmid), as well as a plasmid that allows for high-levels gene transcription in mammalian cells (pcDNA3). Next, the TNFdriven sTNFR plasmid was inserted into HepG2 cells, which were stimulated with mouse TNF following by assay of mouse sTNFR (FIG. 7). Control studies included assaying human sTNFR (to determine if there is any contribution from the human HepG2 cells' own sTNFR), no stimulus, and various other controls (FIG. 7). As seen in this figure, we have created a circuit in which 1) no sTNFR is produced from HepG2 cells transfected with the negative control plasmid or the TNF-driven sTNFR plasmid in the absence of TNF (FIG. 7A), and 2) TNF is produced significantly above background from HepG2 cells transfected with the TNF-driven sTNFR plasmid following stimulation with TNF (FIG. 7A), and 3) that only the TNF-driven sTNFR construct led to a significant reduction in the levels of TNF. We extended these studies to assess the dose-responsiveness of our construct to mouse TNF (FIGS. 7 and 8). Our results suggest that maximal activation was approximately 3.5-fold relative to baseline (FIG. 8). We note that this may be an under-estimate, since the assay may not recognize sTNFR bound to TNF and since constructs using the same TNF-responsive element upstream of luciferase rather than sTNFR suggested a simulation of up to 12-fold (data not shown). We have also successfully transfected HepG2 cells with our proposed fluorescent protein (FIGS. 11A-11B).

In another experiment, HepG2 cells transfected with this plasmid were placed in a bioreactor and tested for their initial response to TNF as well as for the time for this initial response to decay. $27 \times 10^6$ HepG2 cells were transfected with the 3×NFkB-sTNFR-pcDNA3 vector and were seeded in an 8 ml bioreactor. Samples were collected at a rate of 1 tube/per hour. The cells were stimulated with TNF as follows: 5 day 0 ng/ml TNF; 1 day 3 ng/ml TNF; 1 day 0 ng/ml TNF; 1 day 1 ng/ml TNF; 1 day 0 ng/ml TNF. Results are shown in FIG. 9.

We also carried out studies on establishing the culture conditions for HepG2 cells, in both standard 2-D and in bioreactor cultures. We utilized a four-compartment, hollow fiber culture bioreactor in which cells can spontaneously reassemble to tissue-like structures in a 3-D perfused cell compartment. (Gerlach, J. C. Bioreactors for extracorporeal liver support. *Cell Transplant.* 15 Suppl 1, 591103 (2006)) Importantly, the bioreactor comes in several distinct configurations and volumes, including 8 mL, 2 mL, and 1 mL. Importantly, the 1 mL bioreactor is optimized for imaging, a design that may facilitate optical detection of fluorescent or other tagged proteins used for determination of either the patient's own local or systemic inflammatory state or of the production of relevant proteins by the bioreactor in response to a given patient's inflammatory response.

The prototype inflammation-regulating bioreactor was created as follows. The 3-D nature of the cell compartment allows cells to spontaneously form tissue-like structures (Gerlach, J. C. et al. Improved hepatocyte in vitro maintenance in a culture model with woven multicompartment capillary systems: electron microscopy studies. *Hepatology* 22, 546-552 (1995) and Zeilinger, K. et al. Time course of primary liver cell reorganization in three-dimensional high-density bioreactors for extracorporeal liver support: an immunohistochemical and ultrastructural study. *Tissue Eng* 10, 1113-1124 (2004)), similar to those found in vivo, and the convection-based mass transfer as well as the mass exchange in the cell compartment allow restructuring of neo-sinusoidal endothelialized perfusion channels. In turn, these channels allow for physiologic perfusion and flow/pressure alterations as in parenchymal organs. Within 2-3 days of culture, liver cells spontaneously form tissue-like structures, including neo-sinusoids, (Gerlach, J. C. et al. Improved hepatocyte in vitro maintenance in a culture model with woven multicompartment capillary systems: electron microscopy studies. *Hepatology* 22, 546-552 (1995)) with neo-formations of spaces of Dissé lined by endothelial cells and structures resembling the Canals of Hering, the anatomical stem cell niche of liver progenitor cells. The vascular-like perfusion allows for long-term support of a cell mass under substantial high-density conditions.

Each bioreactor contains two bundles of hydrophilic polyether sulfone hollow fiber microfiltration membranes (mPES, Membrana, Wuppertal, Germany) for transport of culture medium (forming 2 independent medium compartments), interwoven with one bundle of multilaminate hydrophobic hollow fiber oxygenation membranes (MHF, Mitsubishi, Tokyo, Japan) for transport of oxygen and carbon dioxide (forming a gas compartment). The fibers are potted within a polyurethane housing (Gerlach, J., Schauwecker, H. H., Hennig, E., & Bucherl, E. S. Endothelial cell seeding on different polyurethanes. *Artif. Organs* 13, 144-147 (1989)) (PUR, Morton, Bremen, Germany), and cells are inoculated through 24 silicone rubber tubes (Silastic, Dow Corning, N.Y., USA). Cells are thus cultured in the interstitial spaces between the fibers (the fourth compartment, the cell compartment). The microfiltration fibers (Gerlach, J., Stoll, P., Schnoy, N., & Neuhaus, P. Comparison of hollow fibre membranes for hepatocyte immobilisation in bioreactors. *Int. J. Art. Org.* 19, 610-616 (1996)) have a molecular weight cut off of MW 400 kDa, allowing larger proteins to pass freely through the fiber walls and into the cell compartment. Culture medium circulates from the lumens of the microfiltration fibers to the cell compartment and back to the fiber lumens, due to the axial pressure drop from the inlet to the outlet of each fiber lumen (Starling flow)(Starling, E. H. On the absorption of fluid from the convective tissue space. *J. Physiol* 19, 312-326 (1896); Kelsey, L. J., Pillarella, M. R., & Zyndney, A. L. Theoretical analysis of convective flow profiles in a hollow-fiber membrane bioreactor. *Chemical Engineering Science* 45, 3211-3220 (1990); and Bruining, W. J. A general description of flows and pressures in hollow fiber membrane modules. *Chemical Engineering Science* 44, 1441-1447 (1989)). Medium is pumped through the two-microfiltration fiber bundles in opposing directions (countercurrent flow), allowing the medium entering the cell compartment from one bundle (at its high pressure end) to exit by reentering the same bundle (at its low pressure end) or by entering the other bundle (at its low pressure end, adjacent to the first bundle's high pressure end). This complex flow pattern mimics an "arterial and venous" flow in natural tissues ensures that the medium in the cell compartment is well-mixed, so that most of the cells are exposed to the same low concentrations of nutrients, toxins, and waste products, as in the natural liver sinusoids. Additionally, the interwoven oxygenation fibers (Gerlach, J., Kloppel, K., Stoll, P., Vienken, J., & Muller, C. Gas supply across membranes in bioreactors for hepatocyte culture. *Artif. Organs* 14, 328333 (1990)) ensure that most of the cells receive adequate oxygen delivery and carbon dioxide removal. The gas flow through the oxygenation fibers can be considered as laminar, fully-developed flow of a compressible Newtonian fluid in a circular tube, allowing an analytical solution predicting the gas flow rate as a function of the axial pressure drop along the fibers (Federspiel, W. J., Williams, J. L., & Hattler, B. G. Gas flow dynamics in hollow-fiber membranes. *Aiche J.* 42, 2094-2099 (1996)).

The bioreactor is integrated into a processor-controlled perfusion device with electronic pressure and flow regulation. Modular pump units for recirculation and fresh media feed, respectively, with exchangeable multi-channel flow heads and gears serve for medium recirculation and—substitution to provide constant levels of pH and nutrition to the cells. A heating unit provides a constant temperature within the perfusion circuit. Flow rates of compressed air and carbon dioxide ($CO_2$) are controlled by 2 rotameters with a gas-mixing unit. The perfusion tubing with bubble traps is made of standard medical grade dialysis PVC (B. Braun, Melsungen, Germany). Sterilization is performed with ethylene oxide at 60° C. according to clinical standards. We describe in this Example the first study using this type of bioreactor seeded with the gene-modified HepG2 cells (transfected with the TNF-driven sTNFR DNA construct).

The 3-D nature of the cell compartment of the prototype bioreactor allows cells to spontaneously form tissue-like structures, (Gerlach, J. C. Bioreactors for extracorporeal liver support. *Cell Transplant.* 15 Suppl 1, S91-103 (2006)). similar to those found in vivo, and the convection-based mass transfer as well as the mass exchange in the cell compartment allow restructuring of neo-sinusoidal endothelialized perfusion channels. In turn, these channels allow for physiologic perfusion and flow/pressure alterations as in parenchymal organs. In these bioreactors, hepatocytes and HepG2 cells form neo-sinusoids, endothelialized spaces of Dissé, and Canals of Hering. (Gerlach, J. C. Bioreactors for extracorporeal liver support. *Cell Transplant.* 15 Suppl 1, S91-103 (2006)). Each bioreactor contains two bundles of hydrophilic polyether sulfone hollow fiber microfiltration membranes (mPES, Membrana, Wuppertal, Germany) for transport of culture medium (forming 2 independent medium compartments), interwoven with one bundle of multilaminate hydrophobic hollow fiber oxygenation membranes (MHF, Mitsubishi, Tokyo, Japan) for transport of oxygen and carbon dioxide (forming a gas compartment). The fibers are potted within a polyurethane housing (PUR, Morton, Bremen, Germany), and cells are inoculated through 24 silicone rubber tubes (Silastic, Dow Corning, N.Y., USA). The microfiltration fibers have a molecular weight cut off of MW 400 kDa, allowing larger proteins to pass freely through the fiber walls and into the cell compartment. Culture medium circulates from the lumens of the microfiltration fibers to the cell compartment and back to the fiber lumens, due to the axial pressure drop from the inlet to the outlet of each fiber lumen (Starling flow) (Gerlach, J. C. Bioreactors for extracorporeal liver support. *Cell Transplant.* 15 Suppl 1, S91-103 (2006)), with a complex flow pattern that mimics an "arterial and venous" flow found in natural tissues. The interwoven oxygenation fibers ensure adequate oxygenation and carbon dioxide removal via 2 rotameters with a gas-mixing unit. The bioreactor is integrated into a processor-controlled perfusion device with electronic pressure and flow regulation. A heating unit provides a constant temperature within the perfusion circuit. The perfusion tubing with bubble traps is made of standard medical grade dialysis PVC (B. Braun, Melsungen, Germany).

FIG. 10 shows that we can grow HepG2 cells both in standard 2-D (FIG. 10A) and bioreactor cultures (FIGS. 10B-C), and that cells cultured thus can respond to mouse TNF-α by producing mouse sTNFR above those levels driven by the basal promoter (FIG. 10D). We expect to improve upon the degree of inducibility of sTNFR and increase the duration of the experiment by creating stably transfected HepG2 cells. Moreover, we utilized an Analytical Bioreactor, which is optimized for imaging to carry out fluorescence studies (FIG. 11C).

Induction of fluorescent protein expression by cytokine/growth factor (e.g. TNF levels) can be used for monitoring these factors in patient, as a means of assessing the local or general inflammatory state of the patient.

Designing a "theranostic" variant of the biohybrid device—We envision this device as a true "theranostic," meaning that we wish to not only modify the course of acute inflammation but also to track in near real-time. We therefore propose to assess the amount of active TNF as well as sTNFR both directly (by Luminex™ and ELISA assays) and indirectly, by triggering the production of a fluorescent protein in addition to sTNFR in response to TNF. We will pursue to complementary strategies to achieve this goal. In the first, HepG2 cells will be transfected with a construct consisting of the TNF-sensitive promoter/enhancer element (see, e.g., Example 1) upstream of a fluorescent protein in order to detect TNF indirectly. Based on the literature regarding existing fluorescent proteins, most available fluorescent proteins have maturation times longer than 8 hours (a delay that is too long to be useful for diagnostic purposes). One protein, mCherry (Clontech), has a maturation time of 15 min and another, TurboFP635 (Evrogen, Inc.; FIGS. 11A and 11B) has a 24 min maturation time. We chose to proceed with the latter since it produces a larger quantum yield (0.34) versus 0.22 for mCherry. This approach will allow us to assess the relative levels of TNF, which can be confirmed and calibrated against a TNF-α assay (e.g. Luminex™ or ELISA).

In the second approach, we will place a fluorescent protein downstream of the sTNFR coding region in a manner that will allow the production of the fluorescent protein only if sTNFR is produced. To do so, we have begun to construct a vector that includes an Internal Ribosomal Entry Site (IRES)[26] and a fluorescent protein. IRESs are relatively short DNA sequences that can initiate RNA translation in a 5' cap-independent fashion. Placement of the IRES and a second gene of interest (ORF 2) downstream of the first target gene (ORF 1) allows co-expression of ORF 1 in a cap-dependent manner and ORF 2 in a cap-independent fashion, thus facilitating translation of two proteins from one mRNA transcript.[26] For creation of constructs with bicistronic expression of TurboFP635, we have created a vector which contains IRES followed by TurboFP635 (data not shown), which will simplify subsequent work on future bicistronic vectors. This second approach will allow us to assess the degree of sTNFR production indirectly. Similarly to our proposed strategy for the detection of TNF (see above), we will compare the results of the fluorescence studies to the results of a mouse-specific sTNFR ELISA (FIGS. 7, 8, and 9).

The above studies will be carried out using HepG2 cells transiently transfected with the various constructs in standard 2-D culture in order to establish optimal experimental conditions. We will examine the production of TurboFP635 in response to various doses of TNF (0.1, 0.3, 1, 3, and 10 ng/mL) at various time points (0, 1, 2, 4, 8, and 24 h). We will then progress to studies in bioreactor culture, in which we will duplicate the dose-curve and time course studies based on the data from the 2-D culture experiments. We will make use of the 1 mL, 4-chamber Analytic Bioreactor. This bioreactor provides four separate cell chambers with approximately 120 µL of volume in each chamber for cells. A separate inoculation port is provided for each chamber. Each of the chambers is connected to the fiber pathways to expose all the chambers to common media recirculation. Thermonox cover slips on the bottom of the chambers, and transparent lids for light transmission, allow real time optical microscopy of the cells in the cell chambers. The Analytical Bioreactor can remain connected to the full bioreactor setup, including the heating element that ensures that the cells will receive culture medium at 37° C., while fluorescence imaging is performed (Zeiss Axiskop 40 and JenOptik cooled CCD camera). Fluorescence can be quantified using JenOptik, Optimas, NIH Image, Scion Image, or similar software.

In parallel, we will carry out studies using a bioreactor setup using a 2-mL bioreactor, in which we will repeat variants of the experiment described in FIG. 9. In this experiment, we will vary the dose of mouse TNF injected into the bioreactor (0.1, 0.3, 1, 3, and 10 ng/mL), the flow rate of medium through the bioreactor, and the length of the medium washing period. We will determine immunofluorescence at various time points (0, 1, 2, 4, 8, 24, 48, 72, and 96 h). If our simulations suggest that we need to ramp up sTNFR production more rapidly than our current construct allows in order to achieve an optimal outcome in vivo, we will modify our TNF-responsive element (e.g. by adding or removing NF-κB elements). We will then create a stable transfection vector as follows. The TNF-responsive element (NF-κB) and sTNFR open reading frame from our NF-kB-sTNFR-pcDNA3 (Example 1) will be inserted into the pLenti6.3 vector (Invitrogen). The packaging cell line 293FT will be transfected with the new vector together with a packaging vector mixture (ViraPower™, Invitrogen). Stably transfected HepG2 cells will be produced by infection with viral stock following antibiotic selection and follow the procedure described in that figure. These cells will then be seeded into a liver bioreactor (see below).

Our proposed device would serve to "ratchet down" the positive feedback inflammatory loops set in motion by endotoxin or any other TNF-α-inducing stimulus and self-augmented proximally in large part by TNF-α itself (Jones, A. L. et al. Cancer Surv. 8, 817-836 (1989)). Accordingly, have characterized the production of TNF-α and its natural inhibitor (sTNFR) in endotoxemic mice and rats. In mice subjected to 3 mg/kg endotoxin, TNF-α reached a peak by 90 min and declined rapidly (Chow, C. C. et al. Shock 24, 74-84 (2005)), while sTNFR rose by 30 min, remained elevated until ~12 h and then declined slowly (FIG. 12). We have observed similar dynamics of TNF-α in rats subjected to 3 mg/kg LPS (FIG. 13A) (Daun, S. et al. J. Theor. Biol. 253, 843-853 (2008)). Most of these data have served as the basis for calibration of mathematical models of the acute inflammatory response in mice (Chow, C. C. et al. The acute inflammatory response in diverse shock states. Shock 24, 74-84 (2005)) and rats (FIG. 13A) (Daun, S. et al. J. Theor. Biol. 253, 843-853 (2008)), respectively (though the rat $E.$ $coli$ peritonitis data are as yet unpublished). Importantly, we have carried out detailed studies in rats subjected to sepsis induced by the intraperitoneal implantation of a fibrin clot containing various inocula of $E.$ $coli$ (FIGS. 13B & C). From these studies, we have learned that the peak of TNF production as well as bacterial counts in survivable sepsis in this experimental model occurs at approximately 48 h (FIGS. 13B & C). Thus, the fact that our current generation of engineered HepG2 cells produces sTNFR with a lag of approximately 8-12 h and reaches a peak at approximately 24-48 (FIGS. 8 and 9) suggests that we have a realistic time frame for the inhibition of sTNFR if our goal is to allow TNF to drive bacterial killing while minimizing the tissue damaging, later auto-induction of TNF has the potential for success.

The design and refinement of the inflammation-regulating bioreactor follows an iterative, cyclic process (FIG. 5). We collect data on inflammatory analytes, markers of organ damage, and outcomes in the presence or absence of the device. We then carry out Principal Component Analysis in order to define both the "internal" variables and the "external" inputs and outputs to the model, which are the variables that can or could potentially be controlled by the theranostic device. We identify and modify the parameters that govern the model. Alternatively, the literature may be searched directly in order to extract information needed for the generation of mathematical models of inflammation in a given disease.

We describe this process in greater detail. We generate a large dataset of inflammatory analytes (which we call a vector) from the various samples taken in the rat at a specific time or from the bioreactor in vitro. We will utilize statistical analysis and data-driven modeling (predominantly using Principal Component Analysis, probit and logit models, and our recently-developed process of Dynamic Profiling [see below]) to derive information about the primary drivers of inflammation in the presence or absence of bioreactor-based intervention. The data obtained from this complementary approach will serve to 1) point us to novel components of inflammation modified by the neutralization of TNF-α; 2) help us to define parameter values for our mechanistic models; and 3) help us construct reduced mechanistic models that will be more amenable to formal analysis (as we have done in the past (Vodovotz, Y. et al. Mechanistic simulations of inflammation: Current state and future prospects. Math. Biosci. 217, 1-10 (2009)). Importantly, we will compare the predictions from statistical models with the predictions of the mechanistic models.

Standard statistical analyses (t-test, ANOVA, etc., as appropriate) of these data will be extended to the creation of data-driven models as well as our newly developed Dynamic Profiling method (see below). The statistical models would attempt to inter-relate data obtained in the course of Aims 2 and 3 by way of extracting principal components of the output vector of cytokine readings vs. relevant responses (cell death or differentiation, production of glucose or lactate by cells in the bioreactor, etc). Principal components are linear combinations of the output vector (normalized so as to have Euclidean length 1), with the property that they carry the largest variance in several orthogonal directions. This is a dimensionality reduction tool that allows one to monitor significant variation in the output of our devices, by concentrating on just a few (usually up to five or six) statistically most significant orthonormal linear combinations. These combinations are called the leading principal components. They would be our signature responses, and we will model them as a time series of correlated responses (within a patient from the various assays, and between patients as repeated measures on each patient). Repeated measurements designs, MANOVA techniques and multivariate ARIMA models with a non-diagonal covariance structure are the primary statistical tools expected to be used. Another method we would utilize involves more standard regression modeling. Though we cannot, strictly speaking, derive direct mechanistic insights from such modeling, this analysis will help us in understanding the factors that drive the temporal evolution of the pre-eminent responses, as well as highlighting the central drivers of these responses.

In parallel, we will carry out our mechanistic (mathematical) modeling studies. We will modify our existing models to account for 1) a bacterial pathogen, similar to several of our earlier mathematical models of inflammation (Clermont, G. et al. In silico design of clinical trials: a method coming of age. Crit. Care Med. 32, 2061-2070 (2004); Kumar, R., Clermont, G., Vodovotz, Y., & Chow, C. C. The dynamics of acute inflammation. J. Theoretical Biol. 230, 145-155 (2004); and Reynolds, A. et al. A reduced mathematical model of the acute inflammatory response: I. Derivation of model and analysis of antiinflammation. J. Theor. Biol. 242, 220-236 (2006)); 2) the effect of connecting just the bioreactor itself to the rat's circulation in the presence or absence of bacterial infection; 2) the effect of modulating flow rate and other parameters of the bioreactor; and finally 3) the effect of the full bioreactor that will produce sTNFR in response to TNF. We have previously studied in detail dose- and time-varying production of various cytokines, including TNF, in rats subjected to bacterial endotoxin or E. coli fibrin peritonitis (FIG. 13).

Data such as these, as well as published studies on modeling the removal of inflammatory mediators (for example (Clermont, G. et al. In silico design of clinical trials: a method coming of age. Crit. Care Med. 32, 2061-2070 (2004); Kumar, R., Chow, C. C., Bartels, J., Clermont, G., & Vodovotz, Y. A mathematical simulation of the inflammatory response to anthrax infection. Shock 29, 104-111 (2008); and Waniewski, J. & Prikrylova, D. A mathematical model of extracorporeal antibody removal in autoimmune disease. Int. J. Artif. Organs 12, 471-476 (1989)) and many others) will be used as the starting point for our simulation studies. We will start simulating the characteristics of the inflammationregulating bioreactor by modeling the basic function of the bioreactor as shown in the equations below. These simulations would progress to include data obtained on flow rates in the bioreactor, clearance rates of TNF and sTNFR, and the data derived on the relative fluorescence with respect to actual TNF and sTNFR production. In parallel, we will model the fluorescence data that will act as proxies for the production of TNF and sTNFR, using methods published by others (Wang, X., Errede, B., & Elston, T. C. Mathematical analysis and quantification of fluorescent proteins as transcriptional reporters. Biophys. J 94, 2017-2026 (2008)). This work will include estimation of the production and maturation of TurboFP635.

$$\frac{d[TNF\alpha]}{dt} = \text{Flow\_rate} \cdot C_{TNF\alpha} - r_1[sTNFR][TNF\alpha] - d_1[TNF\alpha]$$

$$\frac{d[NF\kappa B]}{dt} = K([TNF\alpha]) - d_2[NF\kappa B]$$

$$\frac{d[sTNFR]}{dt} = G([NF\kappa B]) - r_1[sTNFR][TNF\alpha] - d_3[sTNFR]$$

$$\frac{d[C]}{dt} = r_1[sTNFR][TNF\alpha] - r_2[C]$$

Using these data, as well as data on markers of organ damage/dysfunction in the animals, we will calibrate our mathematical model to experimental data using data-fitting algorithms that we have already deployed (Chow, C. C. et al. The acute inflammatory response in diverse shock states. Shock 24, 74-84 (2005); Wang, X., Errede, B., & Elston, T. C. Mathematical analysis and quantification of fluorescent proteins as transcriptional reporters. Biophys. J 94, 2017-2026 (2008); and Torres, A. et al. Mathematical modeling of post-hemorrhage inflammation in mice: Studies using a novel, computer-controlled, closedloop hemorrhage apparatus. Shock 32, 172-178 (2009)). Given a textual specification of the equations, and values for the coefficients and initial conditions, the integrator writes out files of time series data for analytes in the model. We will collect analyte data, which will be aggregated to produce the most likely value across the population (for example, we may take the mean, median, or some more complex statistical analysis of the data). Thus, we will have created a new, general time series for each analyte. To fit the model to the data, we will begin with a set of tentative coefficient values, which may be random, or may be seeded with initial values that take advantage of some expert knowledge of the system. In each iteration, a new set of candidate values will be generated, the resulting model will be evaluated, and the prediction error of the model will be computed with respect to the aggregated time series. This error information will be then direct the choice of parameter values in the ensuing iteration. This process will be repeated until our searches have converged upon a point whose error cannot be improved, thus producing the best-fit model for the population.

EXAMPLE 3—TNF-STNFR PLASMID

FIG. 14A shows a plasmid map for plasmid TNF-sTNFR (pLenti6-3×NFkB-sTNFR-IresTurboFP). The plasmid contains three copies of the NF-kB responsive elements with a reduced thymidine kinase (TK) promoter driving a coding sequence for sTNFR1a (soluble TNF-α receptor). Other features include: IRES (Internal Ribosomal Entry site, which allows production of a second protein from same mRNA; TurboFP635 (modified red fluorescent protein, with a short maturation time) and BlasticidineR (gene conferring resistance to the antibiotic compound Blasticidine; stably transfected lines can be selected by Blasticidine resistance). In response to TNF stimulation, cells will produce sTNFR1A and TurboFP635. Of note, genes carried on lentiviral vectors, such as pLenti6.3, can be integrated by lentiviral transduction methods as are known in the art.

All vectors were sequenced with using BigDye3.1 sequencing kit on ABI3100 or ABI3730 sequencer. FIG. 14B provides confirmatory sequences for pertinent portions of plasmid TNF-sTNFR.

Other NF-κB-responsive promoters were tested, as shown in FIG. 15. It should be recognized that different promoters can yield different results, depending on the cell type, though in most cases choice of promoter would be a matter of optimization for a given disease application based on the statistical and mathematical modeling analysis described above.

EXAMPLE 4—IL-1-IL-1RA PLASMID

FIG. 16A shows a plasmid map for plasmid IL-1-IL-1ra (IL1RE-IL1ra-IresTurboFP-lenti6.3). The plasmid comprises three copies of the IL-10 responsive elements with reduced TK promoter driving production of IL-1ra (soluble IL-1 receptor). Other features include: IRES (Internal Ribosomal Entry site, which allows production of a second protein from same mRNA; TurboFP635 (modified red fluorescent protein); and BlasticidineR (gene conferring resistance to the antibiotic compound Blasticidine; stably transfected lines can be selected by Blasticidine resistance). In response to IL-1 stimulation, cells will produce IL-1ra and TurboFP635. FIG. 16B provides confirmatory sequences for pertinent portions of plasmid IL-1-IL-1ra.

For the backbone of this construct, we used pLenti6.3N5DEST_verA_R1R2 (from Invitrogen). Our insert is 3×IL1RE-TK-IL1rn-IRES-TurboFP635. IRES is derived from the Clonetech pIRES vector. It contains a GC-rich region which cannot be sequenced, and therefore might contain differences from the depicted sequence. In an additional experiment, we switched from IRES to IRES2, which is much stronger and should produce increased amounts of fluorescent protein. We also can use a "self-cleaving" peptide sequence (like T2A, P2A, etc., see, e.g., Szymczak et al., Correction of multi-gene deficiency in vivo using a single 'self-cleaving' 2A peptide-based retroviral vector. Nat. Biotechnol. 2004 May; 22(5):589-94. Epub 2004 Apr. 4) for co-production therapeutic protein and detection protein.

Although we are currently using TurboFP635 as a fluorescent tag or indicator, other fluorescent/luminescent proteins should be equally useful in this context. That said, we believe that TurboFP635 and TagGFP (both from "Evrogen") are preferred because they have very short maturation time (12-24 min) as compare with most other proteins. For optimal detection, fast-maturing and degrading proteins are most desirable.

EXAMPLE 5—ALTERNATIVE TNF-STNFR PLASMID

FIG. 17A shows a plasmid map for an alternative TNF-sTNFR plasmid (pLenti6-3×NFkBsTNFR-T2A-TurboFP). The plasmid comprises three copies of an NF-κB responsive elements with reduced TK promoter driving production of sTNFR1a (soluble TNF receptor). Other features include: T2A ("self-cleaving" peptide); TurboFP635; and BlasticidineR (gene conferring resistance to the antibiotic compound Blasticidine; stably transfected lines can be selected by Blasticidine resistance). In response to stimulation with TNF-α, cells will produce sTNFR1A and TurboFP635 proteins. FIG. 17B provides confirmatory sequences for pertinent portions of plasmid pLenti6-3×NFkB-sTNFR-T2ATurboFP.

EXAMPLE 6—TNF-TURBOFP PLASMID

FIG. 18A shows a plasmid map for a TNF-TurboFP plasmid (pLENTI6-3×NFkB-TurboFP). The plasmid comprises three copies of the NF-κB responsive elements with reduced TK promoter driving production of TurboFP635. The plasmid also contains BlasticidineR, so that stably transfected lines can be selected by Blasticidine resistance. In response to stimulation with TNF-α, cells will produce TurboFP635 protein. This vector can be used as a diagnostic for TNF-α (and by inference, possibly also for the general or local inflammatory state of the patient) by fluorescence. FIG. 18B provides confirmatory sequences for pertinent portions of plasmid pLENTI6-3×NFkB-TurboFP.

EXAMPLE 7—LAP EXPRESSION VECTOR

A plasmid can be produced operably linking the TGFbeta responsive element (from the PAI-1 promoter) 5'-TCGA-GAGCCAGACAAAAAGCCAGACATTTAGCCAGA-CAC-3' (SEQ ID NO: 7). 12 copies of this sequence before minimal adenovirus MLP promoter can give stimulation 1300 folds in HepG2 cells (see, Dennler, S. et al. The EMBO Journal Vol. 17 No. 11 pp. 3091-3100, 1998; see also GenBank Accession No. NM_000660 for the structure of TGFbeta1 and FIG. 19.

EXAMPLE 8—MODELING OF TRAUMATIC BRAIN INJURY

Below, we describe various aspects of work designed to yield a mathematical model of the inflammatory response in the setting of traumatic brain injury (TBI). Such a mathematical model is envisioned as serving for the prediction of the injury outcome and for selecting an efficient treatment protocol (including a treatment using a specifically-tailored inflammation-regulating bioreactor described extensively above). Such a computational model could relate the cytokine data of patients with the patients' health or local or overall extent of tissue damage.

In our work, we utilized cytokine data for several patients with TBI. There are several obstacles for constructing good mathematical model from the given data set. One concern is that the dimension of the data set is quite large (13) so we cannot directly associate data with model variables since the resulting model would be too complicated. We addressed this issue by performing statistical analysis on the data. We used principal component analysis (PCA) to reduce the dimension of data, and also we carried out correlation analysis to further reduce redundant variables. A limitation is that we do not have data representing such important components of the immune response as the concentration of the inflammatory cells and measure of damage. Without these components it is more difficult to calibrate our prediction of inflammatory cells concentration and damage accurately, and this may lead to several models with the same fitting result for the cytokine data but with different behavior of predicted damage. We are going to overcome this difficulty by constructing the ensemble of models (Daun et al., 2008).

We obtained cytokine data for 33 patients. The data is given for the following cytokines: IL-1β, IL-2, IL-4, IL-5, IL-6, IL-8, TNF-α, IL-13, MIP-1α, MIP-1β, VEGF, IL-1α, and IL-10. Therefore, the dimension of cytokine data is 13. Besides cytokine data we also have some patient related data such as patient age, gender, etc. For each patient data is given at discrete time points. The average number of time points for all patients is 13.

To reduce the dimension of cytokine data we first carried out a principal component analysis and correlation analysis (PCA) for this data. Both analyses were performed on all cytokine data at once without consideration of different time points and distinct patients. The main reason for such procedure was that we don't have much data for each patient and the number of patients is relatively small. For every statistical analysis (and for PCA especially) it is best to have as many data points as possible to obtain the best results. So it was better to use a mixed data rather than to use small amount of data. We obtained the results shown in FIG. 20 from PCA of the original cytokine data.

It is seen from FIG. 20 that IL-6 and IL-8 played the main role in the first principal component. But these results do not give much information about data because the principal role of those cytokines can be easily explained by the fact that their values change in the most significant way from almost 0 to more than 1000; meanwhile, other cytokines do not change to the same extent. Hence, the variances of IL-6 and IL-8 are very high and they contribute to the principal components more than others. To address this issue we normalized the data by dividing each column of cytokine data by its norm. After this we performed PCA again and obtained the results shown in FIG. 21

Now it is seen that the first principal component is a linear combination of TNF-α, MIP-1α, MIP1β, IL-8, IL-10, IL-6. It is a plausible result since in many mathematical models of inflammation response the cytokines from this list are used.

To reduce the dimension of cytokine data even more we also looked at the correlation matrix of cytokines. There were quite high correlation coefficients between MIP-1α and MIP-1β, as well as between IL-8 and IL-6. Since MIP-1α, MIP-1β, and IL-8 are chemokines we decided to use only one variable describing chemokine instead of three variables. Therefore we are left with only three cytokines: pro-inflammatory cytokines TNF-α, IL-6, and anti-inflammatory cytokine IL-10. Throughout the following analysis, only TNF-α, IL-6, and IL-10 were analyzed.

Cytokine data for each patient (33) were reviewed (data not shown). From the visual examination of graphs showing cytokine data over time, IL-6 demonstrated the most interesting behavior. For most of the patients the initial value of IL-6 was high and it rapidly decayed to low value. Then IL-6 has a peak near t=40, or near t=70, or it has both these peaks. At the end of the observation, IL-6 begins to decay. TNF-α also has a prominent peak for some patients. Peaks of IL-10 occur a moment later after peaks of IL-6 and TNF-α, which confirms the anti-inflammatory nature of IL-10: when inflammation progresses (the level of IL-6 and TNF-α are high), then more IL-10 is produced, and as result the inflammatory response decays.

To better understand the relation between time and peaks of cytokines we carried out the following analysis. First of all, we unified the time scale for all patients. In order to achieve this we divided the time interval [0, 120] into 20 intervals of equal length, and considered linear interpolation of the cytokine data for each patient. Then we chose the middle point of each interval and took the average value of each cytokine at each interval. After this procedure we got cytokine data for all patients at the same time points. If the data for any patient at the particular interval was missing then we assigned special value for such an interval. The next step was to analyze the distribution of peaks of cytokines in time. We decided not to simply compare the value of cytokines at the given point with some threshold value to understand whether the value of cytokine is high or low, but instead we computed the local variance for each cytokine (local in the sense that we took only 3-4 points for computing the variance) and then we compared this value with a threshold value. If at the given point the local variance was high then we assigned 1 to this point (interval), otherwise we assigned 0. After processing all patients we got three matrices of 0's and 1's (the rows of matrices corresponded to the patients, and the columns to the time) which represented the behavior of cytokines in time: one (1) stands for significant changes of values (i.e. a peak), and zero (0) tells that there is no significant changes. We then summed up the numbers of ones at each column and divided these values by the number of patients for which data was available for the given interval. We plotted the resulting vector and obtained the distribution of local variance (peaks in some sense) for cytokines in time.

FIG. 22 confirms that IL-6 indeed has peaks at t=40 and t=70 for many patients, and also that its initial value is high and decays immediately.

From FIG. 23, for TNF-α it is not very easy to draw any useful conclusions. It seems that the peaks of TNF-α can occur at any time. This supports the conclusion that result that TNF-α plays a significant role in the PCA.

FIG. 24 for IL-10 partially resembles the figure for IL-6. But the initial value of IL-10 is low and increases.

We constructed several ordinary differential equation) mathematical models for the inflammatory response that accompanies TBI. Herein, only 2 models are presented. As indicated above, a limitation here is that we have data only for cytokines, and no data for damage or inflammatory cells. Cytokines are produced by inflammatory cells, which in turn are directly activated by cytokines and indirectly activated by tissue damage. All models have the same number of variables and equations: damage D, inflammatory cells M, chemokine C, TNF-α, IL-10, and IL-6. Relations between these variables are presented in FIG. 25.

FIG. 25 is a diagram showing relations between variables for TBI used in the ordinary differential equation modeling described below. Solid lines represent production and dashed lines represent inhibition.

The first model is described by the following equations:

$$\frac{dD}{dt} = d_0 M - d_1 D,$$

$$\frac{dM}{dt} = \frac{m_0 D}{1 + m_1 D} + \frac{m_2 C}{1 + m_3 C} - m_4(M - 1),$$

$$\frac{dC}{dt} = \frac{c_0 D}{1 + c_1 D} - c_2 C,$$

$$\frac{dIL_{10}}{dt} = i_0 M - i_1 IL_{10},$$

$$\frac{dTNF}{dt} = \frac{t_0 M}{1 + t_1 IL_{10}} - t_2 TNF,$$

$$\frac{dIL_6}{dt} = \frac{b_0 M^6}{1 + b_1 IL_{10}} - b_2 IL_6.$$

We used the simplest possible equation for the damage. The equation describing the time evolution of inflammatory cells (M) plays a central role in this mathematical model, because the level of these cells regulates the level of all cytokines in this model. The decaying term for M is of the form (M−1) because we wanted to put a lower bound for M at the level 1 in order to take advantage of high powers of M: if the level of M were less than 1, then the high powers of M would result in a slow growth rate (while our intention is in fact to use high powers to represent high growth rate). We used the sixth power of M in the equation describing the time evolution of IL-6 because our experiments with lower powers gave poorer results when attempting to fit to the cytokine data from TBI patients (data not shown). Actually, the high power of M in the equation for IL-6 can be explained from the behavior of IL6, namely that this cytokine changes rapidly from low values to high values. This case is used to illustrate a specific example; other powers may also be used in order to fit the mathematical model to patient data. The obvious problem with this model is that there is no feedback (positive or negative) from the equations for cytokines to the first three equations. Nevertheless, the fitting results, even for this simple model, were good.

Our next model is the following:

$$\frac{dD}{dt} = d_0 M - d_1 D,$$

$$\frac{dM}{dt} = \left( \frac{m_0 D}{1+m_1 D} + \frac{m_2 C}{1+m_3 C} + \frac{M_4 TNF}{1+m_5 TNF} + \frac{m_6 IL_6}{1+m_7 IL_6} \right) \frac{1}{1+m_8 IL_{10}} - m_9 M,$$

$$\frac{dC}{dt} = \frac{c_0 D}{1+c_1 D} - c_2 C,$$

$$\frac{dIL_{10}}{dt} = i_0 M - i_1 IL_{10},$$

$$\frac{dTNF}{dt} = \frac{t_0 M}{1+t_1 IL_{10}} - t_2 TNF,$$

$$\frac{dIL_6}{dt} = \frac{b_0 M^6}{1+b_1 IL_{10}} - b_2 IL_6.$$

Here we changed only the equation for inflammatory cells. This mathematical model incorporates the positive feedback from pro-inflammatory cytokines IL-6 and TNF, and negative feedback from the anti-inflammatory cytokine IL-10. This model showed better fitting results than the first model.

Before fitting our models to the actual TBI patient data, we modified the data values themselves. We multiplied the cytokine data by appropriate coefficients to get approximately the same scale for all cytokines. We did this in order to have the same boundaries for parameters in our model. For each model we have three more parameters: the initial values of tissue or overall damage, inflammatory cells, and chemokine. We wrote a MatLab code for performing fitting procedure for our models. At this time, we fit each model for individual patients only.

Our fitting procedure is the following. We choose one patient, then we choose the initial guess for parameters (randomly or based on previous parameter estimations), and we use the Nelder-Mead simplex method for parameter optimization. The error function in our case is the sum of errors between computed values of cytokines from our equations and the values from original data set (we compute the Euclidean distance between two data vectors). Other methods for parameter fitting, either published or proprietary, may also be used for this purpose.

The results for several patients were obtained for both models, or for the second model only.

As a subsequent step, an analysis of the parameter set thus obtained would be performed to understand the relations between and among the parameters.

In future work, we will continue improving our model, though we we want to keep the model quite simple, and not consider large complicated models with hundreds of parameters. Next we plan to find a way to divide patients who have the similar cytokine behavior into groups, and then try to fit all patients in one group using the same set of parameters (only initial values of damage, M, and C may be different for distinct patients). Also, we intend to construct an ensemble of models to better predict the behavior of the damage just from one model with fixed parameters.

We claim:

1. A method of inhibiting tumor necrosis factor-alpha (TNF-α) comprising, providing blood of a patient to an extracorporeal bioreactor, wherein the extracorporeal bioreactor comprises: a compartment comprising cells and a selectively permeable membrane in contact with the cells that does not permit passage of the cells and which permits passage of TNF-α in the blood of the patient, wherein the cells comprise a chimeric gene comprising a response element operably linked to a sequence encoding a soluble TNF-α receptor (sTNFR), in which the response element causes expression of the sTNFR when the cells are contacted with the TNF-α in the blood of the patient; contacting the blood with the selectively permeable membrane, such that the TNF-α in the blood passes through the selectively permeable membrane and sTNFR produced by the cells passes into the blood; and returning the blood to the patient, thereby inhibiting TNF-α.

2. The method of claim 1, in which the cells are selected by use of a computer model of an inflammatory response characteristic of a disease or condition in the patient.

3. The method of claim 1, in which the patient is a TBI patient.

4. The method of claim 1, in which the compartment comprising the cells comprises a plurality of selectively permeable hollow fibers passing through the compartment in which the plurality of hollow fibers are fluidly connected to a plasma or blood circulation system in which blood or plasma from the patient is circulated through the hollow fibers and into the patient.

5. The method of claim 1, in which the compartment comprising the cells has at least one wall that is the selectively permeable membrane, in which the selectively permeable membrane is placed in contact with a wound on the patient or a bodily fluid in situ in the patient.

6. The method of claim 5, in which the compartment comprising the cells comprises a plurality of selectively permeable hollow fibers passing through the compartment through which one or both of a gas and a fluid comprising nutrients for the cells is passed.

7. The method of claim 1, in which the cells are hepatic cells.

8. A method of inhibiting interleukin-1 (IL-1), transforming growth factor-beta1 (TGF-β1), interleukin-6 (IL-6), and/or tumor necrosis factor-alpha (TNF-α), comprising, providing blood of a patient to an extracorporeal bioreactor, wherein the extracorporeal bioreactor comprises: a compartment comprising cells and a selectively permeable membrane in contact with the cells that does not permit passage of the cells and which permits passage of IL-1, TGF-β1, IL-6, and/or TNF-α in the blood of the patient, wherein the cells comprise at least one chimeric gene comprising a response element operably linked to a sequence encoding one of: an IL-1 receptor antagonist (IL-1ra); TGF-β1 latency-associated peptide (LAP); a soluble IL-6 receptor (sIL-6R); and a soluble TNF-α receptor (sTNFR); in which the response element causes expression of the IL-1ra, LAP, sIL-6R, and/or sTNFR when the cells are contacted with the IL-1, TGF-β1, IL-6, and/or TNF-α, respectively, in the blood of the patient; contacting the blood with the selectively permeable membrane, such that the IL-1, TGF-β1, IL-6, and/or INF-α in the blood passes through the selectively permeable membrane and IL-1ra, LAP, sIL6-R, and/or sTNFR, respectively, produced by the cells passes into the blood; and returning the blood to the patient, thereby inhibiting IL-1, TGF-β1, IL-6, and/or TNF-α.

9. The method of claim 8, comprising determining levels of one or more of interleukin-1 (IL-1), transforming growth factor-beta1 (TGF-β1), interleukin 6 (IL-6), and/or tumor necrosis factor-alpha (TNF-α) in the patient, modeling inflammation associated with sepsis using the one or more levels in the patient, and determining a level of IL-1, TGF-β1, IL-6, and/or TNF-α to be controlled in the patient to determine a chimeric gene construct to place in the bioreactor based on an outcome of the modeling.

10. The method of claim 8, wherein the patient is a TBI patient.

11. The method of claim 10, comprising determining levels of one or more of interleukin-1 (IL-1), transforming growth factor-beta1 (TGF-β1), interleukin 6 (IL-6), and/or tumor necrosis factor-alpha (TNF-α) in the patient, modeling inflammation associated with TBI using the one or more levels in the patient, and determining a level of IL-1, TGF-β1, IL-6, and/or TNF-α to be controlled in the patient to determine a chimeric gene construct to place in the bioreactor based on an outcome of the modeling.

12. The method of claim 8, in which one or both of a soluble TNF-α receptor (sTNFR) and a soluble IL-6 receptor (sIL-6R) are produced by the cells.

13. The method of claim 8, in which the chimeric gene expresses an inhibitor selected from the group consisting of soluble TNF-α receptor, IL-1 receptor antagonist (IL-1ra), and TGF-β1 LAP (latency-associated peptide).

14. The method of claim 8, in which the cells comprise one or more genes that express one or both of a soluble TNF-α receptor (sTNFR) and an IL-1 receptor antagonist (IL-1ra).

15. The method of claim 8, in which the compartment comprising the cells comprises a plurality of selectively permeable hollow fibers passing through the compartment in which the plurality of hollow fibers are fluidly connected to a plasma or blood circulation system in which blood or plasma from the patient is circulated through the hollow fibers and into the patient.

16. The method of claim 8, in which the compartment comprising the cells has at least one wall that is the selectively permeable membrane, in which the selectively permeable membrane is placed in contact with a wound on the patient or a bodily fluid in situ in the patient.

17. The method of claim 8, in which the cells are hepatic cells.

* * * * *

SEQUENCE LISTING

```
<160> NUMBER OF SEQ ID NOS: 8

<210> SEQ ID NO 1
<211> LENGTH: 920
<212> TYPE: DNA
<213> ORGANISM: Artificial Sequence
<220> FEATURE:
<223> OTHER INFORMATION: Partial sequence of plasmid 3xNFkB-sTNFR-
      pcDNA3.

<400> SEQUENCE: 1
cgctgcttcg gatccgggga ctttcccggg gactttcccg gggactttcc cctcgagatc     60
cggcaaaccc cgcccagcgt cttgtcattg gcgaattcga acacgcagat gcagtcgggg    120
cggcgcggtc cgaggtccac ttcgcatatt aaggtgacgc gtgtggcctc gaacaccgag    180
cgaccctgca gcgacccgct taacagcgtc aacagcgtgc cgcagatcca ctagtaacgg    240
ccgccagtgt gctggaattc tgcagatcat gggtctcccc accgtgcctg gcctgctgct    300
gtcactggtg ctcctggctc tgctgatggg gatacatcca tcaggggtca ctggactagt    360 ccctttctctt ggtgaccggg agaagaggga tagcttgtgt ccccaaggaa agtatgtcca    420
ttctaagaac aattccatct gctgcaccaa gtgccacaaa ggaacctact tggtgagtga    480
ctgtccgagc ccagggcggg atacagtctg cagggagtgt gaaaagggca cctttacggc    540
```

```
ttcccagaat acctcaggc agtgtctcag ttgcaagaca tgtcggaaag aaatgtccca      600
ggtggagatc tctccttgcc aagctgacaa ggacacggtg tgtggctgta aggagaacca      660
gttccaacgc tacctgagtg agacacactt ccagtgcgtg gactgcagcc cctgcttcaa      720
cggcaccgtg acaatcccct gtaaggagac tcagaacacc gtgtgtaact gccatgcagg      780
gttctttctg agagaaagtg agtgcgtccc ttgcagccac tgcaagaaaa atgaggagtg      840
tatgaagttg tgcctacctc ctccgcttgc aaatgtcaca accccccagg actcaggtac      900
tgcggtgtaa gctaggatcc                                                  920
```

```
<210> SEQ ID NO 2
<211> LENGTH: 2500
<212> TYPE: DNA
<213> ORGANISM: Artificial Sequence
<220> FEATURE:
<223> OTHER INFORMATION: Partial sequence of pLenti6-3xNFkB-sTNFR-Ires-
      TurboFP.

<400> SEQUENCE: 2
ctttgtatac aaaagttgtg gatccgggga cttttcccgg gacttttccg gggactttcc       60
cctcgagatc cggcaaaccc cgcccagcgt cttgtcattg gcgaattcga acacgcagat      120
gcagtcgggg cggcgcggtc cgaggtccac ttcgcatatt aaggtgacgc gtgtggcctc      180
gaacaccgag cgaccctgca gcgacccgct taacagcgtc aacagcgtgc cgcagatcca      240
ctagtaacgg ccgccagtgt gctggaattc tgcagatcat gggtctcccc accgtgcctg      300
gcctgctgct gtcactggtg ctcctggctc tgctgatggg gatacatcca tcaggggtca      360
ctggactagt cccttctctt ggtgaccggg agaagaggga tagcttgtgt ccccaaggaa      420
agtatgtcca ttctaagaac aattccatct gctgcaccaa gtgccacaaa ggaacctact      480
tggtgagtga ctgtccgagc ccagggcggg atacagtctg cagggagtgt gaaaagggca      540
cctttacggc ttcccagaat acctcaggc agtgtctcag ttgcaagaca tgtcggaaag      600
aaatgtccca ggtggagatc tctccttgcc aagctgacaa ggacacggtg tgtggctgta      660
aggagaacca gttccaacgc tacctgagtg agacacactt ccagtgcgtg gactgcagcc      720
cctgcttcaa cggcaccgtg acaatcccct gtaaggagac tcagaacacc gtgtgtaact      780
gccatgcagg gttctttctg agagaaagtg agtgcgtccc ttgcagccac tgcaagaaaa      840
atgaggagtg tatgaagttg tgcctacctc ctccgcttgc aaatgtcaca accccccagg      900
actcaggtac tgcggtgtaa gcacccaact tttctataca aagttgctgc tagcctcgag      960
aattcacgcg tcgagcatgc atctagggcg gccaattccg cccctctccc tcccccccc     1020 ctaacgttac tggccgaagc cgcttggaat aaggccggtg tgcgtttgtc tatatgtgat     1080
tttccaccat attgccgtct tttggcaatg tgagggcccg gaaacctggc cctgtcttct     1140
tgacgagcat cctagggggt ctttcccctc tcgccaaagg aatgcaaggt ctgttgaatg     1200
tcgtgaagga agcagttcct ctggaagctt cttgaagaca acaacgtct gtagcgaccc     1260 tttgcaggca gcggaacccc ccacctggcg acaggtgcct ctgcggccaa agccacgtg      1320 tataagatac acctgcaaag gcggcacaac cccagtgcca cgttgtgagt tggatagttg     1380
tggaaagagt caaatggctc tcctcaagcg tattcaacaa ggggctgaag gatgcccaga     1440
aggtacccca ttgtatggga tctgatctgg ggcctcggtg cacatgcttt acatgtgttt     1500
agtcgaggtt aaaaaaacgt ctaggccccc cgaaccacgg ggacgtggtt ttcctttgaa     1560
aaacacgatg ataagcttgc cacaacccga caactttgta taataaagtt gctgctagcg     1620
```

```
ctaccggact cagatctcga gctcaagctt cgaattctgc agtcgacggt accgcgggcc   1680
cgggatccac cggtcgccac catggtgggt gaggatagcg tgctgatcac cgagaacatg   1740
cacatgaaac tgtacatgga gggcaccgtg aacgaccacc acttcaagtg cacatccgag   1800
ggcgaaggca agcccctacga gggcacccag accatgaaga tcaaggtggt cgagggcggc   1860
cctctcccct tcgccttcga catcctggct accagcttca tgtacggcag caaaaccttt   1920
atcaaccaca cccagggcat ccccgacttc tttaagcagt ccttccctga gggcttcaca   1980
tgggagagga tcaccacata cgaagacggg ggcgtgctga ccgctaccca ggacaccagc   2040
ctccagaacg gctgcctcat ctacaacgtc aagatcaacg gggtgaactt cccatccaac   2100
ggccctgtga tgcagaagaa aacactcggc tgggaggcca gcaccgagat gctgtacccc   2160
gctgacagcg gcctgagagg ccatagccag atggccctga agctcgtggg cggggggctac   2220 ctgcactgct ccctcaagac cacatacaga tccaagaaac ccgctaagaa cctcaagatg   2280
cccggcttct acttcgtgga caggagactg aaagaatca aggaggccga caagagacc   2340 tacgtcgagc agcacgagat ggctgtggcc aggtactgcg acctgcctag caaactgggg   2400
cacagctgat acccagctttt cttgtacaaa gttggttgat atccagcaca gtggcggccg   2460
ctcgagtcta gagggcccgc ggttcgaagg taagcctatc   2500
```

```
<210> SEQ ID NO 3
<211> LENGTH: 2286
<212> TYPE: DNA
<213> ORGANISM: Artificial Sequence
<220> FEATURE:
<223> OTHER INFORMATION: Partial sequence of IL1RE-IL1ra-IresTurboFP-
      lenti6.3

<400> SEQUENCE: 3
```

```
agttcaatta cagctcttaa ggctagagta cttaatacga ctcactatag gctagcagaa     60
tctgcttagg gttaggcgtt ttgcgctgct tcggatccac attgcacaat ctacattgca    120
caatctacat tgcacaatct ctcgagatcc ggcaaacccc gcccagcgtc ttgtcattgg    180
cgaattcgaa cacgcagatg cagtcggggc ggcgcggtcc gaggtccact tcgcatatta    240
aggtgacgcg tgtggcctcg aacaccgagc gaccctgcag cgacccgctt aacagcgtca    300
acagcgtgcc gcagatccac ccatggcttc agaggcagcc tgccgccctt ctgggaaaag    360
accctgcaag atgcaagcct tcagaatctg ggatactaac cagaagacct tttacctgag    420
aaacaaccag ctcattgctg gtacttaca aggaccaaat atcaaactag aagaaaagtt    480
agacatggtg cctattgacc ttcatagtgt gttcttgggc atccacgggg gcaagctgtg    540
cctgtcttgt gccaagtctg agatgatat caagctccag ctggaggaag ttaacatcac    600
tgatctgagc aagaacaaag aagaagacaa gcgctttacc ttcatccgct ctgagaaagg    660
ccccaccacc agctttgagt cagctgcctg tccaggatgg ttcctctgca caacactaga    720
ggctgaccgt cctgtgagcc tcaccaacac accggaagag ccccttatag tcacgaagtt    780
ctacttccag gaagaccaat agtactgccg aggcctgtaa taatcaccaa ctgcctgatc    840
actctggcga attcacgcgt cgagcatgca tctaggggcgg ccaattccgc ccctctccct    900
cccccccccc taacgttact ggccgaagcc gcttggaata aggccggtgt gcgtttgtct    960
atatgtgatt ttccaccata ttgccgtctt ttggcaatgt gagggcccgg aaacctggcc   1020
ctgtcttctt gacgagcatt cctaggggtc ttttcccctct cgccaaagga atgcaaggtc   1080
tgttgaatgt cgtgaaggaa gcagttcctc tggaagcttc ttgaagacaa acaacgtctg   1140
```

```
tagcgaccct ttgcaggcag cggaacccccc cacctggcga caggtgcctc tgcggccaaa    1200
agccacgtgt ataagataca cctgcaaagg cggcacaacc ccagtgccac gttgtgagtt    1260
ggatagttgt ggaaagagtc aaatggctct cctcaagcgt attcaacaag gggctgaagg    1320
atgcccagaa ggtaccccat tgtatgggat ctgatctggg gcctcggtgc acatgcttta    1380
catgtgttta gtcgaggtta aaaaaacgtc taggcccccc gaaccacggg gacgtggttt    1440
tcctttgaaa aacacgatga taagcttgcc acaacccggg atccaccggt cgccaccatg    1500
gtgggtgagg atagcgtgct gatcaccgag aacatgcaca tgaaactgta catggagggc    1560
accgtgaacg accaccactt caagtgcaca tccgagggcg aaggcaagcc ctacgagggc    1620
acccagacca tgaagatcaa ggtggtcgag ggcggccctc tccccttcgc cttcgacatc    1680
ctggctacca gcttcatgta cggcagcaaa acctttatca accacaccca gggcatcccc    1740
gacttcttta gcagtccttc cctgagggc ttcacatggg agaggatcac cacatacgaa    1800 gacggggggcg tgctgaccgc tacccaggac accagcctcc agaacggctg cctcatctac    1860
aacgtcaaga tcaacggggt gaacttccca tccaacggcc ctgtgatgca agaaaaaca    1920 ctcggctggg aggccagcac cgagatgctg taccccgctg acagcggcct gagaggccat    1980
agccagatgg ccctgaagct cgtgggcggg ggctacctgc actgctccct caagaccaca    2040
tacagatcca agaaacccgc taagaacctc aagatgcccg gcttctactt cgtggacagg    2100
agactggaaa gaatcaagga ggccgacaaa gagacctacg tcgagcagca cgagatggct    2160
gtggccaggt actgcgacct gcctagcaaa ctggggcaca gctgatgcgg ccgcttccct    2220
ttagtgaggg ttaatgcttc gagcagacat gacgcgtacc ggttagtaag cgtaccggtt    2280
agtaat                                                                2286

<210> SEQ ID NO 4
<211> LENGTH: 1900
<212> TYPE: DNA
<213> ORGANISM: Artificial Sequence
<220> FEATURE:
<223> OTHER INFORMATION: Partial sequence of pLenti6-3xNFkB-sTNFR-T2A-
      TurboFP.

<400> SEQUENCE: 4
cgaattctgc agtcgacggt accgcgggcc cgggatccac cggtacaact ttgtatacaa      60
aagttgtgga tccggggact ttccgggga cttttccggg gactttcccc tcgagatccg     120
gcaaaccccg cccagcgtct tgtcattggc gaattcgaac acgcagatgc agtcggggcg     180
gcgcggtccg aggtccactt cgcatattaa ggtgacgcgt gtggcctcga acaccgagcg     240
accctgcagc gacccgctta acagcgtcaa cagcgtgccg cagatccact agtaacggcc     300
gccagtgtgc tggaattctg cagatcatgg gtctccccac cgtgcctggc ctgctgctgt     360
cactggtgct cctggctctg ctgatgggga tacatccatc aggggtcact ggactagtcc     420
cttctcttgg tgaccgggag aagagggata gcttgtgtcc ccaaggaaag tatgtccatt     480
ctaagaacaa ttccatctgc tgcaccaagt gccacaaagg aacctacttg gtgagtgact     540
gtccgagccc agggcgggat acagtctgca gggagtgtga aaaggcacc tttacggctt     600 cccagaatta cctcaggcag tgtctcagtt gcaagacatg tcggaagaa atgtcccagg     660 tggagatctc tccttgccaa gctgacaagg acacggtgtg tggctgtaag gagaaccagt     720
tccaacgcta cctgagtgag acacacttcc agtgcgtgga ctgcagcccc tgcttcaacg     780
gcaccgtgac aatccctgt aaggagactc agaacaccgt gtgtaactgc catgcagggt     840
```

```
tctttctgag agaaagtgag tgcgtcccct gcagccactg caagaaaaat gaggagtgta      900
tgaagttgtg cctacctcct ccgcttgcaa atgtcacaaa ccccaggac tcaggtactg       960 cggtgtaagc acccaacttt tctatacaaa gttgctgcta gcctcgagaa ttcacgcgtc     1020
gagcatgcat ctagggcggc cacaactttg tataataaag ttgctgctag cgctaccgga     1080
ctcagatctc gagctcaagc ttcgaattct gcagtcgacg gtaccgcggg cccgggatcc     1140
accggtcgcc accatggtgg gtgaggatag cgtgctgatc accgagaaca tgcacatgaa     1200
actgtacatg gagggcaccg tgaacgacca ccacttcaag tgcacatccg agggcgaagg     1260
caagccctac gagggcaccc agaccatgaa gatcaaggtg tcgagggcg ccctctccc       1320 cttcgccttc gacatcctgg ctaccagctt catgtacggc agcaaaacct tatcaacca     1380 cacccagggc atccccgact tctttaagca gtccttccct gagggcttca catgggagag     1440
gatcaccaca tacgaagacg ggggcgtgct gaccgctacc caggacacca gcctccagaa     1500
cggctgcctc atctacaacg tcaagatcaa cggggtgaac ttcccatcca acggccctgt     1560
gatgcagaag aaaacactcg gctgggaggc cagcaccgag atgctgtacc cgctgacag     1620 cggcctgaga ggccatagcc agatggccct gaagctcgtg ggcggggct acctgcactg     1680 ctccctcaag accacataca gatccaagaa acccgctaag aacctcaaga tgcccggctt     1740
ctacttcgtg gacaggagac tggaaagaat caaggaggcc gacaaagaga cctacgtcga     1800
gcagcacgag atggctgtgg ccaggtactg cgacctgcct agcaaactgg ggcacagctg     1860
atacccagct ttcttgtaca agtggtttg atatccagca                             1900

<210> SEQ ID NO 5
<211> LENGTH: 1100
<212> TYPE: DNA
<213> ORGANISM: Artificial Sequence
<220> FEATURE:
<223> OTHER INFORMATION: Partial sequence of pLENTI6-3xNFkB-TurboFP

<400> SEQUENCE: 5
cgaattctgc agtcgacggt accgcgggcc cgggatccac cggtacaact ttgtatacaa       60
aagttgtgga tccggggact ttcccgggga ctttccccgg gactttcccc tcgagatccg     120
gcaaaccccg cccagcgtct tgtcattggc gaattcgaac acgcagatgc agtcggggcg     180
gcgcggtccg aggtccactt cgcatattaa ggtgacgcgt gtggcctcga acaccgagcg     240
accctgcagc gacccgctta acagcgtcaa cagcgtgccg cagatccact agtaacggcc     300
gccagtgtgc tggaatcgaa ttctgcagtc gacggtaccg cgggcccggg atccaccggt     360
cgccaccatg gtgggtgagg atagcgtgct gatcaccgag aacatgcaca tgaaactgta     420
catggagggc accgtgaacg accaccactt caagtgcaca tccagggcg aaggcaagcc      480 ctacgagggc acccagacca tgaagatcaa ggtggtcgag ggcggccctc tcccttcgc      540 cttcgacatc ctggctacca gcttcatgta cggcagcaaa accttatca ccacaccca       600 gggcatcccc gacttcttta agcagtcctt ccctgagggc ttcacatggg agaggatcac     660
cacatacgaa gacggggcg tgctgaccgc tacccaggac accagcctcc agaacggctg      720
cctcatctac aacgtcaaga tcaacggggt gaacttccca tccaacggcc ctgtgatgca     780
gaagaaaaca ctcggctggg aggccagcac cgagatgctg taccccgctg acagcggcct     840
gagaggccat agccagatgg ccctgaagct cgtgggcggg ggctacctgc actgctccct     900
caagaccaca tacagatcca agaaacccgc taagaacctc aagatgcccg gcttctactt     960
```

| | |
|---|---|
| cgtggacagg agactggaaa gaatcaagga ggccgacaaa gagacctacg tcgagcagca | 1020 |
| cgagatggct gtggccaggt actgcgacct gcctagcaaa ctggggcaca gctgataccc | 1080 |
| agctttcttg tacaaagtgg | 1100 |

<210> SEQ ID NO 6
<211> LENGTH: 1780
<212> TYPE: DNA
<213> ORGANISM: Homo sapiens

<400> SEQUENCE: 6

| | |
|---|---|
| acacggcgtc cctcaggcgc ccccattccg gaccagccct cgggagtcgc cgacccggcc | 60 |
| tcccgcaaag acttttcccc agacctcggg cgcaccccct gcacgccgcc ttcatccccg | 120 |
| gcctgtctcc tgagccccccg cgcatcctag accctttctc ctccaggaga cggatctctc | 180 |
| tccgacctgc cacagatccc ctattcaaga ccacccacct tctggtacca gatcgcgccc | 240 |
| atctaggtta tttccgtggg atactgagac accccggtc caagcctccc ctccaccact | 300 |
| gcgcccttct ccctgaggac ctcagctttc cctcgaggcc ctcctacctt ttgccgggag | 360 |
| acccccagcc cctgcagggg cggggcctcc ccaccacacc agccctgttc gcgctctcgg | 420 |
| cagtgccggg gggcgccgcc tcccccatgc cgccctccgg gctgcggctg ctgctgctgc | 480 |
| tgctaccgct gctgtggcta ctggtgctga cgccggccg gccggccgcg ggactatcca | 540 |
| cctgcaagac tatcgacatg gagctggtga agcggaagcg catcgaggcc atcgcgggcc | 600 |
| agatcctgtc caagctgcgg ctcgccagcc cccgagcca gggggaggtg ccgcccggcc | 660 |
| cgctgcccga ggccgtgctc gccctgtaca acagcacccg cgaccgggtg gccggggaga | 720 |
| gtgcagaacc ggagcccgag cctgaggccg actactacgc caaggaggtc acccgcgtgc | 780 |
| taatggtgga aacccacaac gaaatctatg acaagttcaa gcagagtaca cacagcatat | 840 |
| atatgttctt caacacatca gagctccgag aagcggtacc tgaacccgtg ttgctctccc | 900 |
| gggcagagct gcgtctgctg aggctcaagt taaaagtgga gcagcacgtg gagctgtacc | 960 |
| agaaatacag caacaattcc tggcgatacc tcagcaaccg gctgctggca cccagcgact | 1020 |
| cgccagagtg gttatctttt gatgtcaccg gagttgtgcg gcagtggttg agccgtggag | 1080 |
| gggaaattga gggctttcgc cttagcgccc actgctcctg tgacagcagg gataacacac | 1140 |
| tgcaagtgga catcaacggg ttcactaccg gcgccgaggt gacctggcc accattcatg | 1200 |
| gcatgaaccg gccttttcctg cttctcatgg ccaccccgct ggagagggcc cagcatctgc | 1260 |
| aaagctcccg gcaccgccga gccctggaca ccaactattg cttcagctcc acggagaaga | 1320 |
| actgctgcgt gcggcagctg tacattgact tccgcaagga cctcggctgg aagtggatcc | 1380 |
| acgagcccaa gggctaccat gccaacttct gcctcgggcc ctgccctac atttggagcc | 1440 |
| tggacacgca gtacagcaag gtcctggccc tgtacaacca gcataacccg ggcgcctcgg | 1500 |
| cggcgccgtg ctgcgtgccg caggcgctgg agccgctgcc catcgtgtac tacgtgggcc | 1560 |
| gcaagcccaa ggtggagcag ctgtccaaca tgatcgtgcg ctcctgcaag tgcagctgag | 1620 |
| gtcccgcccc gccccgcccc gcccggcag gccggcccc acccgcccc gccccgctg | 1680 |
| ccttgcccat gggggctgta tttaaggaca cccgtgccca agcccacctg gggcccatt | 1740 |
| aaagatggag agaggactgc gaaaaaaaaa aaaaaaaaa | 1780 |

<210> SEQ ID NO 7
<211> LENGTH: 39
<212> TYPE: DNA
<213> ORGANISM: Artificial Sequence

```
-continued

<220> FEATURE:
<223> OTHER INFORMATION: PAI-1 promoter sequence

<400> SEQUENCE: 7
tcgagagcca gacaaaaagc cagacattta gccagacac                                    39

<210> SEQ ID NO 8
<211> LENGTH: 60
<212> TYPE: DNA
<213> ORGANISM: Artificial Sequence
<220> FEATURE:
<223> OTHER INFORMATION: Control sequence for IL-6 Construct

<400> SEQUENCE: 8
gtatttccca gaaaggaac gtatttccca gaaaaggaac gtatttccca gaaaaggaac      60
```

UNITED STATES PATENT AND TRADEMARK OFFICE
CERTIFICATE OF CORRECTION

PATENT NO. : 10,137,236 B2
APPLICATION NO. : 14/301734
DATED : November 27, 2018
INVENTOR(S) : Yoram Vodovotz et al.

Page 1 of 1

It is certified that error appears in the above-identified patent and that said Letters Patent is hereby corrected as shown below:

In the Specification

Column 1, Line 15, insert the following new header -- STATEMENT REGARDING FEDERAL FUNDING --

Column 1, Lines 17 & 18, insert -- This invention was made with government support under grant number W81XWH-07-1-0415 awarded by the United States Army Medical Research and Material Command (ARMY/MRMC) and grant number GM107231 awarded by the National Institutes of Health. The government has certain rights in the invention. --

In the Claims

Column 44, Line 32, Claim 8, delete "INF-α" and insert -- TNF-α --

Signed and Sealed this
Twelfth Day of March, 2019

Andrei Iancu
*Director of the United States Patent and Trademark Office*